United States Patent
Hindson et al.

(10) Patent No.: US 10,450,607 B2
(45) Date of Patent: Oct. 22, 2019

(54) METHODS AND SYSTEMS FOR PROCESSING POLYNUCLEOTIDES

(71) Applicant: 10X GENOMICS, INC., Pleasanton, CA (US)

(72) Inventors: Benjamin Hindson, Pleasanton, CA (US); Christopher Hindson, Pleasanton, CA (US); Michael Schnall-Levin, Palo Alto, CA (US); Kevin Ness, Pleasanton, CA (US); Mirna Jarosz, Mountain View, CA (US); Serge Saxonov, Oakland, CA (US)

(73) Assignee: 10X GENOMICS, INC., Pleasanton, CA (US)

(*) Notice: Subject to any disclaimer, the term of this patent is extended or adjusted under 35 U.S.C. 154(b) by 0 days.

(21) Appl. No.: 16/294,769

(22) Filed: Mar. 6, 2019

(65) Prior Publication Data

US 2019/0203291 A1    Jul. 4, 2019

Related U.S. Application Data

(60) Continuation of application No. 16/231,185, filed on Dec. 21, 2018, which is a continuation of application No. 16/212,441, filed on Dec. 6, 2018, which is a continuation of application No. 16/052,431, filed on Aug. 1, 2018, now Pat. No. 10,273,541, which is a continuation-in-part of application No. 16/000,803, filed on Jun. 5, 2018, which is a continuation of application No. 15/850,241, filed on Dec. 21, 2017, which is a continuation of application No. 15/588,519, filed on May 5, 2017, now Pat. No. 9,856,530, which is a continuation of application No. 15/376,582, filed on Dec. 12, 2016, now Pat. No. 9,701,998, which is a continuation-in-part of application No. 14/104,650, filed on Dec. 12, 2013, now Pat. No. 9,567,631, said application No. 15/376,582 is a continuation-in-part of application No. 14/250,701, filed on Apr. 11, 2014, now abandoned, which is a continuation of application No. 14/175,973, filed on Feb. 7, 2014, now Pat. No. 9,388,465, said application No. 16/231,185 is a continuation-in-part of application No. 15/847,752, filed on Dec. 19, 2017, which is a continuation of application No. 15/717,871, filed on Sep. 27, 2017, now Pat. No. 9,951,386, which is a continuation-in-part of application No. 14/752,641, filed on Jun. 26, 2015, said application No. 16/052,431 is a continuation-in-part of application No. 15/598,898, filed on May 18, 2017, which is a continuation of application No. 14/624,468, filed on Feb. 17, 2015, now Pat. No. 9,689,024, which is a division of application No. 13/966,150, filed on Aug. 13, 2013, now abandoned, said application No. 16/231,185 is a continuation-in-part of application No. 16/052,486, filed on Aug. 1, 2018, now Pat. No. 10,323,279, which is a continuation-in-part of application No. 16/000,803, filed on Jun. 5, 2018, and a continuation-in-part of application No. 14/316,447, filed on Jun. 26, 2014, now Pat. No. 10,221,442, which is a continuation-in-part of application No. 13/966,150, filed on Aug. 13, 2013, now abandoned, and a continuation-in-part of application No. PCT/US2013/054797, filed on Aug. 13, 2013.

(60) Provisional application No. 61/737,374, filed on Dec. 14, 2012, provisional application No. 61/844,804, filed on Jul. 10, 2013, provisional application No. 61/840,403, filed on Jun. 27, 2013, provisional (Continued)

(51) Int. Cl.
| | |
|---|---|
| C12Q 1/68 | (2018.01) |
| C12Q 1/6874 | (2018.01) |
| C12Q 1/6855 | (2018.01) |
| C12Q 1/6806 | (2018.01) |
| C12Q 1/6869 | (2018.01) |

(52) U.S. Cl.
CPC ......... *C12Q 1/6874* (2013.01); *C12Q 1/6806* (2013.01); *C12Q 1/6855* (2013.01); *C12Q 1/6869* (2013.01)

(58) Field of Classification Search
CPC ........................... C12Q 1/6804; C12Q 1/6874
See application file for complete search history.

(56) References Cited

U.S. PATENT DOCUMENTS

| | | |
|---|---|---|
| 2,797,149 A | 6/1957 | Skeggs |
| 3,047,367 A | 7/1962 | Kessler |

(Continued)

FOREIGN PATENT DOCUMENTS

| | | |
|---|---|---|
| CN | 102292455 A | 12/2011 |
| CN | 103202812 A | 7/2013 |

(Continued)

OTHER PUBLICATIONS

AH006633.3 (*Homo sapiens* clone P1 and PAC max interactor 1 (MXI1) gene, complete cds, NCBI Reference Sequence, priority to Jun. 10, 2016, 5 pages) (Year:2016).
Ahern, H. The Scientist, vol. 20, pp. 20 and 22. July (Year: 1995).
Ailenberg, et al. (2000) Controlled Hot Start and Improved Specificity in Carrying Out PCR Utilizing Touch-Up and Loop Incorporated Primers (TULIPS). BioTechniques, 29:1018-1024. (Year: 2000).

(Continued)

*Primary Examiner* — David C Thomas
(74) *Attorney, Agent, or Firm* — Wilson Sonsini Goodrich & Rosati

(57) ABSTRACT

The present disclosure provides compositions, methods, systems, and devices for polynucleotide processing. Such polynucleotide processing may be useful for a variety of applications, including polynucleotide sequencing.

57 Claims, 22 Drawing Sheets

Related U.S. Application Data application No. 61/800,223, filed on Mar. 15, 2013, provisional application No. 61/762,435, filed on Feb. 8, 2013, provisional application No. 62/061,567, filed on Oct. 8, 2014, provisional application No. 62/017,558, filed on Jun. 26, 2014, provisional application No. 61/683,192, filed on Aug. 14, 2012, provisional application No. 61/896,060, filed on Oct. 26, 2013, provisional application No. 61/909,974, filed on Nov. 27, 2013, provisional application No. 61/991,018, filed on May 9, 2014, provisional application No. 61/940,318, filed on Feb. 14, 2014, provisional application No. 61/937,344, filed on Feb. 7, 2014.

(56) References Cited

U.S. PATENT DOCUMENTS

| | | |
|---|---|---|
| 3,479,141 A | 11/1969 | William et al. |
| 4,124,638 A | 11/1978 | Hansen |
| 4,253,846 A | 3/1981 | Smythe et al. |
| 4,582,802 A | 4/1986 | Zimmerman et al. |
| 5,137,829 A | 8/1992 | Nag et al. |
| 5,149,625 A | 9/1992 | Church et al. |
| 5,185,099 A | 2/1993 | Delpuech et al. |
| 5,202,231 A | 4/1993 | Drmanac et al. |
| 5,270,183 A | 12/1993 | Corbett et al. |
| 5,413,924 A | 5/1995 | Kosak et al. |
| 5,418,149 A | 5/1995 | Gelfand et al. |
| 5,436,130 A | 7/1995 | Mathies et al. |
| 5,478,893 A | 12/1995 | Ghosh et al. |
| 5,489,523 A | 2/1996 | Mathur |
| 5,512,131 A | 4/1996 | Kumar et al. |
| 5,558,071 A | 9/1996 | Ward et al. |
| 5,585,069 A | 12/1996 | Zanzucchi et al. |
| 5,587,128 A | 12/1996 | Wilding et al. |
| 5,605,793 A | 2/1997 | Stemmer et al. |
| 5,618,711 A | 4/1997 | Gelfand et al. |
| 5,695,940 A | 12/1997 | Drmanac et al. |
| 5,700,642 A | 12/1997 | Monforte et al. |
| 5,705,628 A | 1/1998 | Hawkins et al. |
| 5,708,153 A | 1/1998 | Dower et al. |
| 5,736,330 A | 4/1998 | Fulton |
| 5,739,036 A | 4/1998 | Parris |
| 5,744,311 A | 4/1998 | Fraiser et al. |
| 5,756,334 A | 5/1998 | Perler et al. |
| 5,830,663 A | 11/1998 | Embleton et al. |
| 5,834,197 A | 11/1998 | Parton |
| 5,842,787 A | 12/1998 | Kopf-Sill et al. |
| 5,846,719 A | 12/1998 | Brenner et al. |
| 5,846,727 A | 12/1998 | Soper et al. |
| 5,851,769 A | 12/1998 | Gray et al. |
| 5,856,174 A | 1/1999 | Lipshutz et al. |
| 5,872,010 A | 2/1999 | Karger et al. |
| 5,897,783 A | 4/1999 | Howe et al. |
| 5,900,481 A | 5/1999 | Lough et al. |
| 5,942,609 A | 8/1999 | Hunkapiller et al. |
| 5,958,703 A | 9/1999 | Dower et al. |
| 5,965,443 A | 10/1999 | Reznikoff et al. |
| 5,994,056 A | 11/1999 | Higuchi |
| 5,997,636 A | 12/1999 | Gamarnik et al. |
| 6,033,880 A | 3/2000 | Haff et al. |
| 6,046,003 A | 4/2000 | Mandecki |
| 6,051,377 A | 4/2000 | Mandecki |
| 6,057,107 A | 5/2000 | Fulton |
| 6,057,149 A | 5/2000 | Burns et al. |
| 6,103,537 A | 8/2000 | Ullman et al. |
| 6,110,678 A | 8/2000 | Weisburg et al. |
| 6,123,798 A | 9/2000 | Gandhi et al. |
| 6,133,436 A | 10/2000 | Koster et al. |
| 6,143,496 A | 11/2000 | Brown et al. |
| 6,159,717 A | 12/2000 | Savakis et al. |
| 6,171,850 B1 | 1/2001 | Nagle et al. |
| 6,172,218 B1 | 1/2001 | Brenner |
| 6,207,384 B1 | 3/2001 | Mekalanos et al. |
| 6,258,571 B1 | 7/2001 | Chumakov et al. |
| 6,265,552 B1 | 7/2001 | Schatz |
| 6,291,243 B1 | 9/2001 | Fogarty et al. |
| 6,294,385 B1 | 9/2001 | Goryshin et al. |
| 6,296,020 B1 | 10/2001 | McNeely et al. |
| 6,297,006 B1 | 10/2001 | Drmanac et al. |
| 6,297,017 B1 | 10/2001 | Schmidt et al. |
| 6,303,343 B1 | 10/2001 | Kopf-Sill |
| 6,306,590 B1 | 10/2001 | Mehta et al. |
| 6,327,410 B1 | 12/2001 | Walt et al. |
| 6,355,198 B1 | 3/2002 | Kim et al. |
| 6,361,950 B1 | 3/2002 | Mandecki |
| 6,372,813 B1 | 4/2002 | Johnson et al. |
| 6,379,929 B1 | 4/2002 | Burns et al. |
| 6,406,848 B1 | 6/2002 | Bridgham et al. |
| 6,409,832 B2 | 6/2002 | Weigl et al. |
| 6,432,290 B1 | 8/2002 | Harrison et al. |
| 6,432,360 B1 | 8/2002 | Church |
| 6,485,944 B1 | 11/2002 | Church et al. |
| 6,492,118 B1 | 12/2002 | Abrams et al. |
| 6,511,803 B1 | 1/2003 | Church et al. |
| 6,524,456 B1 | 2/2003 | Ramsey et al. |
| 6,569,631 B1 | 5/2003 | Pantoliano et al. |
| 6,579,851 B2 | 6/2003 | Goeke et al. |
| 6,586,176 B1 | 7/2003 | Trnovsky et al. |
| 6,593,113 B1 | 7/2003 | Tenkanen et al. |
| 6,613,752 B2 | 9/2003 | Kay et al. |
| 6,632,606 B1 | 10/2003 | Ullman et al. |
| 6,632,655 B1 | 10/2003 | Mehta et al. |
| 6,670,133 B2 | 12/2003 | Knapp et al. |
| 6,723,513 B2 | 4/2004 | Lexow |
| 6,767,731 B2 | 7/2004 | Hannah |
| 6,800,298 B1 | 10/2004 | Burdick et al. |
| 6,806,052 B2 | 10/2004 | Bridgham et al. |
| 6,806,058 B2 | 10/2004 | Jesperson et al. |
| 6,859,570 B2 | 2/2005 | Walt et al. |
| 6,880,576 B2 | 4/2005 | Karp et al. |
| 6,884,788 B2 | 4/2005 | Bulpitt et al. |
| 6,913,935 B1 | 7/2005 | Thomas |
| 6,929,859 B2 | 8/2005 | Chandler et al. |
| 6,969,488 B2 | 11/2005 | Bridgham et al. |
| 6,974,669 B2 | 12/2005 | Mirkin et al. |
| 7,041,481 B2 | 5/2006 | Anderson et al. |
| 7,115,400 B1 | 10/2006 | Adessi et al. |
| 7,129,091 B2 | 10/2006 | Ismagilov et al. |
| 7,138,267 B1 | 11/2006 | Jendrisak et al. |
| 7,211,654 B2 | 5/2007 | Gao et al. |
| 7,262,056 B2 | 8/2007 | Wooddell et al. |
| 7,268,167 B2 | 9/2007 | Higuchi et al. |
| 7,282,370 B2 | 10/2007 | Bridgham et al. |
| 7,294,503 B2 | 11/2007 | Quake et al. |
| 7,297,485 B2 | 11/2007 | Bornarth et al. |
| 7,316,903 B2 | 1/2008 | Yanagihara et al. |
| 7,323,305 B2 | 1/2008 | Leamon et al. |
| 7,329,493 B2 | 2/2008 | Chou et al. |
| 7,425,431 B2 | 9/2008 | Church et al. |
| 7,536,928 B2 | 5/2009 | Kazuno |
| 7,544,473 B2 | 6/2009 | Brenner |
| 7,604,938 B2 | 10/2009 | Takahashi et al. |
| 7,608,434 B2 | 10/2009 | Reznikoff et al. |
| 7,608,451 B2 | 10/2009 | Cooper et al. |
| 7,622,280 B2 | 11/2009 | Holliger et al. |
| 7,638,276 B2 | 12/2009 | Griffiths et al. |
| 7,645,596 B2 | 1/2010 | Williams et al. |
| 7,666,664 B2 | 2/2010 | Sarofim et al. |
| 7,700,325 B2 | 4/2010 | Cantor et al. |
| 7,708,949 B2 | 5/2010 | Stone et al. |
| 7,709,197 B2 | 5/2010 | Drmanac |
| 7,745,178 B2 | 6/2010 | Dong |
| 7,745,218 B2 | 6/2010 | Kim et al. |
| 7,776,927 B2 | 8/2010 | Chu et al. |
| RE41,780 E | 9/2010 | Anderson et al. |
| 7,799,553 B2 | 9/2010 | Mathies et al. |
| 7,842,457 B2 | 11/2010 | Berka et al. |
| 7,901,891 B2 | 3/2011 | Drmanac |
| 7,910,354 B2 | 3/2011 | Drmanac et al. |
| 7,947,477 B2 | 5/2011 | Schroeder et al. |
| 7,960,104 B2 | 6/2011 | Drmanac et al. |
| 7,968,287 B2 | 6/2011 | Griffiths et al. |
| 7,972,778 B2 | 7/2011 | Brown et al. |

(56) References Cited

U.S. PATENT DOCUMENTS

| | | |
|---|---|---|
| 8,003,312 B2 | 8/2011 | Krutzik et al. |
| 8,008,018 B2 | 8/2011 | Quake et al. |
| 8,053,192 B2 | 11/2011 | Bignell et al. |
| 8,067,159 B2 | 11/2011 | Brown et al. |
| 8,101,346 B2 | 1/2012 | Takahama |
| 8,124,404 B2 | 2/2012 | Alphey et al. |
| 8,133,719 B2 | 3/2012 | Drmanac et al. |
| 8,137,563 B2 | 3/2012 | Ma et al. |
| 8,168,385 B2 | 5/2012 | Brenner et al. |
| 8,252,539 B2 | 8/2012 | Quake et al. |
| 8,268,564 B2 | 9/2012 | Roth et al. |
| 8,273,573 B2 | 9/2012 | Ismagilov et al. |
| 8,278,071 B2 | 10/2012 | Brown et al. |
| 8,298,767 B2 | 10/2012 | Brenner et al. |
| 8,304,193 B2 | 11/2012 | Ismagilov et al. |
| 8,318,433 B2 | 11/2012 | Brenner |
| 8,318,460 B2 | 11/2012 | Cantor et al. |
| 8,329,407 B2 | 12/2012 | Ismagilov et al. |
| 8,337,778 B2 | 12/2012 | Stone et al. |
| 8,361,299 B2 | 1/2013 | Sabin et al. |
| 8,420,386 B2 | 4/2013 | Ivics et al. |
| 8,461,129 B2 | 6/2013 | Bolduc et al. |
| 8,563,274 B2 | 10/2013 | Brenner et al. |
| 8,592,150 B2 | 11/2013 | Drmanac et al. |
| 8,598,328 B2 | 12/2013 | Koga et al. |
| 8,603,749 B2 | 12/2013 | Gillevet et al. |
| 8,679,756 B1 | 3/2014 | Brenner et al. |
| 8,748,094 B2 | 6/2014 | Weitz et al. |
| 8,748,102 B2 | 6/2014 | Berka et al. |
| 8,765,380 B2 | 7/2014 | Berka et al. |
| 8,822,148 B2 | 9/2014 | Ismagliov et al. |
| 8,829,171 B2 | 9/2014 | Steemers et al. |
| 8,835,358 B2 | 9/2014 | Fodor et al. |
| 8,871,444 B2 | 10/2014 | Griffiths et al. |
| 8,889,083 B2 | 11/2014 | Ismagilov et al. |
| 8,927,218 B2 | 1/2015 | Forsyth |
| 8,975,302 B2 | 3/2015 | Light et al. |
| 8,986,286 B2 | 3/2015 | Tanghoj et al. |
| 9,005,935 B2 | 4/2015 | Belyaev |
| 9,012,390 B2 | 4/2015 | Holtze et al. |
| 9,017,948 B2 | 4/2015 | Agresti et al. |
| 9,029,083 B2 | 5/2015 | Griffiths et al. |
| 9,029,085 B2 | 5/2015 | Agresti et al. |
| 9,040,256 B2 | 5/2015 | Grunenwald et al. |
| 9,068,210 B2 | 6/2015 | Agresti et al. |
| 9,074,251 B2 | 7/2015 | Steemers et al. |
| 9,080,211 B2 | 7/2015 | Grunenwald et al. |
| 9,102,980 B2 | 8/2015 | Brenner et al. |
| 9,150,916 B2 | 10/2015 | Christen et al. |
| 9,175,295 B2 | 11/2015 | Kaminaka et al. |
| 9,238,671 B2 | 1/2016 | Goryshin et al. |
| 9,249,460 B2 | 2/2016 | Pushkarev et al. |
| 9,273,349 B2 | 3/2016 | Nguyen et al. |
| 9,290,808 B2 | 3/2016 | Fodor et al. |
| 9,328,382 B2 | 5/2016 | Drmanac et al. |
| 9,347,059 B2 | 5/2016 | Saxonov |
| 9,388,465 B2 | 7/2016 | Hindson et al. |
| 9,410,201 B2 | 8/2016 | Hindson et al. |
| 9,567,631 B2 | 2/2017 | Hindson et al. |
| 9,574,226 B2 | 2/2017 | Gormley et al. |
| 9,637,799 B2 | 5/2017 | Fan et al. |
| 9,644,204 B2 | 5/2017 | Hindson et al. |
| 9,689,024 B2 | 6/2017 | Hindson et al. |
| 9,694,361 B2 | 7/2017 | Bharadwaj et al. |
| 9,695,468 B2 | 7/2017 | Hindson et al. |
| 9,701,998 B2 | 7/2017 | Hindson et al. |
| 9,856,530 B2 | 1/2018 | Hindson et al. |
| 9,951,386 B2 | 4/2018 | Hindson et al. |
| 9,957,558 B2 | 5/2018 | Leamon et al. |
| 1,001,187 A1 | 7/2018 | Belgrader et al. |
| 1,001,775 A1 | 7/2018 | Kaper et al. |
| 1,003,026 A1 | 7/2018 | Hindson et al. |
| 1,004,111 A1 | 8/2018 | Hindson et al. |
| 1,005,372 A1 | 8/2018 | Hindson et al. |
| 1,005,998 A1 | 8/2018 | Giresi et al. |
| 1,007,137 A1 | 9/2018 | Bharadwaj et al. |
| 1,013,744 A1 | 11/2018 | Bharadwaj et al. |
| 1,015,011 A1 | 12/2018 | Bharadwaj et al. |
| 1,015,096 A1 | 12/2018 | Hindson et al. |
| 1,015,099 A1 | 12/2018 | Giresi et al. |
| 1,020,834 A1 | 2/2019 | Hindson et al. |
| 1,022,143 A1 | 3/2019 | Hardenbol et al. |
| 1,022,144 A1 | 3/2019 | Hindson et al. |
| 1,022,764 A1 | 3/2019 | Hindson et al. |
| 2001/0020588 A1 | 9/2001 | Adourian et al. |
| 2001/0036669 A1 | 11/2001 | Jedrzejewski et al. |
| 2001/0041357 A1 | 11/2001 | Fouillet et al. |
| 2001/0044109 A1 | 11/2001 | Mandecki |
| 2001/0048900 A1 | 12/2001 | Bardell et al. |
| 2001/0053519 A1 | 12/2001 | Fodor et al. |
| 2002/0001856 A1 | 1/2002 | Chow et al. |
| 2002/0005354 A1 | 1/2002 | Spence et al. |
| 2002/0034737 A1 | 3/2002 | Drmanac |
| 2002/0043463 A1 | 4/2002 | Shenderov |
| 2002/0051971 A1 | 5/2002 | Stuelpnagel et al. |
| 2002/0051992 A1 | 5/2002 | Bridgham et al. |
| 2002/0058332 A1 | 5/2002 | Quake et al. |
| 2002/0065609 A1 | 5/2002 | Ashby et al. |
| 2002/0068278 A1 | 6/2002 | Giese et al. |
| 2002/0089100 A1 | 7/2002 | Kawasaki |
| 2002/0092767 A1 | 7/2002 | Bjornson et al. |
| 2002/0113009 A1 | 8/2002 | O'Connor et al. |
| 2002/0119455 A1 | 8/2002 | Chan et al. |
| 2002/0119536 A1 | 8/2002 | Stern |
| 2002/0131147 A1 | 9/2002 | Paolini et al. |
| 2002/0160518 A1 | 10/2002 | Hayenga et al. |
| 2002/0164820 A1 | 11/2002 | Brown |
| 2002/0166582 A1 | 11/2002 | O'Connor et al. |
| 2002/0172965 A1 | 11/2002 | Kamb et al. |
| 2002/0175079 A1 | 11/2002 | Christel et al. |
| 2002/0179849 A1 | 12/2002 | Maher et al. |
| 2003/0005967 A1 | 1/2003 | Karp |
| 2003/0007898 A1 | 1/2003 | Bohm et al. |
| 2003/0008285 A1 | 1/2003 | Fischer |
| 2003/0008323 A1 | 1/2003 | Ravkin et al. |
| 2003/0022231 A1 | 1/2003 | Wangh et al. |
| 2003/0027214 A1 | 2/2003 | Kamb |
| 2003/0027221 A1 | 2/2003 | Scott et al. |
| 2003/0028981 A1 | 2/2003 | Chandler et al. |
| 2003/0032141 A1 | 2/2003 | Nguyen et al. |
| 2003/0036206 A1 | 2/2003 | Chien et al. |
| 2003/0039978 A1 | 2/2003 | Hannah |
| 2003/0044777 A1 | 3/2003 | Beattie |
| 2003/0044836 A1 | 3/2003 | Levine et al. |
| 2003/0075446 A1 | 4/2003 | Culbertson et al. |
| 2003/0082587 A1 | 5/2003 | Seul et al. |
| 2003/0089605 A1 | 5/2003 | Timperman |
| 2003/0104466 A1 | 6/2003 | Knapp et al. |
| 2003/0108897 A1 | 6/2003 | Drmanac |
| 2003/0124509 A1 | 7/2003 | Kenis et al. |
| 2003/0149307 A1 | 8/2003 | Hai et al. |
| 2003/0170698 A1 | 9/2003 | Gascoyne et al. |
| 2003/0182068 A1 | 9/2003 | Battersby et al. |
| 2003/0207260 A1 | 11/2003 | Trnovsky et al. |
| 2003/0215862 A1 | 11/2003 | Parce et al. |
| 2004/0063138 A1 | 4/2004 | McGinnis et al. |
| 2004/0081962 A1 | 4/2004 | Chen et al. |
| 2004/0101680 A1 | 5/2004 | Barber et al. |
| 2004/0101880 A1 | 5/2004 | Rozwadowski et al. |
| 2004/0132122 A1 | 7/2004 | Banerjee et al. |
| 2004/0224331 A1 | 11/2004 | Cantor et al. |
| 2004/0258701 A1 | 12/2004 | Dominowski et al. |
| 2005/0019839 A1 | 1/2005 | Jespersen et al. |
| 2005/0042625 A1 | 2/2005 | Schmidt et al. |
| 2005/0079510 A1 | 4/2005 | Berka et al. |
| 2005/0130188 A1 | 6/2005 | Walt et al. |
| 2005/0172476 A1 | 8/2005 | Stone et al. |
| 2005/0181379 A1 | 8/2005 | Su et al. |
| 2005/0202429 A1 | 9/2005 | Trau et al. |
| 2005/0202489 A1 | 9/2005 | Cho et al. |
| 2005/0221339 A1 | 10/2005 | Griffiths et al. |
| 2005/0244850 A1 | 11/2005 | Huang et al. |
| 2005/0272159 A1 | 12/2005 | Ismagilov et al. |
| 2005/0287572 A1 | 12/2005 | Mathies et al. |

(56) References Cited

U.S. PATENT DOCUMENTS

| | | |
|---|---|---|
| 2006/0002890 A1 | 1/2006 | Hersel et al. |
| 2006/0008799 A1 | 1/2006 | Cai et al. |
| 2006/0020371 A1 | 1/2006 | Ham et al. |
| 2006/0040382 A1 | 2/2006 | Heffron et al. |
| 2006/0073487 A1 | 4/2006 | Oliver et al. |
| 2006/0078888 A1 | 4/2006 | Griffiths et al. |
| 2006/0153924 A1 | 7/2006 | Griffiths et al. |
| 2006/0163385 A1 | 7/2006 | Link et al. |
| 2006/0177832 A1 | 8/2006 | Brenner |
| 2006/0177833 A1 | 8/2006 | Brenner |
| 2006/0199193 A1 | 9/2006 | Koo et al. |
| 2006/0240506 A1 | 10/2006 | Kushmaro et al. |
| 2006/0257893 A1 | 11/2006 | Takahashi et al. |
| 2006/0263888 A1 | 11/2006 | Fritz et al. |
| 2006/0275782 A1 | 12/2006 | Gunderson et al. |
| 2006/0286570 A1 | 12/2006 | Rowlen et al. |
| 2006/0292583 A1 | 12/2006 | Schneider et al. |
| 2007/0003442 A1 | 1/2007 | Link et al. |
| 2007/0020617 A1 | 1/2007 | Trnovsky et al. |
| 2007/0020640 A1 | 1/2007 | McCloskey et al. |
| 2007/0026401 A1 | 2/2007 | Hofmann et al. |
| 2007/0031829 A1 | 2/2007 | Yasuno et al. |
| 2007/0042400 A1 | 2/2007 | Choi et al. |
| 2007/0042419 A1 | 2/2007 | Barany et al. |
| 2007/0054119 A1 | 3/2007 | Garstecki et al. |
| 2007/0072208 A1 | 3/2007 | Drmanac |
| 2007/0077572 A1 | 4/2007 | Tawfik et al. |
| 2007/0092914 A1 | 4/2007 | Griffiths et al. |
| 2007/0099208 A1 | 5/2007 | Drmanac et al. |
| 2007/0134277 A1 | 6/2007 | Chen et al. |
| 2007/0154903 A1 | 7/2007 | Marla et al. |
| 2007/0160503 A1 | 7/2007 | Sethu et al. |
| 2007/0172873 A1 | 7/2007 | Brenner et al. |
| 2007/0190543 A1 | 8/2007 | Livak |
| 2007/0195127 A1 | 8/2007 | Ahn et al. |
| 2007/0207060 A1 | 9/2007 | Zou et al. |
| 2007/0228588 A1 | 10/2007 | Noritomi et al. |
| 2007/0231823 A1 | 10/2007 | McKernan et al. |
| 2007/0238113 A1 | 10/2007 | Kanda et al. |
| 2007/0259357 A1 | 11/2007 | Brenner |
| 2007/0264320 A1 | 11/2007 | Lee et al. |
| 2008/0003142 A1 | 1/2008 | Link et al. |
| 2008/0004436 A1 | 1/2008 | Tawfik et al. |
| 2008/0014589 A1 | 1/2008 | Link et al. |
| 2008/0124726 A1 | 5/2008 | Monforte |
| 2008/0138878 A1 | 6/2008 | Kubu et al. |
| 2008/0213766 A1 | 9/2008 | Brown et al. |
| 2008/0228268 A1 | 9/2008 | Shannon et al. |
| 2008/0241820 A1 | 10/2008 | Krutzik et al. |
| 2008/0242560 A1 | 10/2008 | Gunderson et al. |
| 2008/0268450 A1 | 10/2008 | Nam et al. |
| 2009/0005252 A1 | 1/2009 | Drmanac et al. |
| 2009/0011943 A1 | 1/2009 | Drmanac et al. |
| 2009/0012187 A1 | 1/2009 | Chu et al. |
| 2009/0025277 A1 | 1/2009 | Takanashi |
| 2009/0035770 A1 | 2/2009 | Mathies et al. |
| 2009/0048124 A1 | 2/2009 | Leamon et al. |
| 2009/0053169 A1 | 2/2009 | Castillo et al. |
| 2009/0062129 A1 | 3/2009 | McKernan et al. |
| 2009/0068170 A1 | 3/2009 | Weitz et al. |
| 2009/0098555 A1 | 4/2009 | Roth et al. |
| 2009/0099041 A1 | 4/2009 | Church et al. |
| 2009/0105959 A1 | 4/2009 | Braverman et al. |
| 2009/0118488 A1 | 5/2009 | Drmanac et al. |
| 2009/0134027 A1 | 5/2009 | Jary |
| 2009/0137404 A1 | 5/2009 | Drmanac et al. |
| 2009/0137414 A1 | 5/2009 | Drmanac et al. |
| 2009/0143244 A1 | 6/2009 | Bridgham et al. |
| 2009/0148961 A1 | 6/2009 | Luchini et al. |
| 2009/0155780 A1 | 6/2009 | Xiao et al. |
| 2009/0155781 A1 | 6/2009 | Drmanac et al. |
| 2009/0197248 A1 | 8/2009 | Griffiths et al. |
| 2009/0197772 A1 | 8/2009 | Griffiths et al. |
| 2009/0202984 A1 | 8/2009 | Cantor |
| 2009/0203531 A1 | 8/2009 | Kurn |
| 2009/0264299 A1 | 10/2009 | Drmanac et al. |
| 2009/0286687 A1 | 11/2009 | Dressman et al. |
| 2009/0325260 A1 | 12/2009 | Otto et al. |
| 2010/0021973 A1 | 1/2010 | Makarov et al. |
| 2010/0021984 A1 | 1/2010 | Edd et al. |
| 2010/0022414 A1 | 1/2010 | Link et al. |
| 2010/0035254 A1 | 2/2010 | Williams |
| 2010/0062494 A1 | 3/2010 | Church et al. |
| 2010/0069263 A1 | 3/2010 | Shendure et al. |
| 2010/0086914 A1 | 4/2010 | Bentley et al. |
| 2010/0105112 A1 | 4/2010 | Holtze et al. |
| 2010/0113296 A1 | 5/2010 | Myerson |
| 2010/0120098 A1 | 5/2010 | Grunenwald et al. |
| 2010/0130369 A1 | 5/2010 | Shenderov et al. |
| 2010/0136544 A1 | 6/2010 | Agresti et al. |
| 2010/0137163 A1 | 6/2010 | Link et al. |
| 2010/0173394 A1 | 7/2010 | Colston, Jr. et al. |
| 2010/0187705 A1 | 7/2010 | Lee et al. |
| 2010/0210479 A1 | 8/2010 | Griffiths et al. |
| 2010/0216153 A1 | 8/2010 | Lapidus et al. |
| 2010/0248237 A1 | 9/2010 | Froehlich et al. |
| 2010/0248991 A1 | 9/2010 | Roesler et al. |
| 2010/0304982 A1 | 12/2010 | Hinz et al. |
| 2011/0000560 A1 | 1/2011 | Miller et al. |
| 2011/0008775 A1 | 1/2011 | Gao et al. |
| 2011/0028412 A1 | 2/2011 | Cappello et al. |
| 2011/0033548 A1 | 2/2011 | Lai et al. |
| 2011/0033854 A1 | 2/2011 | Drmanac et al. |
| 2011/0053798 A1 | 3/2011 | Hindson et al. |
| 2011/0059556 A1 | 3/2011 | Strey et al. |
| 2011/0071053 A1 | 3/2011 | Drmanac et al. |
| 2011/0086780 A1 | 4/2011 | Colston, Jr. et al. |
| 2011/0092376 A1 | 4/2011 | Colston, Jr. et al. |
| 2011/0092392 A1 | 4/2011 | Colston, Jr. et al. |
| 2011/0160078 A1 | 6/2011 | Fodor et al. |
| 2011/0166034 A1 | 7/2011 | Kwong et al. |
| 2011/0195496 A1 | 8/2011 | Muraguchi et al. |
| 2011/0201526 A1 | 8/2011 | Berka et al. |
| 2011/0212090 A1 | 9/2011 | Pedersen et al. |
| 2011/0217736 A1 | 9/2011 | Hindson |
| 2011/0218123 A1 | 9/2011 | Weitz et al. |
| 2011/0263457 A1 | 10/2011 | Krutzik et al. |
| 2011/0267457 A1 | 11/2011 | Weitz et al. |
| 2011/0281736 A1 | 11/2011 | Drmanac et al. |
| 2011/0281738 A1 | 11/2011 | Drmanac et al. |
| 2011/0287435 A1 | 11/2011 | Grunenwald et al. |
| 2011/0305761 A1 | 12/2011 | Shum et al. |
| 2011/0306141 A1 | 12/2011 | Bronchetti et al. |
| 2011/0319281 A1 | 12/2011 | Drmanac |
| 2012/0000777 A1 | 1/2012 | Garrell et al. |
| 2012/0003657 A1 | 1/2012 | Myllykangas et al. |
| 2012/0010091 A1 | 1/2012 | Linnarson et al. |
| 2012/0010098 A1 | 1/2012 | Griffiths et al. |
| 2012/0010107 A1 | 1/2012 | Griffiths et al. |
| 2012/0014977 A1 | 1/2012 | Furihata et al. |
| 2012/0015382 A1 | 1/2012 | Weitz et al. |
| 2012/0015822 A1 | 1/2012 | Weitz et al. |
| 2012/0071331 A1 | 3/2012 | Casbon et al. |
| 2012/0121481 A1 | 5/2012 | Romanowsky et al. |
| 2012/0132288 A1 | 5/2012 | Weitz et al. |
| 2012/0135893 A1 | 5/2012 | Drmanac et al. |
| 2012/0165219 A1 | 6/2012 | Van Der Zaag et al. |
| 2012/0172259 A1 | 7/2012 | Rigatti et al. |
| 2012/0184449 A1 | 7/2012 | Hixson et al. |
| 2012/0190032 A1 | 7/2012 | Ness et al. |
| 2012/0190037 A1 | 7/2012 | Durin et al. |
| 2012/0196288 A1 | 8/2012 | Beer et al. |
| 2012/0208705 A1 | 8/2012 | Steemers et al. |
| 2012/0208724 A1 | 8/2012 | Steemers et al. |
| 2012/0211084 A1 | 8/2012 | Weitz et al. |
| 2012/0220494 A1 | 8/2012 | Samuels et al. |
| 2012/0220497 A1 | 8/2012 | Jacobson et al. |
| 2012/0222748 A1 | 9/2012 | Weitz et al. |
| 2012/0231972 A1 | 9/2012 | Golyshin et al. |
| 2012/0252012 A1 | 10/2012 | Armougom et al. |
| 2012/0253689 A1 | 10/2012 | Rogan et al. |
| 2012/0297493 A1 | 11/2012 | Cooper et al. |
| 2012/0309002 A1 | 12/2012 | Link |
| 2012/0316074 A1 | 12/2012 | Saxonov et al. |

(56) References Cited

U.S. PATENT DOCUMENTS

| | | |
|---|---|---|
| 2013/0017978 A1 | 1/2013 | Kavanagh et al. |
| 2013/0018970 A1 | 1/2013 | Woundy et al. |
| 2013/0022682 A1 | 1/2013 | Lee et al. |
| 2013/0028812 A1 | 1/2013 | Prieto et al. |
| 2013/0041004 A1 | 2/2013 | Drager et al. |
| 2013/0046030 A1 | 2/2013 | Rotem et al. |
| 2013/0059310 A1 | 3/2013 | Brenner et al. |
| 2013/0078638 A1 | 3/2013 | Berka et al. |
| 2013/0079231 A1 | 3/2013 | Pushkarev et al. |
| 2013/0079251 A1 | 3/2013 | Boles |
| 2013/0084243 A1 | 4/2013 | Goetsch et al. |
| 2013/0096073 A1 | 4/2013 | Sidelman |
| 2013/0109575 A1 | 5/2013 | Kleinschmidt et al. |
| 2013/0109576 A1 | 5/2013 | Shuber et al. |
| 2013/0121893 A1 | 5/2013 | Delamarche et al. |
| 2013/0130919 A1 | 5/2013 | Chen et al. |
| 2013/0157870 A1 | 6/2013 | Pushkarev et al. |
| 2013/0157899 A1 | 6/2013 | Adler, Jr. et al. |
| 2013/0178368 A1 | 7/2013 | Griffiths et al. |
| 2013/0189700 A1 | 7/2013 | So et al. |
| 2013/0203605 A1 | 8/2013 | Shendure et al. |
| 2013/0203675 A1 | 8/2013 | Desimone et al. |
| 2013/0210639 A1 | 8/2013 | Link et al. |
| 2013/0210991 A1 | 8/2013 | Fonnum et al. |
| 2013/0211055 A1 | 8/2013 | Raines et al. |
| 2013/0225418 A1 | 8/2013 | Watson |
| 2013/0225623 A1 | 8/2013 | Buxbaum |
| 2013/0273640 A1 | 10/2013 | Krishnan et al. |
| 2013/0274117 A1 | 10/2013 | Church et al. |
| 2013/0296173 A1 | 11/2013 | Callow et al. |
| 2013/0343317 A1 | 12/2013 | Etemad et al. |
| 2013/0344508 A1* | 12/2013 | Schwartz ............ G01N 33/5306 435/7.21 |
| 2014/0030350 A1 | 1/2014 | Ashrafi et al. |
| 2014/0038178 A1 | 2/2014 | Otto et al. |
| 2014/0057799 A1 | 2/2014 | Johnson et al. |
| 2014/0065234 A1 | 3/2014 | Shum et al. |
| 2014/0093916 A1 | 4/2014 | Belyaev et al. |
| 2014/0120529 A1 | 5/2014 | Andersen et al. |
| 2014/0155274 A1 | 6/2014 | Xie et al. |
| 2014/0155295 A1 | 6/2014 | Hindson et al. |
| 2014/0194323 A1 | 7/2014 | Gillevet et al. |
| 2014/0199730 A1 | 7/2014 | Agresti et al. |
| 2014/0199731 A1 | 7/2014 | Agresti et al. |
| 2014/0206554 A1 | 7/2014 | Hindson et al. |
| 2014/0227684 A1 | 8/2014 | Hindson et al. |
| 2014/0227706 A1 | 8/2014 | Kato et al. |
| 2014/0228255 A1 | 8/2014 | Hindson et al. |
| 2014/0235506 A1 | 8/2014 | Hindson et al. |
| 2014/0242664 A1 | 8/2014 | Zhang et al. |
| 2014/0274740 A1 | 9/2014 | Srinivasan et al. |
| 2014/0287963 A1 | 9/2014 | Hindson et al. |
| 2014/0302503 A1 | 10/2014 | Lowe et al. |
| 2014/0315725 A1 | 10/2014 | Faham et al. |
| 2014/0315755 A1 | 10/2014 | Chen et al. |
| 2014/0357500 A1 | 12/2014 | Vigneault et al. |
| 2014/0378322 A1 | 12/2014 | Hindson et al. |
| 2014/0378345 A1 | 12/2014 | Hindson et al. |
| 2014/0378349 A1 | 12/2014 | Hindson et al. |
| 2015/0005188 A1 | 1/2015 | Levner et al. |
| 2015/0005199 A1 | 1/2015 | Hindson et al. |
| 2015/0005200 A1 | 1/2015 | Hindson et al. |
| 2015/0011430 A1 | 1/2015 | Saxonov |
| 2015/0011432 A1 | 1/2015 | Saxonov et al. |
| 2015/0031037 A1 | 1/2015 | Li et al. |
| 2015/0057163 A1 | 2/2015 | Rotem et al. |
| 2015/0072899 A1 | 3/2015 | Ward et al. |
| 2015/0111256 A1 | 4/2015 | Church et al. |
| 2015/0111788 A1 | 4/2015 | Fernandez et al. |
| 2015/0119280 A1 | 4/2015 | Srinivas et al. |
| 2015/0211056 A1 | 7/2015 | Um et al. |
| 2015/0218633 A1 | 8/2015 | Hindson et al. |
| 2015/0224466 A1 | 8/2015 | Hindson et al. |
| 2015/0225777 A1 | 8/2015 | Hindson et al. |
| 2015/0247182 A1 | 9/2015 | Faham et al. |
| 2015/0259736 A1 | 9/2015 | Steemers et al. |
| 2015/0267191 A1 | 9/2015 | Steelman et al. |
| 2015/0291942 A1 | 10/2015 | Gloeckner et al. |
| 2015/0298091 A1 | 10/2015 | Weitz et al. |
| 2015/0299772 A1 | 10/2015 | Zhang |
| 2015/0299784 A1 | 10/2015 | Fan et al. |
| 2015/0329617 A1 | 11/2015 | Winther et al. |
| 2015/0329852 A1 | 11/2015 | Nolan et al. |
| 2015/0329891 A1 | 11/2015 | Tan et al. |
| 2015/0337298 A1 | 11/2015 | Xi et al. |
| 2015/0353999 A1 | 12/2015 | Agresti et al. |
| 2015/0361418 A1 | 12/2015 | Reed et al. |
| 2015/0368638 A1 | 12/2015 | Steemers et al. |
| 2015/0368694 A1 | 12/2015 | Pan et al. |
| 2015/0376605 A1 | 12/2015 | Jarosz et al. |
| 2015/0376608 A1 | 12/2015 | Kaper et al. |
| 2015/0376609 A1 | 12/2015 | Hindson et al. |
| 2015/0376700 A1 | 12/2015 | Schnall-Levin et al. |
| 2015/0379196 A1 | 12/2015 | Schnall-Levin et al. |
| 2016/0024558 A1 | 1/2016 | Hardenbol |
| 2016/0025726 A1 | 1/2016 | Altin et al. |
| 2016/0032282 A1 | 2/2016 | Vigneault et al. |
| 2016/0053253 A1 | 2/2016 | Salathia et al. |
| 2016/0060621 A1 | 3/2016 | Agresti et al. |
| 2016/0115474 A1 | 4/2016 | Jelinek et al. |
| 2016/0122753 A1 | 5/2016 | Mikkelsen et al. |
| 2016/0122817 A1 | 5/2016 | Jarosz et al. |
| 2016/0145683 A1 | 5/2016 | Fan et al. |
| 2016/0153005 A1 | 6/2016 | Zhang et al. |
| 2016/0160235 A1 | 6/2016 | Solodushko et al. |
| 2016/0177359 A1 | 6/2016 | Ukanis et al. |
| 2016/0201125 A1 | 7/2016 | Samuels et al. |
| 2016/0208323 A1 | 7/2016 | Bernstein et al. |
| 2016/0231324 A1 | 8/2016 | Zhao et al. |
| 2016/0244742 A1 | 8/2016 | Linnarsson et al. |
| 2016/0244809 A1 | 8/2016 | Belgrader et al. |
| 2016/0244825 A1 | 8/2016 | Vigneault et al. |
| 2016/0251697 A1 | 9/2016 | Nolan et al. |
| 2016/0257984 A1 | 9/2016 | Hardenbol et al. |
| 2016/0281160 A1 | 9/2016 | Jarosz et al. |
| 2016/0289769 A1 | 10/2016 | Schwartz et al. |
| 2016/0304860 A1 | 10/2016 | Hindson et al. |
| 2016/0326583 A1 | 11/2016 | Johnson et al. |
| 2016/0348093 A1 | 12/2016 | Price et al. |
| 2016/0376663 A1 | 12/2016 | Brown |
| 2017/0009274 A1 | 1/2017 | Abate et al. |
| 2017/0016041 A1 | 1/2017 | Greenfield et al. |
| 2017/0114390 A1 | 4/2017 | Hindson et al. |
| 2017/0145476 A1 | 5/2017 | Ryvkin et al. |
| 2017/0183701 A1 | 6/2017 | Agresti et al. |
| 2017/0260584 A1 | 9/2017 | Zheng et al. |
| 2017/0268056 A1 | 9/2017 | Vigneault et al. |
| 2017/0321252 A1 | 11/2017 | Hindson et al. |
| 2017/0343545 A1 | 11/2017 | Hadrup et al. |
| 2017/0348691 A1 | 12/2017 | Bharadwaj et al. |
| 2017/0356027 A1 | 12/2017 | Hindson et al. |
| 2018/0008984 A1 | 1/2018 | Bharadwaj et al. |
| 2018/0015472 A1 | 1/2018 | Bharadwaj et al. |
| 2018/0016634 A1 | 1/2018 | Hindson et al. |
| 2018/0030512 A1 | 2/2018 | Hindson et al. |
| 2018/0030515 A1 | 2/2018 | Regev et al. |
| 2018/0051321 A1 | 2/2018 | Hindson et al. |
| 2018/0057868 A1 | 3/2018 | Walder et al. |
| 2018/0080021 A1 | 3/2018 | Reuter et al. |
| 2018/0087050 A1 | 3/2018 | Zheng et al. |
| 2018/0088112 A1 | 3/2018 | Fan et al. |
| 2018/0094298 A1 | 4/2018 | Hindson et al. |
| 2018/0094313 A1 | 4/2018 | Hindson |
| 2018/0094315 A1 | 4/2018 | Hindson et al. |
| 2018/0105808 A1 | 4/2018 | Mikkelsen et al. |
| 2018/0112253 A1 | 4/2018 | Hindson et al. |
| 2018/0112266 A1 | 4/2018 | Hindson et al. |
| 2018/0179580 A1 | 6/2018 | Hindson et al. |
| 2018/0179591 A1 | 6/2018 | Belgrader et al. |
| 2018/0180601 A1 | 6/2018 | Pedersen et al. |
| 2018/0195060 A1 | 7/2018 | Wang et al. |
| 2018/0195112 A1 | 7/2018 | Lebofsky et al. |
| 2018/0216162 A1 | 8/2018 | Belhocine et al. |
| 2018/0237951 A1 | 8/2018 | Bock et al. |

(56) References Cited

U.S. PATENT DOCUMENTS

| | | |
|---|---|---|
| 2018/0258466 A1 | 9/2018 | Hindson et al. |
| 2018/0258482 A1 | 9/2018 | Hindson et al. |
| 2018/0265928 A1 | 9/2018 | Schnall-Levin et al. |
| 2018/0267036 A1 | 9/2018 | Fan et al. |
| 2018/0273933 A1 | 9/2018 | Gunderson et al. |
| 2018/0274027 A1 | 9/2018 | Hindson et al. |
| 2018/0282804 A1 | 10/2018 | Hindson et al. |
| 2018/0305685 A1 | 10/2018 | Li et al. |
| 2018/0327839 A1 | 11/2018 | Hindson et al. |
| 2018/0340169 A1 | 11/2018 | Belhocine et al. |
| 2018/0340170 A1 | 11/2018 | Belhocine et al. |
| 2018/0340171 A1 | 11/2018 | Belhocine et al. |
| 2018/0340172 A1 | 11/2018 | Belhocine et al. |
| 2018/0340939 A1 | 11/2018 | Gaublomme et al. |
| 2018/0346979 A1 | 12/2018 | Hindson et al. |
| 2018/0363029 A1 | 12/2018 | Hindson et al. |
| 2018/0371538 A1 | 12/2018 | Blauwkamp et al. |
| 2018/0371540 A1 | 12/2018 | Hindson et al. |
| 2019/0002967 A1 | 1/2019 | Chen et al. |
| 2019/0024166 A1 | 1/2019 | Hindson et al. |
| 2019/0032129 A1 | 1/2019 | Hindson et al. |
| 2019/0032130 A1 | 1/2019 | Giresi et al. |
| 2019/0040382 A1 | 2/2019 | Steemers et al. |
| 2019/0040464 A1 | 2/2019 | Giresi et al. |
| 2019/0078150 A1 | 3/2019 | Chen et al. |
| 2019/0085391 A1 | 3/2019 | Hindson et al. |

FOREIGN PATENT DOCUMENTS

| | | |
|---|---|---|
| EP | 0249007 A2 | 12/1987 |
| EP | 0271281 A2 | 6/1988 |
| EP | 0637996 B1 | 7/1997 |
| EP | 1019496 B1 | 9/2004 |
| EP | 1672064 A1 | 6/2006 |
| EP | 1482036 B1 | 10/2007 |
| EP | 1841879 A2 | 10/2007 |
| EP | 1944368 A1 | 7/2008 |
| EP | 1594980 B1 | 11/2009 |
| EP | 1967592 B1 | 4/2010 |
| EP | 2258846 A2 | 12/2010 |
| EP | 2145955 B1 | 2/2012 |
| EP | 1905828 B1 | 8/2012 |
| EP | 2136786 B1 | 10/2012 |
| EP | 1908832 B1 | 12/2012 |
| EP | 2540389 A1 | 1/2013 |
| EP | 2635679 A1 | 9/2013 |
| EP | 2752664 A1 | 7/2014 |
| GB | 2097692 B | 5/1985 |
| GB | 2485850 A | 5/2012 |
| JP | S5949832 A | 3/1984 |
| JP | S60227826 A | 11/1985 |
| JP | 2006507921 A | 3/2006 |
| JP | 2006289250 A | 10/2006 |
| JP | 2007015990 A | 1/2007 |
| JP | 2007268350 A | 10/2007 |
| JP | 2009513948 A | 4/2009 |
| JP | 2009208074 A | 9/2009 |
| JP | 2012131798 A | 7/2012 |
| JP | 2012522517 A | 9/2012 |
| WO | WO-8402000 A1 | 5/1984 |
| WO | WO-9301498 A1 | 1/1993 |
| WO | WO-9418218 A1 | 8/1994 |
| WO | WO-9419101 A1 | 9/1994 |
| WO | WO-9423699 A1 | 10/1994 |
| WO | WO-9530782 A1 | 11/1995 |
| WO | WO-9629629 A2 | 9/1996 |
| WO | WO-9641011 A1 | 12/1996 |
| WO | WO-9802237 A1 | 1/1998 |
| WO | WO-9852691 A1 | 11/1998 |
| WO | WO-9909217 A1 | 2/1999 |
| WO | WO-9942597 A1 | 8/1999 |
| WO | WO-9952708 A1 | 10/1999 |
| WO | WO-0008212 A1 | 2/2000 |
| WO | WO-0023181 A1 | 4/2000 |
| WO | WO-0026412 A1 | 5/2000 |
| WO | WO-0034527 A2 | 6/2000 |
| WO | WO-0043766 A1 | 7/2000 |
| WO | WO-0070095 A2 | 11/2000 |
| WO | WO-0102850 A1 | 1/2001 |
| WO | WO-0114589 A2 | 3/2001 |
| WO | WO-0189787 A2 | 11/2001 |
| WO | WO-0190418 A1 | 11/2001 |
| WO | WO-0127610 A3 | 3/2002 |
| WO | WO-0231203 A2 | 4/2002 |
| WO | WO-02086148 A1 | 10/2002 |
| WO | WO-0218949 A3 | 1/2003 |
| WO | WO-03062462 A2 | 7/2003 |
| WO | WO-2004002627 A2 | 1/2004 |
| WO | WO-2004010106 A2 | 1/2004 |
| WO | WO-2004061083 A2 | 7/2004 |
| WO | WO-2004065617 A2 | 8/2004 |
| WO | WO-2004069849 A2 | 8/2004 |
| WO | WO-2004091763 A2 | 10/2004 |
| WO | WO-2004102204 A1 | 11/2004 |
| WO | WO-2004103565 A2 | 12/2004 |
| WO | WO-2004105734 A1 | 12/2004 |
| WO | WO-2005002730 A1 | 1/2005 |
| WO | WO-2005021151 A1 | 3/2005 |
| WO | WO-2005023331 A2 | 3/2005 |
| WO | WO-2005040406 A1 | 5/2005 |
| WO | WO-2005049787 A2 | 6/2005 |
| WO | WO-2005082098 A2 | 9/2005 |
| WO | WO-2006030993 A1 | 3/2006 |
| WO | WO-2006071770 A2 | 7/2006 |
| WO | WO-2006078841 A1 | 7/2006 |
| WO | WO-2006096571 A2 | 9/2006 |
| WO | WO-2007001448 A2 | 1/2007 |
| WO | WO-2007002490 A2 | 1/2007 |
| WO | WO-2007012638 A1 | 2/2007 |
| WO | WO-2007018601 A1 | 2/2007 |
| WO | WO-2007024840 A2 | 3/2007 |
| WO | WO-2007081385 A2 | 7/2007 |
| WO | WO-2007081387 A1 | 7/2007 |
| WO | WO-2007084192 A2 | 7/2007 |
| WO | WO-2007089541 A2 | 8/2007 |
| WO | WO-2007093819 A2 | 8/2007 |
| WO | WO-2007111937 A1 | 10/2007 |
| WO | WO-2007114794 A1 | 10/2007 |
| WO | WO-2007121489 A2 | 10/2007 |
| WO | WO-2007133710 A2 | 11/2007 |
| WO | WO-2007138178 A2 | 12/2007 |
| WO | WO-2007139766 A2 | 12/2007 |
| WO | WO-2007140015 A2 | 12/2007 |
| WO | WO-2007147079 A2 | 12/2007 |
| WO | WO-2007149432 A2 | 12/2007 |
| WO | WO-2008021123 A1 | 2/2008 |
| WO | WO-2008091792 A2 | 7/2008 |
| WO | WO-2008102057 A1 | 8/2008 |
| WO | WO-2008109176 A2 | 9/2008 |
| WO | WO-2008121342 A2 | 10/2008 |
| WO | WO-2008061193 A3 | 11/2008 |
| WO | WO-2008134153 A1 | 11/2008 |
| WO | WO-2008150432 A1 | 12/2008 |
| WO | WO-2009005680 A1 | 1/2009 |
| WO | WO-2009011808 A1 | 1/2009 |
| WO | WO-2009015296 A1 | 1/2009 |
| WO | WO-2009048532 A2 | 4/2009 |
| WO | WO-2009061372 A1 | 5/2009 |
| WO | WO-2009085215 A1 | 7/2009 |
| WO | WO-2009147386 A1 | 12/2009 |
| WO | WO-2010004018 A2 | 1/2010 |
| WO | WO-2010009735 A1 | 1/2010 |
| WO | WO-2010033200 A2 | 3/2010 |
| WO | WO-2010048605 A1 | 4/2010 |
| WO | WO-2010104604 A1 | 9/2010 |
| WO | WO-2010115154 A1 | 10/2010 |
| WO | WO-2010148039 A2 | 12/2010 |
| WO | WO-2010151776 A2 | 12/2010 |
| WO | WO-2010117620 A3 | 2/2011 |
| WO | WO-2011028539 A1 | 3/2011 |
| WO | WO-2011047870 A1 | 4/2011 |
| WO | WO-2011056546 A1 | 5/2011 |
| WO | WO-2011066476 A1 | 6/2011 |
| WO | WO-2011074960 A1 | 6/2011 |

(56) References Cited

FOREIGN PATENT DOCUMENTS

| | | |
|---|---|---|
| WO | WO-2011106314 A2 | 9/2011 |
| WO | WO-2011140627 A1 | 11/2011 |
| WO | WO-2011156529 A2 | 12/2011 |
| WO | WO-2012012037 A1 | 1/2012 |
| WO | WO-2011140510 A3 | 3/2012 |
| WO | WO-2012047889 A2 | 4/2012 |
| WO | WO-2012048340 A2 | 4/2012 |
| WO | WO-2012048341 A1 | 4/2012 |
| WO | WO-2012061832 A1 | 5/2012 |
| WO | WO-2012083225 A2 | 6/2012 |
| WO | WO-2012087736 A1 | 6/2012 |
| WO | WO-2012106546 A2 | 8/2012 |
| WO | WO-2012112804 A1 | 8/2012 |
| WO | WO-2012112970 A2 | 8/2012 |
| WO | WO-2012136734 A1 | 10/2012 |
| WO | WO-2012142611 A2 | 10/2012 |
| WO | WO-2012148497 A2 | 11/2012 |
| WO | WO-2012149042 A2 | 11/2012 |
| WO | WO-2012150317 A1 | 11/2012 |
| WO | WO-2012166425 A2 | 12/2012 |
| WO | WO-2013019751 A1 | 2/2013 |
| WO | WO-2013036929 A1 | 3/2013 |
| WO | WO-2013055955 A1 | 4/2013 |
| WO | WO-2013096643 A1 | 6/2013 |
| WO | WO-2013122996 A1 | 8/2013 |
| WO | WO-2013123125 A1 | 8/2013 |
| WO | WO-2013126741 A1 | 8/2013 |
| WO | WO-2013134261 A1 | 9/2013 |
| WO | WO-2013150083 A1 | 10/2013 |
| WO | WO-2013177220 A1 | 11/2013 |
| WO | WO-2013188872 A1 | 12/2013 |
| WO | WO-2014018460 A1 | 1/2014 |
| WO | WO-2014028537 A1 | 2/2014 |
| WO | WO-2014053854 A1 | 4/2014 |
| WO | WO-2014071361 A1 | 5/2014 |
| WO | WO-2014072703 A1 | 5/2014 |
| WO | WO-2014074611 A1 | 5/2014 |
| WO | WO-2014093676 A1 | 6/2014 |
| WO | WO-2014108810 A2 | 7/2014 |
| WO | WO-2014140309 A1 | 9/2014 |
| WO | WO-2014144495 A1 | 9/2014 |
| WO | WO-2014145047 A1 | 9/2014 |
| WO | WO-2014150931 A1 | 9/2014 |
| WO | WO-2014182835 A1 | 11/2014 |
| WO | WO-2014189957 A2 | 11/2014 |
| WO | WO-2014200767 A1 | 12/2014 |
| WO | WO-2014210353 A2 | 12/2014 |
| WO | WO-2015031691 A1 | 3/2015 |
| WO | WO-2015044428 A1 | 4/2015 |
| WO | WO-2015164212 A1 | 10/2015 |
| WO | WO-2015185067 A1 | 12/2015 |
| WO | WO-2015188839 A2 | 12/2015 |
| WO | WO-2016040476 A1 | 3/2016 |
| WO | WO-2016033251 A3 | 4/2016 |
| WO | WO-2016061517 A2 | 4/2016 |
| WO | WO-2016100976 A2 | 6/2016 |
| WO | WO-2016126871 A2 | 8/2016 |
| WO | WO-2016138496 A1 | 9/2016 |
| WO | WO-2016149661 A1 | 9/2016 |
| WO | WO-2016187717 A1 | 12/2016 |
| WO | WO-2016191618 A1 | 12/2016 |
| WO | WO-2016207647 A1 | 12/2016 |
| WO | WO-2016207653 A1 | 12/2016 |
| WO | WO-2016207661 A1 | 12/2016 |
| WO | WO-2017015075 A1 | 1/2017 |
| WO | WO-2017025594 A1 | 2/2017 |
| WO | WO-2017034970 A1 | 3/2017 |
| WO | WO-2017053905 A1 | 3/2017 |
| WO | WO-2017075265 A1 | 5/2017 |
| WO | WO-2017075294 A1 | 5/2017 |
| WO | WO-2017079593 A1 | 5/2017 |
| WO | WO-2017096158 A1 | 6/2017 |
| WO | WO-2017117358 A1 | 7/2017 |
| WO | WO-2017156336 A1 | 9/2017 |
| WO | WO-2018031631 A1 | 2/2018 |
| WO | WO-2018039969 A1 | 3/2018 |
| WO | WO-2018045186 A1 | 3/2018 |
| WO | WO-2018058073 A2 | 3/2018 |
| WO | WO-2018103025 A1 | 6/2018 |
| WO | WO-2018119301 A1 | 6/2018 |
| WO | WO-2018119447 A2 | 6/2018 |
| WO | WO-2018125982 A1 | 7/2018 |
| WO | WO-2018129368 A2 | 7/2018 |
| WO | WO-2018132635 A1 | 7/2018 |
| WO | WO-2018172726 A1 | 9/2018 |
| WO | WO-2018174827 A1 | 9/2018 |
| WO | WO-2018191701 A1 | 10/2018 |
| WO | WO-2019028166 A1 | 2/2019 |

OTHER PUBLICATIONS

Epicenter, EZ-Tn5 Transposase, Epicenter, 2012, 1-5. (Year: 2012).

10X Genomics. 10x Genomics Chromium™ Single Cell 3' Solution Utilized for Perturb-seq Approach. Press Release. Dec. 19, 2016. Retrieved from https://www.10xgenomics.com/news/10x-genomics-chromium-single-cell-3-solution-utilized-perturb-seq-approach/.

Abate, et al. Beating Poisson encapsulation statistics using close-packed ordering. Lab Chip. Sep. 21, 2009;9(18):2628-31. doi: 10.1039/b909386a. Epub Jul. 28, 2009.

Abate, et al. High-throughput injection with microfluidics using picoinjectors. Proc Natl Acad Sci U S A. Nov. 9, 2010;107(45):19163-6. doi: 10.1073/pNas.1006888107. Epub Oct. 20, 2010.

Abate et al., Valve-based flow focusing for drop formation. Appl Phys Lett. 2009;94. 3 pages.

Adamson, et al. A Multiplexed Single-Cell CRISPR Screening Platform Enables Systematic Dissection of the Unfolded Protein Response. Cell. Dec. 15, 2016 15;167(7):1867-1882.e21. doi: 10.1016/j.cell.2016.11.048.

Adamson et al., "Production of arrays of chemically distinct nanolitre plugs via repeated splitting in microfluidic devices", Lab Chip 6(9): 1178-1186 (Sep. 2006).

Adey, et al. Rapid, low-input, low-bias construction of shotgun fragment libraries by high-density in vitro transposition. Genome Biology 11:R119 (2010).

Adey, et al., "Ultra-low-input, tagmentation-based whole-genome bisulfite sequencing", Genome Research, 2012, 22 ;6): 1139-1143.

Agasti, et al. Photocleavable DNA barcode-antibody conjugates allow sensitive and multiplexed protein analysis in single cells. J Amer Chem Soc ePub, Nov. 2, 2012, vol. 134, No. 45, pp. 18499-18502.

Agresti, et al. Selection of ribozymes that catalyse multiple-turnover Diels-Alder cycloadditions by using in vitro compartmentalization. Proc Natl Acad Sci U S A. Nov. 8, 2005;102(45):16170-5. Epub Oct. 31, 2005.

Ahern, "Biochemical, Reagents Kits Offer Scientists Good Return on Investment" The Scientist (1995) 9(15):1-7.

Aitman, et al. Number polymorphism in Fcgr3 predisposes to glomerulonephritis in rats and humans. Nature. Feb. 16, 2006;439(7078):851-5.

Akselband, "Enrichment of slow-growing marine microorganisms from mixed cultures using gel microdrop (GMD) growth assay and fluorescence-activated cell sorting", J. Exp. Marine Bioi., 329: 196-205 (2006).

Akselband, "Rapid mycobacteria drug susceptibility testing using gel microdrop (GMD) growth assay and flow cytometry", J. Microbiol. Methods, 62:181-197 (2005).

Altemos et al., "Genomic Characterization of Large Heterochromatic Gaps in the Human Genome Assembly," PLOS Computational Biology, May 15, 2014, vol. 10, Issue 5, 14 pages.

Amini, S. et al. "Haplotype-resolved whole-genome sequencing by contiguity-preserving transposition and combinatorial indexing" Nature Genetics (2014) 46:1343-1349 doi:10.1038/ng.3119.

Anna, S.L., et al., "Formation of dispersions using "flow focusing" in microchannels," Applied Physics Letters, vol. 82, No. 3, pp. 364-366 (2003).

Anonymous, "Oligo(dT)25 cellulose beads" NEB (2012) Retrieved from the Internet:https://www.neb.com/~/media/Catalog/All-Products/

(56) References Cited

OTHER PUBLICATIONS

286CA51268E24DE1B06F1CB2886981354/Datacards%20or%Manuals/S1408Datasheet-Lot0011205.pdf.
Anonymous, "Oligotex Handbook" Qiagen (2012) XP055314680, Retrieved from the Internet: URL:http://www.qiagen.com/de/resources/download.apsx?id=f9fa1d98-d54d-47e7-a20b-8b0cb8975009&lang=en.
Anonymous: "TCEP=HCI" Thermo Scientific, Dec. 31, 2013 (Dec. 31, 2013), XP055508461, Retrieved from the Internet: URL:https://assets.thermofisher.com/TFS-Assets/LSG/manuals/MAN0011306_TCEP_HCI_UG.pdf.
Anonymous: "Three Ways to Get Intimate with Epigenetic Marks". Oct. 24, 2012. Retrieved from Internet: https://epigenie.com/three-ways-to-get-intimate-with-epigenetic-marks/.
Anonymous: "Viscosity-Basic concepts" (2004) XP055314117, Retrieved from the Internet: URL:http://lhtc.epfl.ch/webdav/site/lhtc/shared/import/migration/2 VISCOSITY. pdf.
Ason et al. DNA sequence bias during Tn5 transposition. Journal of molecular biology 335.5 (2004): 1213-1225.
Attia, et al. Micro-injection moulding of polymer microfluidic devices. Microfluidics and nanofluidics. 2009; 7(1):1-28.
Balikova, et al. Autosomal-dominant microtia linked to five tandem copies of a copy-number-variable region at chromosome 4p16. Am J Hum Genet. Jan. 2008;82(1):181-7. doi: 10.1016/j.ajhg.2007.08.001.
Banchelli, et al. Phospholipid membranes decorated by cholesterol-based oligonucleotides as soft hybrid nanostructures. J Phys Chem B. Sep. 4, 2008;112(35):10942-52. doi: 10.1021/jp802415t. Epub Aug. 9, 2008.
Baret, et al. Fluorescence-activated droplet sorting (FADS): efficient microfluidic cell sorting based on enzymatic activity. Lab Chip. Jul. 7, 2009;9(13):1850-8. doi: 10.1039/b902504a. Epub Apr. 23, 2009.
BD. BD Rhapsody™ Single-Cell Analysis System: Analyze hundreds of genes across tens of thousands of single cells in parallel. BD, Becton, Dickinson and Company. BDGM1012 Rev. Jan. 2017. 8 pages.
Bentley, et al. 2008. Supplementary Information. pp. 1-55 Nature. Nov. 6, 2008; 456(7218):53-9.
Bentzen, et al. Large-scale detection of antigen-specific T cells using peptide-MHC-I multimers labeled with DNA barcodes. Nat Biotechnol. Oct. 2016;34(10):1037-1045. doi: 10.1038/nbt.3662. Epub Aug. 29, 2016.
Berkum, et al. Hi-C: a method to study the three-dimensional architecture of genomes. J Vis Exp. May 6, 2010;(39). pii: 1869. doi: 10.3791/1869.
Biles et al., Low-fidelity Pyrococcus furiosis DNA polymerase mutants useful in error-prone PCR. Nucl. Acids Res. 32(22):e176 2004.
Bjornsson et al., Intra-individual change over time in DNA methylation with familial clustering, JAMA, Jun. 25, 2008, vol. 299 No. 24, pp. 2877-2883.
Bodi, K. et al. "Comparison of Commercially Available Target Enrichment Methods for Next-Generation Sequencing" J Biomolecular Techniques (2013) 24:73-86.
Boone, et al. Plastic advances microfluidic devices. The devices debuted in silicon and glass, but plastic fabrication may make them hugely successful in biotechnology application. Analytical Chemistry. Feb. 2002; 78A-86A.
Boulanger, et al, "Massively parallel haplotyping on microscopic beads for the high-throughput phase analysis of single molecules", PLoS One, vol. 7:1-10, 2012.
Boyle, et al. "High-resolution genome-wide in vivo footprinting of diverse transcription factors in human cells", Genome Res. Mar. 2011;21(3):456-64.
Braeckmans et al., Scanning the Code. Modern Drug Discovery. 2003:28-32.
Bransky, et al. A microfluidic droplet generator based on a piezoelectric actuator. Lab Chip. Feb. 21, 2009;9(4):516-20. doi: 10.1039/b814810d. Epub Nov. 20, 2008.

Brenner, et al. In vitro cloning of complex mixtures of DNA on microbeads: physical separation of differentially expressed cDNAs. Proc Natl Acad Sci U S A. Feb. 15, 2000;97(4):1665-70.
Briggs, et al. "Tumor-infiltrating immune repertoires captures by single-cell barcoding in emulsion" with Supplementary material. bioRxiv 134841; doi: https://doi.org/10.1101/134841. Posted May 5, 2017.
Brouzes, et al. Droplet microfluidic technology for single-cell high-throughput screening. Proc Natl Acad Sci U S A. Aug. 25, 2009;106(34):14195-200. doi: 10.1073/pnas.0903542106. Epub Jul. 15, 2009.
Brown, K., Targeted Sequencing Using Droplet-Based Microfluidics, RainDance Technologies, 2009, 1-18.
Browning, et al. Haplotype phasing: existing methods and new developments. Nat Rev Genet. Sep. 16, 2011;12(10):703-14. doi: 10.1038/nrg3054. Review.
Buchman GW, et al. Selective RNA amplification: a novel method using dUMP-containing primers and uracil DNA glycosylase. PCR Methods Appl. Aug. 1993; 3(1):28-31.
Buenrostro, et al. ATAC-seq: A Method for Assaying Chromatin Accessibility Genome-Wide. Curr Protoc Mol Biol.; 109: 21.29.1-21.29.9. doi:10.1002/0471142727.mb2129s109.
Buenrostro, et al. Single-cell chromatin accessibility reveals principles of regulatory variation. Nature. Jul. 23, 2015;523(7561):486-90. doi: 10.1038/nature14590. Epub Jun. 17, 2015.
Buenrostro, et al. "Transposition of native chromatin for fast and sensitive epigenomic profiling of open chromatin, DNA-binding proteins and nucleosome position." Nat Methods. Dec. 2013;10(12):1213-8. doi: 10.1038/nmeth.2688. Epub Oct. 6, 2013.
Burns, et al. An Integrated Nanoliter DNA Analysis Device. Science. Oct. 16, 1998;282(5388):484-7.
Burns, et al. Microfabricated structures for integrated DNA analysis. Proc Natl Acad Sci U S A. May 28, 1996; 93(11): 5556-5561.
Burns, et al. The intensification of rapid reactions in multiphase systems using slug flow in capillaries. Lab Chip. Sep. 2001;1(1):10-5. Epub Aug. 9, 2001.
Cappuzzo, et al. Increased HER2 gene copy number is associated with response to gefitinib therapy in epidermal growth factor receptor-positive non-small-cell lung cancer patients. J Clin Oncol. Aug. 1, 2005;23(22):5007-18.
Carroll, "The selection of high-producing cell lines using flow cytometry and cell sorting", Exp. Op. Bioi. Therp., 4:11 1821-1829 (2004).
Caruccio, et al. Nextera Technology for NGS DNA Library Preparation: Simultaneous Fragmentation and Tagging by In Vitro Transposition, Nextera Technology, 2009, 16-3, 1-3. (Year: 2009).
Caruccio N., Preparation of Next-Generation Sequencing Libraries Using Nextera Technology: Simultaneous DNA Fragmentation and Adaptor Tagging by In Vitro Transposition. Ch. 17 Methods in Microbiology 733:241 (2011).
Casbon, et al, "Reflex: intramolecular barcoding of long-range PCR products for sequencing multiple pooled DNAs", Nucleic Acids Res., pp. 1-6, 2013.
Cejas, P. et al. "Chromatin immunoprecipitation from fixed clinical tissues reveals tumor-specific enhancer profiles" Nature Med (2016) 22(6):685-691.
Chang et al. Droplet-based microfluidic platform for heterogeneous enzymatic assays, 2013, Lab Chip, 13, 1817-1822 (Year: 2013).
Chaudhary "A rapid method of cloning functional variable-region antibody genes in *Escherichia coli* as single-chain immunotoxins" Proc. Natl. Acad. Sci USA 87: 1066-1070 (Feb. 1990).
Chechetkin et al., Sequencing by hybridization with the generic 6-mer oligonucleotide microarray: an advanced scheme for data processing. J Biomol Struct Dyn. Aug. 2000;18(1):83-101.
Chen, et al. Chemical transfection of cells in picoliter aqueous droplets in fluorocarbon oil. Anal Chem. Nov. 15, 2011;83(22):8816-20. doi: 10.1021/ac2022794. Epub Oct. 17, 2011.
Choi, et al. Identification of novel isoforms of the EML4-ALK transforming gene in non-small cell lung cancer. Cancer Res. Jul. 1, 2008;68(13):4971-6. doi: 10.1158/0008-5472.CAN-07-6158.
Chokkalingam, et al. Probing cellular heterogeneity in cytokine-secreting immune cells using droplet-based microfluidics. Lab Chip. Dec. 21, 2013;13(24):4740-4. doi: 10.1039/c31c50945a.

(56) References Cited

OTHER PUBLICATIONS

Chou, et al. Disposable Microdevices for DNA Analysis and Cell Sorting. Proc. Solid-State Sensor and Actuator Workshop, Hilton Head, SC. Jun. 8-11, 1998; 11-14.
Christian, et al. Targeting DNA double-strand breaks with TAL effector nucleases. Genetics.186 (2010): 757-761.
Christiansen et al. "The Covalent Eukaryotic Topoisomerase I-DNA Intermediate Catalyzes pH-dependent Hydrolysis and Alcoholysis" J Biol Chem (Apr. 14, 1994) 269(15):11367-11373.
Chu, et al. Controllable monodisperse multiple emulsions. Angew Chem Int Ed Engl. 2007;46(47):8970-4.
Chung, et al. Structural and molecular interrogation of intact biological systems. Nature. May 16, 2013;497(7449):332-7. doi: 10.1038/nature12107. Epub Apr. 10, 2013.
Clark, et al. Single-cell epigenomics: powerful new methods for understanding gene regulation and cell identity. Genome Biol. Apr. 18, 2016;17:72. doi: 10.1186/s13059-016-0944-x.
Clausell-Tormos et al., "Droplet-based microfluidic platforms for the encapsulation and screening of mammalian cells and multicellular organisms", Chem. Biol. 15:427-437 (2008).
Cong, et al. Multiplex genome engineering using CRISPR/Cas systems. Science. 339.6121 (Feb. 15, 2013): 819-23. doi: 10.1126/science.1231143. Epub Jan. 3, 2013.
Cook, et al. Copy-number variations associated with neuropsychiatric conditions. Nature. Oct. 16, 2008;455(7215):919-23. doi: 10.1038/nature07458.
Co-pending U.S. Appl. No. 15/440,772, filed Feb. 23, 2017.
Co-pending U.S. Appl. No. 15/449,741, filed Mar. 3, 2017.
Co-pending U.S. Appl. No. 16/033,065, filed Jul. 11, 2018.
Co-pending U.S. Appl. No. 16/044,374, filed Jul. 24, 2018.
Co-pending U.S. Appl. No. 16/107,685, filed Aug. 21, 2018.
Co-pending U.S. Appl. No. 16/160,576, filed Oct. 15, 2018.
Co-pending U.S. Appl. No. 16/160,719, filed Oct. 15, 2018.
Co-pending U.S. Appl. No. 16/165,389, filed Oct. 19, 2018.
Co-pending U.S. Appl. No. 16/170,980, filed Oct. 25, 2018.
Co-pending U.S. Appl. No. 16/196,684, filed Nov. 20, 2018.
Co-pending U.S. Appl. No. 16/206,168, filed Nov. 30, 2018.
Co-pending U.S. Appl. No. 16/212,441, filed Dec. 6, 2018.
Co-pending U.S. Appl. No. 16/228,261, filed Dec. 20, 2018.
Co-pending U.S. Appl. No. 16/228,362, filed Dec. 20, 2018.
Co-pending U.S. Appl. No. 16/230,936, filed Dec. 21, 2018.
Co-pending U.S. Appl. No. 16/231,142, filed Dec. 21, 2018.
Co-pending U.S. Appl. No. 16/231,185, filed Dec. 21, 2018.
Co-pending U.S. Appl. No. 16/242,962, filed Jan. 8, 2019.
Co-pending U.S. Appl. No. 16/246,322, filed Jan. 11, 2019.
Co-pending U.S. Appl. No. 16/249,688, filed Jan. 16, 2019.
Coufal, et al. L1 retrotransposition in human neural progenitor cells. Nature. Aug. 27, 2009;460(7259):1127-31. doi: 10.1038/nature08248. Epub Aug. 5, 2009.
Curcio. Improved Techniques for High-Throughput Molecular Diagnostics. PhD Thesis. 2002.
Cusanovich; et al., "Multiplex single-cell profiling of chromatin accessibility by combinatorial cellular indexing. Sciencexpress, May 7, 2014, p. 1-9.".
Cusanovich, et al. Supplementary materials for Multiplex single-cell profiling of chromatin accessibility by combinatorial cellular indexing. Science. May 22, 2015;348(6237):910-4. doi: 10.1126/science.aab1601. Epub May 7, 2015.
Damean, et al. Simultaneous measurement of reactions in microdroplets filled by concentration gradients. Lab Chip. Jun. 21, 2009;9(12):1707-13. doi: 10.1039/b821021g. Epub Mar. 19, 2009.
De Bruin et al., UBS Investment Research. Q-Series®: DNA Sequencing. UBS Securities LLC. Jul. 12, 2007. 15 pages.
Dekker, et al. Capturing chromosome conformation. Science. Feb. 15, 2002;295(5558):1306-11.
Delehanty, et al. Peptides for specific intracellular delivery and targeting of nanoparticles: implications for developing nanoparticle-mediated drug delivery. Ther Deliv. Sep. 2010;1(3):411-33.
Demirci, et al. Single cell epitaxy by acoustic picolitre droplets. Lab Chip. Sep. 2007;7(9):1139-45. Epub Jul. 10, 2007.

Depristo et al. A framework for variation discovery and genotyping using next-generation DNA sequencing data. Nature Genet 43:491-498 (2011).
Dey, et al. Integrated genome and transcriptome sequencing of the same cell. Dey, Siddharth S. et al. "Integrated Genome and Transcriptome Sequencing from the Same Cell." Nature biotechnology 33.3 (2015): 285-289. PMC. Web. Dec. 18, 2017.
Dixit, et al. Perturb-Seq: Dissecting Molecular Circuits with Scalable Single-Cell RNA Profiling of Pooled Genetic Screens. Cell. Dec. 15, 2016;167(7):1853-1866.e17. doi: 10.1016/j.cell.2016.11.038.
Doerr, "The smallest bioreactor", Nature Methods, 2:5 326 (2005).
Doshi, et al. Red blood cell-mimicking synthetic biomaterial particles. Proceedings of the National Academy of Sciences 106.51 (2009): 21495-21499.
Dowding, et al. Oil core/polymer shell microcapsules by internal phase separation from emulsion droplets. II: controlling the release profile of active molecules. Langmuir. Jun. 7, 2005;21(12):5278-84.
Draper, et al. Compartmentalization of electrophoretically separated analytes in a multiphase microfluidic platform. Anal Chem. Jul. 3, 2012;84(13):5801-8. doi: 10.1021/ac301141x. Epub Jun. 13, 2012.
Dressler, et al. Droplet-based microfluidics enabling impact on drug discovery. J Biomol Screen. Apr. 2014;19(4):483-96. doi: 10.1177/1087057113510401. Epub Nov. 15, 2013.
Dressman et al. Supplementary Information pp. 1-2 of article published 2003, PNAS 100(15:8817-22).
Dressman et al. Transforming single DNA molecules into fluorescent magnetic particles for detection and enumeration of genetic variations. Proc. Natl. Acad. Sci. 2003. 100(15):8817-8822.
Drmanac et al., Sequencing by hybridization (SBH): advantages, achievements, and opportunities. Adv Biochem Eng Biotechnol. 2002;77 :75-101.
Droplet Based Sequencing (slides) dated (Mar. 12, 2008).
Eastburn, et al. Ultrahigh-throughput mammalian single-cell reverse-transcriptase polymerase chain reaction in microfluidic droplets. Anal Chem. Aug. 20, 2013;85(16):8016-21. doi: 10.1021/ac402057q. Epub Aug. 8, 2013.
Epicentre., "EZ-Tn5TM Custom Transposome Construction Kits", http://www.epicentre.com, pp. 1-17, 2012.
Esser-Kahn, et al. Triggered release from polymer capsules. Macromolecules. 2011; 44:5539-5553.
Fabi, et al. Correlation of efficacy between EGFR gene copy number and lapatinib/capecitabine therapy in HER2-positive metastatic breast cancer. J. Clin. Oncol. 2010; 28:15S. 2010 ASCO Meeting abstract Jun. 14, 2010:1059.
Fan, et al. Noninvasive diagnosis of fetal aneuploidy by shotgun sequencing DNA from maternal blood. Proc Natl Acad Sci U S A. Oct. 21, 2008;105(42):16266-71. Epub Oct. 6, 2008.
Fan, et al. Whole-genome molecular haplotyping of single cells. Nature Biotechnology, vol. 29, No. 1. Jan. 1, 2011. pp. 51-57.
Fang, et al. Fluoride-cleavable biotinylation phosphoramidite for 5'-end-labeling and affinity purification of synthetic oligonucleotides. Nucleic Acids Res. Jan. 15, 2003;31(2):708-15.
Fanielli, M. et al. "Pathology tissue-chromatin immunoprecipitation, coupled with high-throughput sequencing, allows the epigenetic profiling of patient samples" PNAS (2010) 107(50):21535-21540.
Fisher, et al. A scalable, fully automated process for construction of sequence-ready human exome targeted capture libraries. Genome Biol. 2011;12(1):R1. doi: 10.1186/gb-2011-12-1-r1. Epub Jan. 4, 2011.
Frampton, G.M. et al. "Development and validation of a clinical cancer genomic profiling test based on massively parallel DNA sequencing" Nature Biotechnology (2013) 31(11):1023-1031. doi:10.1038/nbr.2696.
Fredrickson, et al. Macro-to-micro interfaces for microfluidic devices. Lab Chip. Dec. 2004;4(6):526-33. Epub Nov. 10, 2004.
Freiberg, et al. Polymer microspheres for controlled drug release. Int J Pharm. Sep. 10, 2004;282(1-2):1-18.
Fu, et al. A Microfabricated Fluorescence-Activated Cell Sorter. Nature Biotechnology.1999; 17:1109-1111.
Fulton, et al. Advanced multiplexed analysis with the FlowMetrix system. Clin Chem. Sep. 1997;43(9):1749-56.

(56) References Cited

OTHER PUBLICATIONS

Gangadharan et al., DNA transposon Hermes insert into DNA in nucleosome-free regions in vivo, Proc nat Ad Sci, Dec. 21, 2010, vol. 107, No. 51, pp. 1966-1972.
Gao et al., Toehold of dsDNA Exchange Affects the Hydrogel Swelling Kinetic of a Polymer-dsDNA Hybrid Hydrogel, Royal Soc. Chem. 7:1741-1746 (Dec. 20, 2010).
Garstecki, et al. Formation of monodisperse bubbles in a microfluidic flow-focusing device. Applied Physics Letters. 2004; 85(13):2649-2651. DOI: 10.1063/1.1796526.
Gartner, et al. The Microfluidic Toolbox—examples for fluidic interfaces and standardization concepts. Proc. SPIE 4982, Microfluidics, BioMEMS, and Medical Microsystems, (Jan. 17, 2003); doi: 10.1117/12.479566.
Gericke, et al. Functional cellulose beads: preparation, characterization, and applications. Chemical reviews 113.7 (2013): 4812-4836.
Ghadessy, et al. Directed evolution of polymerase function by compartmentalized self-replication. Proc Natl Acad Sci USA. 2001;98:4552-4557.
Gonzalez, et al. The influence of CCL3L1 gene-containing segmental duplications on HIV-1/AIDS susceptibility. Science. Mar. 4, 2005;307(5714):1434-40. Epub Jan. 6, 2005.
Granieri, Lucia. Droplet-based microfluidics and engineering of tissue plasminogen activator for biomedical applications. Ph.D. Thesis, Nov. 13, 2009 (131 pages).
Grasland-Mongrain, et al. Droplet coalescence in microfluidic devices. Jan.-Jul. 2003. 31 pages. http://www.eleves.ens.fr/home/grasland/rapports/stage4.pdf.
Green et al. Insertion site preference of Mu, Tn5, and Tn7 transposons. Mobile DNA 3.1 (2012): 3.
Greenleaf, et al. Assaying the epigenome in limited numbers of cells. Methods. Jan. 15, 2015;72:51-6. doi: 10.1016/j.ymeth.2014.10.010. Epub Oct. 22, 2014.
Guo, et al. Droplet microfluidics for high-throughput biological assays. Lab Chip. Jun. 21, 2012;12(12):2146-55. doi: 10.1039/c2lc21147e. Epub Feb. 9, 2012.
Gyarmati, et al. Reversible disulphide formation in polymer networks: a versatile functional group from synthesis to applications. European Polymer Journal. 2013; 49:1268-1286.
Hamilton, A.J. "microRNA in erythrocytes" Biochem. Soc. Trans. (2010) 38, 229-231.
Han, SW et al. "Targeted Sequencing of Cancer-Related Genes in Colorectal Cancer Using Next-Generation Sequencing" PLOS One (2013) 8(5):e64271.
Han, X. et al. "CRISPR-Cas9 delivery to hard-to-transfect cells via membrane deformation" Science Advances (2015) 1(7): E1500454 (8 pages).
Haring, et al. Chromatin immunoprecipitation: optimization, quantitative analysis and data normalization. Plant Methods. 2007; 3: 11.
Hashimshony, et al. CEL-Seq: Single-Cell RNA-Seq by Multiplexed Linear Amplification. Cell Rep. Sep. 27, 2012;2(3):666-73. doi: 10.1016/j.celrep.2012.08.003. Epub Aug. 30, 2012.
He, "Selective Encapsulation of Single Cells and Subcellular Organelles into Picoliter- and Femtoliter-Volume Droplets" Anal. Chem 77: 1539-1544 (2005).
He, J. et al. "Genotyping-by-sequencing (GBS), an ultimate marker-assisted selections (MAS) tool to accelerate plant breeding" Frontiers in Plant Sci (Sep. 30, 2014) 5:1-8.
Hebenstreit. Methods, Challenges and Potentials of Single Cell RNA-seq. Biology (Basel). Nov. 16, 2012;1(3):658-67. doi: 10.3390/biology1030658.
Hiatt, et al. Parallel, tag-directed assembly of locally derived short sequence reads. Nat Methods. Feb. 2010;7(2):119-22. Epub Jan. 17, 2010.
Hirsch et al. (2002) "Easily reversible desthiobiotin binding to streptavidin, avidin, and other biotin-binding proteins: uses for protein labeling, detection, and isolation." Analytical of Biochemistry 308(2):343-357.
Hjerten, et al. General methods to render macroporous stationary phases nonporous and deformable, exemplified with agarose and silica beads and their use in high-performance ion-exchange and hydrophobic-interaction chromatography of proteins. Chromatographia 31.1-2 (1991): 85-94.
Holtze, et al. Biocompatible surfactants for water-in-fluorocarbon emulsions. Lab Chip. Oct. 2008;8(10):1632-9. doi: 10.1039/b806706f. Epub Sep. 2, 2008.
Hosokawa, et al. Massively parallel whole genome amplification for single-cell sequencing using droplet microfluidics. Scientific Reports 7, Article No. 5199 (2017).
Hosono S, et al. Unbiased whole-genome amplification directly from clinical samples. Genome Res. May 2003; 13(5):954-64. Epub Apr. 14, 2003.
"How many species of bacteria are there" (wisegeek.com; accessed Jan. 21, 2014).
Hu et al., Shape Controllable Microgel Particles Prepared by Microfluidic Combining External Crosslinking, Biomicrofluidics 6:26502 (May 18, 2012).
Huebner, "Quantitative detection of protein expression in single cells using droplet microfluidics", Chem. Commun. 1218-1220 (2007).
Hug, et al. Measurement of the number of molecules of a single mRNA species in a complex mRNA preparation. J Theor Biol. Apr. 21, 2003;221(4):615-24.
Illumina Nextera Enrichment Sample Preparation Guide. Feb. 2013.
Illumina TruSeq Custom Enrichment Kit Data Sheet. (c) 2014.
Imburgio, et al, "Studies of promoter recognition and start site selection by T7 RNA polymerase using a comprehensive collection of promoter variants", Biochemistry., 39:10419-30, 2000.
Ioannidis, N. Manufacturing of agarose-based chromatographic adsorbents with controlled pore and particle sizes. A thesis submitted to the University of Birmingham for the degree of Doctor of Philosophy. 2009.
Jena, et al. Cyclic olefin copolymer based microfluidic devices for biochip applications: Ultraviolet surface grafting using 2-methacryloyloxyethyl phosphorylcholine. Biomicrofluidics. Mar. 2012;6(1):12822-1282212. doi: 10.1063/1.3682098. Epub Mar. 15, 2012.
Jin, et al. Genome-wide detection of DNase I hypersensitive sites in single cells and FFPE tissue samples. Nature. Dec. 3, 2015;528(7580):142-6. doi: 10.1038/nature15740.
Joneja, et al. Linear nicking endonuclease-mediated strand-displacement DNA amplification. Anal Biochem. Jul. 1, 2011;414(1):58-69. doi: 10.1016/j.ab.2011.02.025. Epub Feb. 20, 2011.
JPK "Determining the elastic modulus of biological samples using atomic force microscopy" (https://www.jpk.com/ app-technotes-img/AFM/pdf/jpk-app-elastic-modulus.14-1.pdf) 2009, pp. 1-9 (Year: 2009).
Jung, et al. Micro machining of injection mold inserts for fluidic channel of polymeric biochips. Sensors. 2007; 7(8):1643-1654.
Kamperman, et al. Centering Single Cells in Microgels via Delayed Crosslinking Supports Long-Term 3D Culture by Preventing Cell Escape. Small. Jun. 2017;13(22). doi: 10.1002/smll.201603711. Epub Apr. 28, 2017.
Kaper, et al. Supporting Information for "Whole-genome haplotyping by dilution, amplification, and sequencing." Proc Natl Acad Sci U S A. Apr. 2, 2013;110(14):5552-7. doi: 10.1073/pnas.1218696110. Epub Mar. 18, 2013.
Kaper, et al. Whole-genome haplotyping by dilution, amplification, and sequencing. Proc Natl Acad Sci U S A. Apr. 2, 2013;110(14):5552-7. doi: 10.1073/pnas.1218696110. Epub Mar. 18, 2013.
Karmakar, et al. Organocatalytic removal of formaldehyde adducts from RNA and DNA bases. Nat Chem. Sep. 2015;7(9):752-8. doi: 10.1038/nchem.2307. Epub Aug. 3, 2015.
Katsura, et al. Indirect micromanipulation of single molecules in water-in-oil emulsion. Electrophoresis. Jan. 2001;22(2):289-93.
Kebschull, et al. High-Throughput Mapping of Single-Neuron Projections by Sequencing of Barcoded RNA. Neuron. Sep. 7, 2016;91(5):975-87. doi: 10.1016/j.neuron.2016.07.036. Epub Aug. 18, 2016.
Kenis, et al. Microfabrication Inside Capillaries Using Multiphase Laminar Flow Patterning. Science. 1999; 285:83-85.

(56) References Cited

OTHER PUBLICATIONS

Khomiakova et al., Analysis of perfect and mismatched DNA duplexes by a generic hexanucleotide microchip. Mol Biol(Mosk). Jul.-Aug. 2003;37(4):726-41. Russian. Abstract only.
Kim et al., Albumin loaded microsphere of amphiphilic poly( ethylene glycol)/poly(a-ester) multiblock copolymer. Eu. J. Pharm. Sci. 2004;23:245-51. Available online Sep. 27, 2004.
Kim, et al. Fabrication of monodisperse gel shells and functional microgels in microfluidic devices. Angew Chem Int Ed Engl. 2007;46(11):1819-22.
Kim, et al. Rapid prototyping of microfluidic systems using a PDMS/polymer tape composite. Lab Chip. May 7, 2009;9(9):1290-3. doi: 10.1039/b818389a. Epub Feb. 10, 2009.
Kirkness et al. "Sequencing of isolated sperm cells for direct haplotyping of a human genome," Genome Res (2013) 23:826-832.
Kitzman et al. "Haplotype-resolved genome sequencing of a Gujarati Indian individual." Nat Biotechnol (2011) 29:59-63.
Kitzman, et al. Noninvasive whole-genome sequencing of a human fetus. Sci Transl Med. Jun. 6, 2012;4(137):137ra76. doi: 10.1126/scitranslmed.3004323.
Kivioja, et al. Counting absolute numbers of molecules using unique molecular identifiers. Nat Methods. Nov. 20, 2011;9(1):72-4.
Klein, et al. Droplet barcoding for single-cell transcriptomics applied to embryonic stem cells. Cell. May 21, 2015;161(5):1187-201. doi: 10.1016/j.cell.2015.04.044.
Knapp, et al. Generating barcoded libraries for multiplex high-throughput sequencing. Methods Mol Biol. 2012;840:155-70. doi: 10.1007/978-1-61779-516-9_19.
Knight, et al. Subtle chromosomal rearrangements in children with unexplained mental retardation. Lancet. Nov. 13, 1999;354(9191):1676-81.
Kolodeziejczyk et al., "The technology and biology of single-cell RNA sequencing", Molecular Cell, vol. 58 (May 21, 2015).
Korlach et al., Methods in Enzymology, Real-Time DNA Sequencing from Single Polymerase Molecules, (2010) 472:431-455.
Koster et al., "Drop-based microfluidic devices for encapsulation of single cells", Lab on a Chip The Royal Soc. of Chem. 8: 1110-1115 (2008).
Kozarewa, et al, "96-plex molecular barcoding for the Illumina Genome Analyzer", Methods Mol Biol., 733:279-98, 2011.
Kozarewa, et al. "Amplification-free Illumina sequencing-library preparation facilitates improved mapping and assembly of GC-biased genomes", Nat Methods., 6: 291-5, 2009.
Kutyavin, et al. Oligonucleotides containing 2-aminoadenine and 2-thiothymine act as selectively binding complementary agents. Biochemistry. Aug. 27, 1996;35(34):11170-6.
Kwok, et al, "Single-molecule analysis for molecular haplotyping", Hum Mutat., 23:442-6, 2004.
Lagally, et al. Single-Molecule DNA Amplification and Analysis in an Integrated Microfluidic Device. Anal Chem. Feb. 1, 2001;73(3):565-70.
Lagus, et al. A review of the theory, methods and recent applications of high-throughput single-cell droplet microfluidics. J. Phys. D: Appl. Phys. (2013) 46:114005. (21 pages).
Lai; et al., ""Characterization and Use of Laser-Based Lysis for Cell Analysis On-Chip", Journal of the Royal Society, Interface, vol. 5, Supplement 2, pp. S113-S121, Oct. 2008, (Year:2008)", Journal of the Royal Society, Interface, Oct. 2008, vol. 5, Supplement 2, S113-S121.
Laird et al, Hairpin-bisulfite PCR: Assessing epigenetic methylation patterns on complementary strands of individual DNA molecules, 2004, PNAS, 101, 204-209.
Lake, et al. "Integrative Single-Cell Analysis by Transcriptional and Epigenetic States in Human Adult Brain". Apr. 19, 2017. doi: https://doi.org/10.1101/128520.
Lan, et al. "Single-cell genome sequencing at ultra-high-throughput with microfluidic droplet barcoding" with Supplementary Material. Nat Biotechnol. May 29, 2017. doi: 10.1038/nbt.3880. [Epub ahead of print].

Lander, et al. Initial sequencing and analysis of the human genome. Nature, 409 (Feb. 15, 2001): 860-921.
Lasken, et al. (1996) Archaebacterial DNA Polymerases Tightly Bind Uracil-containing DNA. The Journal of Biological Chemistry, 271(30):17692-17696 (Year: 1996).
Lebedev, A. et al. "Hot Start PCR with heat-activatable primers: a novel approach for improved PCR performance" NAR (2008) 36(20):E131-1.
Lee, et al. ACT-PRESTO: Rapid and consistent tissue clearing and labeling method for 3-dimensional (3D) imaging. Sci Rep. Jan. 11, 2016;6:18631. doi: 10.1038/srep18631.
Lee et al. Alginate: Properties and biomedical applications. Prog Polym Sci 37(1):106-126 (2012).
Lee, et al., "Highly multiplexed subcellular RNA sequencing in situ. Science. Mar. 21, 2014;343(6177):1360-3. doi: 10.1126/science. 1250212. Epub Feb. 27, 2014.".
Lee, J-H. et al. "Fluorescent in situ sequencing (FISSEQ) of RNA for gene expression profiling in intact cells and tissues" Nature Protocols (Feb. 12, 2015) 10(3):442-458.
"Lennon et al. A scalable, fully automated process for construction of sequence-ready barcoded libraries for 454. Genome Biology 11:R15 (2010).".
Li, et al. A single-cell-based platform for number variation profiling through digital counting of amplified genomic DNA fragments. ACS Appl Mater Interfaces. Mar. 24, 2017. doi: 10.1021/acsami. 7b03146. [Epub ahead of print].
Li, Y., et al., "PEGylated PLGA Nanoparticles as protein carriers: synthesis, preparation and biodistribution in rats," Journal of Controlled Release, vol. 71, pp. 203-211 (2001).
Lienemann, et al. Single cell-laden protease-sensitive microniches for long-term culture in 3D. Lab Chip. Feb. 14, 2017;17(4):727-737. doi: 10.1039/c61c01444e.
Linch, et al. Bone marrow processing and cryopreservation. Journal of Clinical Pathology; Feb. 1982, vol. 35, No. 2; pp. 186-190.
"List of sequenced bacterial genomes" (Wikipedia.com; accessed Jan. 24, 2014).
Liu, et al. Preparation of uniform-sized PLA microcapsules by combining Shirasu porous glass membrane emulsification technique and multiple emulsion-solvent evaporation method. J Control Release. Mar. 2, 2005;103(1):31-43. Epub Dec. 21, 2004.
Liu, et al. Smart thermo-triggered squirting capsules for Nanoparticle delivery. Soft Matter. 2010; 6(16):3759-3763.
Lo, et al. On the design of clone-based haplotyping. Genome Biol. 2013;14(9):R100.
Loscertales, I.G., et al., "Micro/Nano Encapsulation via Electrified Coaxial Liquid Jets," Science, vol. 295, pp. 1695-1698 (2002).
Love, "A microengraving method for rapid selection of single cells producing antigen-specific antibodies", Nature Biotech, 24:6 703 (Jun. 2006).
Lowe, Adam J. Norbornenes and [n]polynorbornanes as molecular scaffolds for anion recognition. Ph.D. Thesis (May 2010). (361 pages).
Lundin, et al, "Hierarchical molecular tagging to resolve long continuous sequences by massively parallel sequencing", Sci Rep., 3:1186, 2003.
Lupski. Genomic rearrangements and sporadic disease. Nat Genet. Jul. 2007;39(7 Suppl):S43-7.
Macaulay; et al., "G&T-seq: parallel sequencing of single-cell genomes and transcriptomes. Nature Methods, 2015, p. 1-7.".
Macaulay, et al. Single-Cell Multiomics: Multiple Measurements from Single Cells. Trends in Genetics 33.2 (2017): 155-168. PMC. Web. Dec. 18, 2017.
Macosko, et al. Highly Parallel Genome-wide Expression Profiling of Individual Cells Using Nanoliter Droplets. Cell. May 21, 2015;161(5):1202-14. doi: 10.1016/j.cell.2015.05.002.
Mair, et al. Injection molded microfluidic chips featuring integrated interconnects. Lab Chip. Oct. 2006;6(10):1346-54. Epub Jul. 31, 2006.
Makino, et al. Preparation of hydrogel microcapsules: Effects of preparation conditions upon membrane properties. Colloids and Surfaces B: Biointerfaces. Nov. 1998; 12(2), 97-104.

(56) References Cited

OTHER PUBLICATIONS

Mali, et al. Barcoding cells using cell-surface programmable DNA-binding domains. Nat Methods. May 2013;10(5):403-6. doi: 10.1038/nmeth.2407. Epub Mar. 17, 2013.
Man. Monolithic Structures for Integrated Microfluidic Analysis. PhD Thesis. 2001.
Marcus. Gene method offers diagnostic hope. The Wall Street Journal. Jul. 11, 2012.
Margulies 2005 Supplementary methods (Year: 2005).
Margulies et al. "Genome sequencing in microfabricated high-density picoliter reactors", Nature (2005) 437:376-380.
Maricic T, et al. Optimization of 454 sequencing library preparation from small amounts of DNA permits sequence determination of both DNA strands. Biotechniques. Jan. 2009; 46(1):51-2, 54-7.
Matochko, et al. Uniform amplification of phage display libraries in monodisperse emulsions. Methods. Sep. 2012;58(1):18-27. doi: 10.1016/j.ymeth.2012.07.012. Epub Jul. 20, 2012.
Mazutis, et al. Selective droplet coalescence using microfluidic systems. Lab Chip. Apr. 24, 2012;12(10):1800-6. doi: 10.1039/c2lc40121e. Epub Mar. 27, 2012.
McGinnis, et al. Multi-seq: Scalable sample multiplexing for single-cell RNA sequencing using lipid-tagged indices. bioRxiv 387241; doi: https://doi.org/10.1101/387241 . . . .
Merriman, et al. Progress in ion torrent semiconductor chip based sequencing. Electrophoresis. Dec. 2012;33(23):3397-417. doi: 10.1002/elps.201200424.
"Meyer, et al., From micrograms to picograms: quantitative PCR reduces the material demands of high-throughput sequencing, Nucleic Acids Research, 2008, vol. 36, No. 1, 6 pages".
Meyer, et al. Targeted high-throughput sequencing of tagged nucleic acid samples. Nucleic Acids Res. 2007;35(15):e97.
Microfluidic ChipShop. Microfluidic product catalogue. Mar. 2005.
Microfluidic ChipShop. Microfluidic product catalogue. Oct. 2009.
Mignardi, M. et al. "Oligonucleotide gap-fill ligation for mutation detection and sequencing in situ" Nucl Acids Res (2015) 43(22):e151.
Miller JC, et al. An improved zinc-finger nuclease architecture for highly specific genome editing. Nat. Biotechnol. 2007;25:778-785.
Miller-Stephenson Chemicals 157 FS Series catalog, www.miller-stephenon.com.
MiRNA (http://www.exiqon.com/what-are-microRNAs) accessed Oct. 19, 2017.
Mirzabekov, "DNA Sequencing by Hybridization—a Megasequencing Method and a Diagnostic Tool?" Trends in Biotechnology 12(1): 27-32 (1994).
Moore, et al. Behavior of capillary valves in centrifugal microfluidic devices prepared by three-dimensional printing. Microfluidics and Nanofluidics. 2011; 10(4):877-888.
Morgan, et al. Chapter 12: Human microbiome analysis. PLoS Comput Biol. 2012;8(12):e1002808. doi: 10.1371/journal.pcbi.1002808. Epub Dec. 27, 2012.
Morimoto, et al. Monodisperse semi-permeable microcapsules for continuous observation of cells. 2009. Lab Chip 9(15):2217-2223.
Mouritzen et al., Single nucleotide polymorphism genotyping using locked nucleic acid (LNa). Expert Rev Mol Diagn. Jan. 2003;3(1):27-38.
Mozhanova, A.A. et al. "Local elastic properties of biological materials studied by SFM" (2003) XP055314108, Retrieved from the Internet: URL:http://www.ntmdt.com/data/media/files/publications/2003/08.08_a.a.mozhanova_n.i.n_english.pdf.
Muotri, et al. L1 retrotransposition in neurons is modulated by MeCP2. Nature. Nov. 18, 2010;468(7322):443-6. doi: 10.1038/nature09544.
Myllykangas et al., Targeted Sequencing Library Preparation by Genomic DNA Circularization, BMC Biotechnology, 2011, 11(122), 1-12.
Nagano, et al. Single-cell Hi-C reveals cell-to-cell variability in chromosome structure. Nature. Oct. 3, 2013;502(7469):59-64. doi: 10.1038/nature12593. Epub Sep. 25, 2013.
Nagashima, et al. Preparation of monodisperse poly (acrylamide-co-acrylic acid) hydrogel microspheres by a membrane emulsification technique and their size-dependent surface properties. Colloids and Surfaces B: Biointerfaces. Jun. 15, 1998; 11(1-2), 47-56.
Narayanan, J. et al. "Determination of agarose gel pore size: Absorbance measurements vis a vis other techniques" Journal of Physics: Conference Series 28 (2006) 83-86 (Year: 2006).
Navin. The first five years of single-cell cancer genomics and beyond. Genome Res. Oct. 2015;25(10):1499-507. doi: 10.1101/gr.191098.115.
Nguyen, et al. In situ hybridization to chromosomes stabilized in gel microdrops. Cytometry. 1995; 21:111-119.
Nisisako, et al. Droplet formation in a microchannel network. Lab Chip. Feb. 2002;2(1):24-6. Epub Jan. 18, 2002.
Nisisako, T. et al. "Droplet Formation in a Microchannel on PMMA Plate" Abstract. 2001 Kluwer Academic Publishers. p. 137-138.
Novak, et al. Single cell multiplex gene detection and sequencing using microfluidicallygenerated agarose emulsions. Angew Chem Int Ed Engl. Jan. 10, 2011;50(2):390-5. doi: 10.1002/anie.201006089.
Oberholzer, et al. Polymerase chain reaction in liposomes. Chem Biol. Oct. 1995;2(10):677-82.
Ogawa, et al. Production and characterization of O/W emulsions containing cationic droplets stabilized by lecithin-chitosan membranes. J Agric Food Chem. Apr. 23, 2003;51(9):2806-12.
Okushima, S., et al,. "Controlled Production ofMonodisperse Double Emulsions by Two-Step Droplet Breakup in Microfluidic Devices," Langmuir, vol. 20, pp. 9905-9908 (2004).
Oligotex Handbook. For purification of poly A+ RNA from total RNA and directly from cultured cells or tissues as well as purification of polyadenylated in vitro transcripts. Jun. 2012.
Orakdogen, N. "Novel responsive poly(N,N-dimethylaminoethyl methacrylate) gel beads: preparation, mechanical properties and pH-dependent swelling behavior" J Polym Res (2012) 19:9914.
Oyola, et al, "Optimizing Illumina next-generation sequencing library preparation for extremely AT-biased genomes", BMC Genomics.,13:1, 2012.
Pantel, et al. Detection methods of circulating tumor cells. J Thorac Dis. Oct. 2012;4(5):446-7. doi: 10.3978/j.issn.2072-1439.2012.08.15.
Park. ChIP-seq: advantages and challenges of a maturing technology. Nature Reviews Genetics vol. 10, pp. 669-680 (2009).
Patel, et al. Single-cell RNA-seq highlights intratumoral heterogeneity in primary glioblastoma. Science. Jun. 20, 2014;344(6190):1396-401. doi: 10.1126/science.1254257. Epub Jun. 12, 2014.
Perez, C., et al., "Poly(lactic acid)-poly(ethylene glycol) Nanoparticles as new carriers for the delivery of plasmid DNA," Journal of Controlled Release, vol. 75, pp. 211-224 (2001).
Perrott, Jimmy. Optimization and Improvement of Emulsion PCR for the Ion Torrent Next-Generation Sequencing Platform. (2011) Thesis.
Peters, B.A. et al. Accurate whole-genome sequencing and haplotyping from 10 to 20 human cells. Nature, 487(7406):190-195 (Jul. 11, 2012).
Pfeifer, et al. Bivalent cholesterol-based coupling of oligonucleotides to lipid membrane assemblies. J Am Chem Soc. Aug. 25, 2004;126(33):10224-5.
Picot, J. et al. "A biomimetic microfluidic chip to study the circulation and mechanical retention of red blood cells in the spleen" Am J Hematology (Jan. 12, 2015) 90(4):339-345.
Pinto, et al. Functional impact of global rare number variation in autism spectrum disorders. Nature. Jul. 15, 2010;466(7304):368-72. doi: 10.1038/nature09146. Epub Jun. 9, 2010.
Plunkett, et al. Chymotrypsin responsive hydrogel: application of a disulfide exchange protocol for the preparation of methacrylamide containing peptides. Biomacromolecules. Mar.-Apr. 2005;6(2):632-7.
"Portable Water Filters" (http://www.portablewaterfilters.org/water-filter-guide/particle-contaminant-size-chart-microns/) 2015, accessed Oct. 19, 2017.
Porteus MH, Baltimore D. Chimeric nucleases stimulate gene targeting in human cells. Science. 2003;300:763.
Pott, et al. Single-cell ATAC-seq: strength in numbers. Genome Biol. Aug. 21, 2015;16:172. doi: 10.1186/s13059-015-0737-7.

(56) References Cited

OTHER PUBLICATIONS

Preissl, et al. Single nucleus analysis of the chromatin landscape in mouse forebrain development. Posted Jul. 4, 2017. bioRxiv 159137; doi: https://doi.org/10.1101/159137.
"U.S. Appl. No. 61/982,001, filed Apr. 21, 2014 (Year:2014)".
Rakszewska, A. et al. "One drop at a time: toward droplet microfluidics as a versatile tool for single-cell analysis" NPG Asia Materials (2014) 6(10):e133 (12 pages).
Ram, et al. Strategy for microbiome analysis using 16S rRNA gene sequence analysis on the Illumina sequencing platform. Syst Biol Reprod Med. Jun. 2011;57(3):162-70. doi: 10.3109/19396368.2011.555598. Epub Mar. 1, 2011.
Ramsey, J.M. "The burgeoning power of the shrinking laboratory" Nature Biotech (1999) 17:1061-1062.
Ramskold et al. (2012) "Full-length mRNA-Seq from single-cell levels of RNA and individual circulating tumor cells" Nature Biotechnology 30(8):777-782.
Ran et al. Genome engineering using the CRISPR-Cas9 system. Nature Protocols 8:2281-2308 (2013).
Reis, A. et al. "CRISPR/Cas9 and Targeted Genome Editing: A New Era in Molecular Biology" (2014) XP002766825: URL:https://ww.neb.com/tools-and-resources/feabture-articles/crispr-cas9-and-targeted-genome-editing-a-new-era-in-molecular-biology.
Reisner, et al, "Single-molecule denaturation mapping of DNA in nanofluidic channels", Proc Natl Acad Sci U.S.A., 107: 13294-9, 2010.
Repp et al. "Genotyping by Multiplex Polymerase Chain Reaction for Detection of Endemic Hepatitis B Virus Transmission" J Clinical Microbiology (1993) 31:1095-1102.
Richardson, et al. Novel inhibition of archaeal family-D DNA polymerase by uracil. Nucleic acids research 41.7 (2013): 4207-4218.
Roche. Using Multiplex Identifier (MID) Adaptors for the GS FLX Titanium Chemistry Basic MID Set Genome Sequencer FLX System, Technical Bulletin 004-2009, (Apr. 1, 2009) pp. 1-7. URL:http://454.com/downloads/my454/documentation/technical-bulletins/TCB-09004 Using MultiplexIdentifierAdaptorsForTheGSFLXTitaniumSeriesChemistry-BasicMIDSet.pdf.
Roche. Using Multiplex Identifier (MID) Adaptors for the GS FLX Titanium Chemistry Extended MID Set Genome Sequencer FLX System, Technical Bulletin 005-2009, (Apr. 1, 2009) pp. 1-7. URL:http://454.com/downloads/my454/documentation/technical-bulletins/TCB-09005 UsingMultiplexIdentifierAdaptorsForTheGSFLXTitaniumChemistry-ExtendedMIDSet.pdf.
Rodrigue, S. et al. "Whole genome amplification and de novo assembly of single bacterial cells" PLoS One. Sep. 2, 2009;4(9):e6864. doi: 10.1371/journal.pone.0006864.
Rogozin, et al. A highly conserved family of inactivated archaeal B family DNA polymerases. Biol Direct. Aug. 6, 2008;3:32. doi: 10.1186/1745-6150-3-32.
Ropers. New perspectives for the elucidation of genetic disorders. Am J Hum Genet. Aug. 2007;81(2):199-207. Epub Jun. 29, 2007.
Rotem, et al. High-Throughput Single-Cell Labeling (Hi-SCL) for RNA-Seq Using Drop-Based Microfluidics. PLoS One. May 22, 2015;10(5):e0116328. doi: 10.1371/journal.pone.0116328. eCollection 2015.
Rotem, et al. Single Cell Chip-Seq Using Drop-Based Microfluidics. Abstract #50. Frontiers of Single Cell Analysis, Stanford University Sep. 5-7, 2013.
Rotem, et al. Single-cell ChIP-seq reveals cell subpopulations defined by chromatin state. Nat Biotechnol. Nov. 2015;33(11):1165-72. doi: 10.1038/nbt.3383. Epub Oct. 12, 2015.
Ryan, "Rapid assay for mycobacterial growth and antibiotic susceptibility using gel microdrop and encapsulation", J. Clinical Microbial., 33:7 1720-1726 (1995).
Sakaguchi, et al. (1996) Cautionary Note on the Use of dUMP-Containing PCR Primers with PFU and VentR. Biotechniques, 21(3): 369-370 (Year: 1996).
Sander JD, et al. Selection-free zinc-finger-nuclease engineering by context-dependent assembly (CoDA). Nat. Methods. 2011;8:67-69.

Savva, et al. The structural basis of specific base-excision repair by uracil-DNA glycosylase. Nature. Feb. 9, 1995;373(6514):487-93.
Schirinzi et al., Combinatorial sequencing-by-hybridization: Analysis of the NF1 gene. Genet Test. 2006 Spring;10(1):8-17.
Schmeider, et al. Fast identification and removal of sequence contamination from genomic and metagenomic datasets. PLoS One. Mar. 9, 2011;6(3):e17288. doi: 10.1371/journal.pone.0017288.
Schmitt, "Bead-based multiplex genotyping of human papillomaviruses", J. Clinical Microbial., 44:2 504-512 (2006).
Schubert, et al. Microemulsifying fluorinated oils with mixtures of fluorinated and hydrogenated surfactants. Colloids and Surfaces A; Physicochemical and Engineering Aspects, 84(1994) 97-106.
Schwartz, et al., "Capturing native long-range contiguity by in situ library construction and optical sequencing", PNAS (Nov. 2012), 109(46)18749-18754.
Sebat, et al. Strong association of de novo numbers mutations with autism. Science. Apr. 20, 2007;316(5823):445-9. Epub Mar. 15, 2007.
Seiffert, et al. Smart microgel capsules from macromolecular precursors. J Am Chem Soc. May 12, 2010;132(18):6606-9. doi: 10.1021/ja102156h.
Shah, "Fabrication of mono disperse thermosensitive microgels and gel capsules in micro fluidic devices", Soft Matter, 4:2303-2309 (2008).
Shahi, et al. Abseq: Ultrahigh-throughput single cell protein profiling with droplet microfluidic barcoding. Sci Rep. 2017; 7: 44447. Published online Mar. 14, 2017. doi: 10.1038/srep44447.
Shaikh, et al. A modular microfluidic architecture for integrated biochemical analysis. Proc Natl Acad Sci U S A. Jul. 12, 2005;102(28):9745-50. Epub Jun. 28, 2005.
Shimkus, et al. A chemically cleavable biotinylated nucleotide: usefulness in the recovery of protein-DNA complexes from avidin affinity columns. Proc Natl Acad Sci U S A. May 1985;82(9):2593-7.
Shlien, et al. Number variations and cancer. Genome Med. Jun. 16, 2009;1(6):62. doi: 10.1186/gm62.
Shlien, et al. Excessive genomic DNA number variation in the Li-Fraumeni cancer predisposition syndrome. Proc Natl Acad Sci U S A. Aug. 12, 2008;105(32):11264-9. doi: 10.1073/pnas.0802970105. Epub Aug 6, 2008.
Shuttleworth, et al. Recognition of the pro-mutagenic base uracil by family B DNA polymerases from archaea. J Mol Biol. Mar. 26, 2004;337(3):621-34.
Sigma. Streptavidin-agarose (S1638) product information sheet. www.sigma-aldrich.com.
Simeonov et al., Single nucleotide polymorphism genotyping using short, fluorescently labeled locked nucleic acid (LNA) probes and fluorescence polarization detection. Nucleic Acids Res. Sep. 1, 2002;30(17):e91.
Simon, et al., "Using formaldehyde-assisted isolation of regulatory elements (FAIRE) to isolate active regulatory DNA", Nature Protocols, 2012, 7(2): 256-267.
Skerra. Phosphorothioate primers improve the amplification of DNA sequences by DNA polymerases with proofreading activity. Nucleic Acids Res. Jul. 25, 1992; 20(14):3551-4.
Smith, et al. Highly-multiplexed barcode sequencing: an efficient method for parallel analysis of pooled samples. Nucleic Acids Research, 38(13): e142 (2010).
Song, et al., "DNase-seq: A High-Resolution Technique for Mapping Active Gene Regulatory Elements across the Senome from Mammalian Cells", Cold Spring Harbor Laboratory Press, 2010, 2010(2), doi:10.1101/pdb.prot5384.
Song, et al. Reactions in droplets in microfluidic channels. Angew Chem Int Ed Engl. Nov. 13, 2006;45(44):7336-56.
Sorokin et al., Discrimination between perfect and mismatched duplexes with oligonucleotide gel microchips: role of thermodynamic and kinetic effects during hybridization. J Biomol Struct Dyn. Jun. 2005;22(6):725-34.
Holmberg, et al. The biotin-streptavidin interaction can be reversibly broken using water at elevated temperatures. Feb. 2, 2005. Electrophoresis, 26:501-510.
Invitrogen Dynal. Dynabeads M-280 Streptavidin 2006 product sheet.

(56) References Cited

OTHER PUBLICATIONS

Morton. Parameters of the human genome. Apr. 23, 1991. Proceedings of the National Academy of Sciences of the United States of America, 88: 7474-7476.
National Human Genome Research Institute (NHGRI). The Human Genome Project Completion: Frequently Asked Questions. Last Updated: Oct. 30, 2010 . . . .
Qiagen. Omniscript Reverse Transcription Handbook. Oct. 2010.
Seiffert, et al. Microfluidic fabrication of smart microgels from macromolecular precursors. 2010. Polymer.
Spormann Laboratory, Polymerase Chain Reaction (PCR), Alfred Spormann Laboratory, 2009, 1-3. (Year: 2009).
Stoeckius, et al. Large-scale simultaneous measurement of epitopes and transcriptomes in single cells. bioRxiv 113068; doi: https://doi.org/10.1101/113068.
Stoeckius, et al. Simultaneous epitope and transcriptome measurement in single cells. Nature methods. Jul. 31, 2017. Supplemental Materials.
Su, et al., Microfluidics-Based Biochips: Technology Issues, Implementation Platforms, and Design-Automation Challenges. IEEE Transactions on Computer-Aided Design of Integrated Circuits and Systems. 2006;25(2):211-23. (Feb. 2006).
Sun et al., Progress in research and application of liquid-phase chip technology. Chinese Journal Experimental Surgery. May 2005;22(5):639-40.
Susaki, et al. Whole-brain imaging with single-cell resolution using chemical cocktails and computational analysis. Cell. Apr. 24, 2014;157(3):726-39. doi: 10.1016/j.cell.2014.03.042. Epub Apr. 17, 2014.
Syed, et al. Next-generation sequencing library preparation: simultaneous fragmentation and tagging using in vitro transposition. Nature Methods 2 pgs (Nov. 2009).
Tawfik, D.S., et al., "Man-made cell-like compartments for molecular evolution," Nature Biotechnology, vol. 16, pp. 652-656 (1998) .
Tayyab, S. et al. "Size exclusion chromatography and size exclusion HPLC of proteins" Biochem Ed, Pergamon, (1991) 19(3):149-152.
Tewhey, et al. Microdroplet-based PCR amplification for large-scale targeted sequencing. Nat Biotechnol. Nov. 2009;27(11):1025-31. doi: 10.1038/nbt.1583. Epub Nov. 1, 2009.
Tewhey et al., Supplementary Materials, Nature Biotechnology, 2009, 27(11), 1-22.
Thaxton, C.S. et al. "A Bio-Bar-Code Assay Based Upon Dithiothreitol Oligonucleotide Release" Anal Chem (2005) 77:8174-8178.
Theberge, et al. Microdroplets in microfluidics: an evolving platform for discoveries in chemistry and biology. Angew Chem Int Ed Engl. Aug. 9, 2010;49(34):5846-68. doi: 10.1002/anie.200906653.
ThermoFisher, Protocols, M-270 Streptavidin, ThermoFisherScientific, 2007, 1-5. (Year: 2007).
Thorsen, et al. Dynamic pattern formation in a vesicle-generating microfluidic device. Physical Review Letters. American Physical Society. 2001; 86(18):4163-4166.
Tomer, et al. Advanced Clarity for rapid and high-resolution imaging of intact tissues. Nat Protoc. Jul. 2014;9(7):1682-97. doi: 10.1038/nprot.2014.123. Epub Jun. 19, 2014.
Tonelli, et al. Perfluoropolyether functional oligomers: unusual reactivity in organic chemistry. Journal of fluorine chemistry. 2002; 118(1)"107-121.
Tubeleviciute, et al. Compartmentalized self-replication (CSR) selection of Thermococcus litoralis Sh1B DNa polymerase for diminished uracil binding. Protein Eng Des Sel. Aug. 2010;23(8):589-97. doi: 10.1093/protein/gzq032. Epub May 31, 2010.
Turner, et al. Assaying chromosomal inversions by single-molecule haplotyping. Nat Methods. Jun. 2006;3(6):439-45.
Turner, et al, "High-throughput haplotype determination over long distances by haplotype fusion PCR and ligation haplotyping", Nat Protoc., 4:1771-83, 2009.
Turner, et al. Methods for genomic partitioning. Annu Rev Genomics Hum Genet. 2009;10:263-84. doi: 10.1146/annurev-genom-082908-150112. Review.
Ullal et al. Cancer Cell Profiling by Barcoding Allows Multiplexed Protein Analysis in Fine-Needle Aspirates. Sci Transl Med. Jan. 15, 2014; 6(219): 219ra9.
Ushijima et al, Detection and interpretation of altered methylation patterns in cancer cells, 2005, Nature reviews, 5, 223-231.
Van Nieuwerburgh, et al, "Illumina mate-paired DNA sequencing-library preparation using Cre-Lox recombination", Nucleic Acids Res., 40:1-8, 2012.
Wagner, et al. Biocompatible fluorinated polyglycerols for droplet microfluidics as an alternative to PEG-based copolymer surfactants. Lab Chip. Jan. 7, 2016;16(1):65-9. doi: 10.1039/c51c00823a. Epub Dec. 2, 2015.
Wang, et al. A novel thermo-induced self-bursting microcapsule with magnetic-targeting property. Chemphyschem. Oct. 5, 2009;10(14):2405-9.
Wang, et al. Digital karyotyping. Proc Natl Acad Sci U S A. Dec. 10, 2002;99(25):16156-61. Epub Dec. 2, 2002.
Wang et al., "Self-Formed Adaptor PCR: a Simple and Efficient Method for Chromosome Walking", Applied and Environmental Microbiology (Aug. 2007), 73(15):5048-5051.
Wang et al., Single nucleotide polymorphism discrimination assisted by improved base stacking hybridization using oligonucleotide microarrays. Biotechniques. 2003;35:300-08.
Ward, et al. Microfluidic flow focusing: Drop size and scaling in pressure versus flow-rate-driven pumping. Electrophoresis. Oct. 2005;26(19):3716-24.
Weaver, "Rapid clonal growth measurements at the single-cell level: gel microdroplets and flow cytometry", Biotechnology, 9:873-877 (1991).
Weigl, et al. Microfluidic Diffusion-Based Separation and Detection. Science. 1999; pp. 346-347.
Wesolowska, et al. Cost-effective multiplexing before capture allows screening of 25 000 clinically relevant SNPs in childhood acute lymphoblastic leukemia. Leukemia. Jun. 2011;25(6):1001-6. doi: 10.1038/leu.2011.32. Epub Mar. 18, 2011.
Whitesides, "Soft lithography in biology and biochemistry", Annual Review of Biomedical Engineering, 3:335-373 (2001).
Williams, et al. Amplification of complex gene libraries by emulsion PCR. Nature Methods. 2006;3(7):545-50.
Wiseman, R.W. et al. "Major histocompatibility complex genotyping with massively parallel pyrosequencing" Nature Medicine (Oct. 11, 2009) 15(11):1322-1326.
Wong, et al. Multiplexed Barcoded CRISPR-Cas9 Screening Enabled by CombiGEM. PNAS. Mar. 1, 2016, vol. 113, pp. 2544-2549.
Woo, et al. G/C-modified oligodeoxynucleotides with selective complementarity: synthesis and hybridization properties. Nucleic Acids Res. Jul. 1, 1996;24(13):2470-5.
Wood AJ, et al. Targeted genome editing across species using ZFNs and TALENs. Science. 2011;333:307.
Xi, et al. New library construction method for single-cell genomes. PLoS One. Jul. 19, 2017;12(7):e0181163. doi: 10.1371/journal.pone.0181163. eCollection 2017.
Xia and Whitesides, Soft Lithography, Angew. Chem. Int. Ed. 37:550-575 (1998).
Xia and Whitesides, Soft Lithography, Ann. Rev. Mat. Sci. 28:153-184 (1998).
Xiao, et al, "Determination of haplotypes from single DNA molecules: a method for single-molecule barcoding", Hum Mutat., 28:913-21, 2007.
Yamamoto, et al. Chemical modification of Ce(IV)/EDTA-base artificial restriction DNA cutter for versatile manipulation of double-stranded DNA. Nucleic Acids Research. 2007; 35(7):e53.
Yan, Pu et al. "Rapid one-step construction of hairpin RNA" Biochem and Biophys Res Comm (Jun. 12, 2009) 383(4):464-468.
Zeng, et al. High-performance single cell genetic analysis using microfluidic emulsion generator arrays. Anal Chem. Apr. 15, 2010;82(8):3183-90. doi: 10.1021/ac902683t.
Zentner, et al. Surveying the epigenomic landscape, one base at a time. Genome Biol. Oct. 22, 2012;13(10):250. doi: 10.1186/gb4051.
Zhang, "Combinatorial marking of cells and organelles with reconstituted fluorescent proteins", Cell, 119:137-144 (Oct. 1, 2004).
Zhang, et al. Degradable disulfide core-cross-linked micelles as a drug delivery system prepared from vinyl functionalized nucleosides

(56) References Cited

OTHER PUBLICATIONS via the RAFT process. Biomacromolecules. Nov. 2008;9(11):3321-31. doi: 10.1021/bm800867n. Epub Oct. 9, 2008.

Zhang, et al. One-step fabrication of supramolecular microcapsules from microfluidic droplets. Science. Feb. 10, 2012;335(6069):690-4. doi: 10.1126/science.1215416.

Zhang, et al. Reconstruction of DNA sequencing by hybridization. Bioinformatics. Jan. 2003;19(1):14-21.

Zhang F, et al. Efficient construction of sequence-specific TAL effectors for modulating mammalian transcription. Nat. Biotechnol. 2011;29:149-153.

Zhang. Genomics of inherited bone marrow failure and myelodysplasia. Dissertation [online]. University of Washington. 2015 [Retrieved on May 3, 2017].

Zhao, J., et al., "Preparation of hemoglobin-loaded Nano-sized particles with porous structure as oxygen carriers," Biomaterials, vol. 28, pp. 1414-1422 (2007).

Zheng, et al. Massively parallel digital transcriptional profiling of single cells. Nat Commun. Jan. 16, 2017;8:14049. doi: 10.1038/ncomms14049.

Zheng, X.Y. et al. "Haplotyping germline and cancer genomes with high-throughput linked-read sequencing" Nature Biotech (Feb. 1, 2016) 34(3):303-311.

Zhou, Y. et al. "Development of an enzyme activity screening system for p-glucosidase-displaying yeasts using calcium alginate micro-beads and flow sorting" Appl Microbiol Biotechnol (2009) 84:375-382 (Year: 2009).

Zhu et al. Hydrogel Droplet Microfluidics for High-Throughput Single Molecule/Cell Analysis. Accounts of Chemical Research Article ASAP. DOI: 10.1021/acs.accounts.6b00370.

Zhu, et al. Reverse transcriptase template switching: a SMART approach for full-length cDNA library constqruction. Biotechniques. Apr. 2001;30(4):892-7.

Zhu, et al. Synthesis and self-assembly of highly incompatible polybutadienepoly(hexafluoropropoylene oxide) diblock copolymers. Journal of Polymer Science Part B: Polymer Physics. 2005; 43(24):3685-3694.

Zimmermann et at., Microscale production of hybridomas by hypo-osmolar electrofusion. Hum• Antibodies Hybridomas. Jan. 1992;3 (1 ): 14-8.

Zong et al. Genome-Wide Detection of Single Nucleotide and Number Variations of a Single Human Cell. Science 338(6114):1622-1626 (2012).

\* cited by examiner

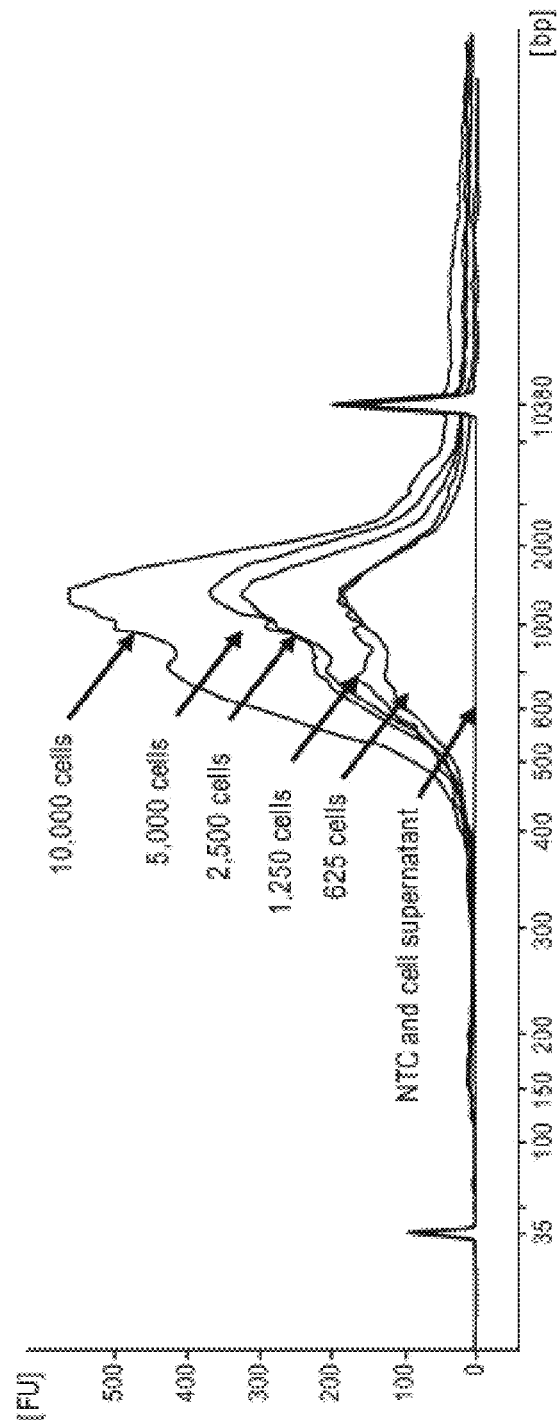

METHODS AND SYSTEMS FOR PROCESSING POLYNUCLEOTIDES

CROSS-REFERENCE TO RELATED APPLICATIONS

This application is a continuation of U.S. application Ser. No. 16/231,185, filed Dec. 21, 2018, which is a continuation of U.S. application Ser. No. 16/212,441, filed Dec. 6, 2018, which is a continuation of U.S. application Ser. No. 16/052,431, filed Aug. 1, 2018, which is a continuation-in-part of U.S. application Ser. No. 16/000,803, filed Jun. 5, 2018, which is a continuation of U.S. application Ser. No. 15/850,241, filed Dec. 21, 2017, which is a continuation of U.S. patent application Ser. No. 15/588,519, filed May 5, 2017, now U.S. Pat. No. 9,856,530, which is a continuation of U.S. patent application Ser. No. 15/376,582, filed Dec. 12, 2016, now U.S. Pat. No. 9,701,998, which is a continuation-in-part of U.S. patent application Ser. No. 14/104,650, filed on Dec. 12, 2013, now U.S. Pat. No. 9,567,631, which claims priority to U.S. Provisional Application No. 61/737,374, filed on Dec. 14, 2012; U.S. patent application Ser. No. 15/376,582 is also a continuation-in-part of U.S. patent application Ser. No. 14/250,701, filed on Apr. 11, 2014, which is a continuation of U.S. patent application Ser. No. 14/175,973, filed on Feb. 7, 2014, now U.S. Pat. No. 9,388,465, which claims priority to U.S. Provisional Application No. 61/844,804, filed on Jul. 10, 2013, U.S. Provisional Application No. 61/840,403, filed on Jun. 27, 2013, U.S. Provisional Application No. 61/800,223, filed on Mar. 15, 2013, and U.S. Provisional Application No. 61/762,435, filed on Feb. 8, 2013; U.S. application Ser. No. 16/052,431 is also a continuation-in-part of U.S. application Ser. No. 15/598,898, filed May 18, 2017, which is a continuation of U.S. application Ser. No. 14/624,468, filed Feb. 17, 2015, now U.S. Pat. No. 9,689,024, which is a division of U.S. patent application Ser. No. 13/966,150, filed Aug. 13, 2013, which claims priority to U.S. Provisional Application No. 61/683,192, filed Aug. 14, 2012, U.S. Provisional Application No. 61/737,374, filed Dec. 14, 2012, U.S. Provisional Application No. 61/762,435, filed Feb. 8, 2013, U.S. Provisional Application No. 61/800,223, filed Mar. 15, 2013, U.S. Provisional Application No. 61/840,403, filed Jun. 27, 2013, and U.S. Provisional Application No. 61/844,804, filed Jul. 10, 2013; U.S. application Ser. No. 16/231,185 is also a continuation-in-part of U.S. application Ser. No. 15/847,752, filed Dec. 19, 2017, which is a continuation of U.S. application Ser. No. 15/717,871, filed Sep. 27, 2017, now U.S. Pat. No. 9,951,386, which is a continuation-in-part of U.S. application Ser. No. 14/752,641, filed Jun. 26, 2015, which claims the benefit of U.S. Provisional Application No. 62/061,567, filed Oct. 8, 2014, and U.S. Provisional Application No. 62/017,558, filed Jun. 26, 2014; U.S. application Ser. No. 16/231,185 is also a continuation-in-part of U.S. application Ser. No. 16/052,486, which is a continuation-in-part of each of U.S. application Ser. No. 16/000,803 (which priority is recited above) and U.S. application Ser. No. 14/316,447, filed Jun. 26, 2014, which is a continuation-in-part of U.S. patent application Ser. No. 13/966,150 (which priority is recited above), filed Aug. 13, 2013, and a continuation-in-part of PCT/US13/54797, filed Aug. 13, 2013, which application claims the benefit of U.S. Provisional Application No. 61/683,192, filed on Aug. 14, 2012, U.S. Provisional Application No. 61/737,374, filed Dec. 14, 2012, U.S. Provisional Application No. 61/762,435, filed Feb. 8, 2013, U.S. Provisional Application No. 61/800,223, filed Mar. 15, 2013, U.S. Provisional Application No. 61/840,403 filed Jun. 27, 2013, and U.S. Provisional Application No. 61/844,804, filed Jul. 10, 2013; U.S. application Ser. No. 14/316,447 also claims the benefit of U.S. Provisional Application No. 61/896,060, filed Oct. 26, 2013, U.S. Provisional Application No. 61/909,974, filed Nov. 27, 2013, U.S. Provisional Application No. 61/991,018, filed May 9, 2014, U.S. Provisional Application No. 61/937,344, filed Feb. 7, 2014, and U.S. Provisional Application No. 61/940,318, filed Feb. 14, 2014; each of which applications is entirely incorporated herein by reference for all purposes.

BACKGROUND

Significant advances in analyzing and characterizing biological and biochemical materials and systems have led to unprecedented advances in understanding the mechanisms of life, health, disease and treatment. Among these advances, technologies that target and characterize the genomic make up of biological systems have yielded some of the most groundbreaking results, including advances in the use and exploitation of genetic amplification technologies, and nucleic acid sequencing technologies.

Nucleic acid sequencing can be used to obtain information in a wide variety of biomedical contexts, including diagnostics, prognostics, biotechnology, and forensic biology. Sequencing may involve basic methods including Maxam-Gilbert sequencing and chain-termination methods, or de novo sequencing methods including shotgun sequencing and bridge PCR, or next-generation methods including polony sequencing, 454 pyrosequencing, Illumina sequencing, SOLiD sequencing, Ion Torrent semiconductor sequencing, HeliScope single molecule sequencing, SMRT® sequencing, and others.

Despite these advances in biological characterization, many challenges still remain unaddressed, or relatively poorly addressed by the solutions currently being offered. The present disclosure provides novel solutions and approaches to addressing many of the shortcomings of existing technologies.

BRIEF SUMMARY

Provided herein are methods, compositions and systems for analyzing individual cells or small populations of cells, including the analysis and attribution of nucleic acids from and to these individual cells or cell populations.

An aspect of the disclosure provides a method of analyzing nucleic acids from cells that includes providing nucleic acids derived from an individual cell into a discrete partition; generating one or more first nucleic acid sequences derived from the nucleic acids within the discrete partition, which one or more first nucleic acid sequences have attached thereto oligonucleotides that comprise a common nucleic acid barcode sequence; generating a characterization of the one or more first nucleic acid sequences or one or more second nucleic acid sequences derived from the one or more first nucleic acid sequences, which one or more second nucleic acid sequences comprise the common barcode sequence; and identifying the one or more first nucleic acid sequences or one or more second nucleic acid sequences as being derived from the individual cell based, at least in part, upon a presence of the common nucleic acid barcode sequence in the generated characterization.

In some embodiments, the discrete partition is a discrete droplet. In some embodiments, the oligonucleotides are co-partitioned with the nucleic acids derived from the individual cell into the discrete partition. In some embodiments, at least 10,000, at least 100,000 or at least 500,000 of the oligonucleotides are co-partitioned with the nucleic acids derived from the individual cell into the discrete partition.

In some embodiments, the oligonucleotides are provided attached to a bead, where each oligonucleotide on a bead comprises the same barcode sequence, and the bead is co-partitioned with the individual cell into the discrete partition. In some embodiments, the oligonucleotides are releasably attached to the bead. In some embodiments, the bead comprises a degradable bead. In some embodiments, prior to or during generating the one or more first nucleic acid sequences the method includes releasing the oligonucleotides from the bead via degradation of the bead. In some embodiments, prior to generating the characterization, the method includes releasing the one or more first nucleic acid sequences from the discrete partition.

In some embodiments, generating the characterization comprises sequencing the one or more first nucleic acid sequences or the one or more second nucleic acid sequences. The method may also include assembling a contiguous nucleic acid sequence for at least a portion of a genome of the individual cell from sequences of the one or more first nucleic acid sequences or the one or more second nucleic acid sequences. Moreover, the method may also include characterizing the individual cell based upon the nucleic acid sequence for at least a portion of the genome of the individual cell.

In some embodiments, the nucleic acids are released from the individual cell in the discrete partition. In some embodiments, the nucleic acids comprise ribonucleic acid (RNA), such as, for example, messenger RNA (mRNA). In some embodiments, generating one or more first nucleic acid sequences includes subjecting the nucleic acids to reverse transcription under conditions that yield the one or more first nucleic acid sequences. In some embodiments, the reverse transcription occurs in the discrete partition. In some embodiments, the oligonucleotides are provided in the discrete partition and include a poly-T sequence. In some embodiments, the reverse transcription comprises hybridizing the poly-T sequence to at least a portion of each of the nucleic acids and extending the poly-T sequence in template directed fashion. In some embodiments, the oligonucleotides include an anchoring sequence that facilitates hybridization of the poly-T sequence. In some embodiments, the oligonucleotides include a random priming sequence that can be, for example, a random hexamer. In some embodiments, the reverse transcription comprises hybridizing the random priming sequence to at least a portion of each of the nucleic acids and extending the random priming sequence in template directed fashion.

In some embodiments, a given one of the one or more first nucleic acid sequences has sequence complementarity to at least a portion of a given one of the nucleic acids. In some embodiments, the discrete partition at most includes the individual cell among a plurality of cells. In some embodiments, the oligonucleotides include a unique molecular sequence segment. In some embodiments, the method can include identifying an individual nucleic acid sequence of the one or more first nucleic acid sequences or of the one or more second nucleic acid sequences as derived from a given nucleic acid of the nucleic acids based, at least in part, upon a presence of the unique molecular sequence segment. In some embodiments, the method includes determining an amount of the given nucleic acid based upon a presence of the unique molecular sequence segment.

In some embodiments, the method includes, prior to generating the characterization, adding one or more additional sequences to the one or more first nucleic acid sequences to generate the one or more second nucleic acid sequences. In some embodiments, the method includes adding a first additional nucleic acid sequence to the one or more first nucleic acid sequences with the aid of a switch oligonucleotide. In some embodiments, the switch oligonucleotide hybridizes to at least a portion of the one or more first nucleic acid sequences and is extended in a template directed fashion to couple the first additional nucleic acid sequence to the one or more first nucleic acid sequences. In some embodiments, the method includes amplifying the one of more first nucleic acid sequences coupled to the first additional nucleic acid sequence. In some embodiments, the amplifying occurs in the discrete partition. In some embodiments, the amplifying occurs after releasing the one or more first nucleic acid sequences coupled to the first additional nucleic acid sequence from the discrete partition.

In some embodiments, after the amplifying, the method includes adding one or more second additional nucleic acid sequences to the one or more first nucleic acid sequences coupled to the first additional sequence to generate the one or more second nucleic acid sequences. In some embodiments, the adding the one or more second additional sequences includes removing a portion of each of the one or more first nucleic acid sequences coupled to the first additional nucleic acid sequence and coupling thereto the one or more second additional nucleic acid sequences. In some embodiments, the removing is completed via shearing of the one or more first nucleic acid sequences coupled (e.g., ligated) to the first additional nucleic acid sequence.

In some embodiments, prior to generating the characterization, the method includes subjecting the one or more first nucleic acid sequences to transcription to generate one or more RNA fragments. In some embodiments, the transcription occurs after releasing the one or more first nucleic acid sequences from the discrete partition. In some embodiments, the oligonucleotides include a T7 promoter sequence. In some embodiments, prior to generating the characterization, the method includes removing a portion of each of the one or more RNA sequences and coupling an additional sequence to the one or more RNA sequences. In some embodiments, prior to generating the characterization, the method includes subjecting the one or more RNA sequences coupled to the additional sequence to reverse transcription to generate the one or more second nucleic acid sequences. In some embodiments, prior to generating the characterization, the method includes amplifying the one or more second nucleic acid sequences. In some embodiments, prior to generating the characterization, the method includes subjecting the one or more RNA sequences to reverse transcription to generate one or more DNA sequences. In some embodiments, prior to generating the characterization, the method includes removing a portion of each of the one or more DNA sequences and coupling one or more additional sequences to the one or more DNA sequences to generate the one or more second nucleic acid sequences. In some embodiments, prior to generating the characterization, the method includes amplifying the one or more second nucleic acid sequences.

In some embodiments, the nucleic acids include complementary (cDNA) generated from reverse transcription of RNA from the individual cell. In some embodiments, the oligonucleotides include a priming sequence and are provided in the discrete partition. In some embodiments, the priming sequence includes a random N-mer. In some embodiments, generating the one or more first nucleic acid sequences includes hybridizing the priming sequence to the cDNA and extending the priming sequence in template directed fashion.

In some embodiments, the discrete partition includes switch oligonucleotides comprising a complement sequence of the oligonucleotides. In some embodiments, generating the one or more first nucleic acid sequences includes hybridizing the switch oligonucleotides to at least a portion of nucleic acid fragments derived from the nucleic acids and extending the switch oligonucleotides in template directed fashion. In some embodiments, generating the one or more first nucleic acid sequences includes attaching the oligonucleotides to the one or more first nucleic acid sequences. In some embodiments, the one or more first nucleic acid sequences are nucleic acid fragments derived from the nucleic acids. In some embodiments, generating the one or more first nucleic acid sequences includes coupling (e.g., ligating) the oligonucleotides to the nucleic acids.

In some embodiments, a plurality of partitions comprises the discrete partition. In some embodiments, the plurality of partitions, on average, comprises less than one cell per partition. In some embodiments, less than 25% of partitions of the plurality of partitions do not comprise a cell. In some embodiments, the plurality of partitions comprises discrete partitions each having at least one partitioned cell. In some embodiments, fewer than 25%, fewer than 20%, fewer than 15%, fewer than 10%, fewer than 5% or fewer than 1% of the discrete partitions comprise more than one cell. In some embodiments, at least a subset of the discrete partitions comprises a bead. In some embodiments, at least 75%, at least 80%, at least 85%, at least 90%, at least 95% or at least 99% of the discrete partitions comprise at least one cell and at least one bead. In some embodiments, the discrete partitions include partitioned nucleic acid barcode sequences. In some embodiments, the discrete partitions include at least 1,000, at least 10,000, or at least 100,000 different partitioned nucleic acid barcode sequences. In some embodiments, the plurality of partitions comprises at least 1,000, at least 10,000 or at least 100,000 partitions.

In another aspect, the disclosure provides a method of characterizing cells in a population of a plurality of different cell types that includes providing nucleic acids from individual cells in the population into discrete partitions; attaching oligonucleotides that comprise a common nucleic acid barcode sequence to one or more fragments of the nucleic acids from the individual cells within the discrete partitions, where a plurality of different partitions comprise different common nucleic acid barcode sequences; and characterizing the one or more fragments of the nucleic acids from the plurality of discrete partitions, and attributing the one or more fragments to individual cells based, at least in part, upon the presence of a common barcode sequence; and characterizing a plurality of individual cells in the population based upon the characterization of the one or more fragments in the plurality of discrete partitions.

In some embodiments, the method includes fragmenting the nucleic acids. In some embodiments, the discrete partitions are droplets. In some embodiments, the characterizing the one or more fragments of the nucleic acids includes sequencing ribosomal deoxyribonucleic acid from the individual cells, and the characterizing the cells comprises identifying a cell genus, species, strain or variant. In some embodiments, the individual cells are derived from a microbiome sample. In some embodiments, the individual cells are derived from a human tissue sample. In some embodiments, the individual cells are derived from circulating cells in a mammal. In some embodiments, the individual cells are derived from a forensic sample. In some embodiments, the nucleic acids are released from the individual cells in the discrete partitions.

An additional aspect of the disclosure provides a method of characterizing an individual cell or population of cells that includes incubating a cell with a plurality of different cell surface feature binding group types, where each different cell surface feature binding group type is capable of binding to a different cell surface feature, and where each different cell surface binding group type comprises a reporter oligonucleotide associated therewith, under conditions that allow binding between one or more cell surface feature binding groups and its respective cell surface feature, if present; partitioning the cell into a partition that comprises a plurality of oligonucleotides comprising a barcode sequence; attaching the barcode sequence to oligonucleotide reporter groups present in the partition; sequencing the oligonucleotide reporter groups and attached barcodes; and characterizing cell surface features present on the cell based upon reporter oligonucleotides that are sequenced.

An additional aspect of the disclosure provides a composition comprising a plurality of partitions, each of the plurality of partitions comprising an individual cell and a population of oligonucleotides that comprise a common nucleic acid barcode sequence. In some embodiments, the plurality of partitions comprises droplets in an emulsion. In some embodiments, the population of oligonucleotides within each of the plurality of partitions is coupled to a bead disposed within each of the plurality of partitions. In some embodiments, the individual cell has associated therewith a plurality of different cell surface feature binding groups associated with their respective cell surface features and each different type of cell surface feature binding group includes an oligonucleotide reporter group comprising a different nucleotide sequence. In some embodiments, the plurality of different cell surface feature binding groups includes a plurality of different antibodies or antibody fragments having a binding affinity for a plurality of different cell surface features.

Additional aspects and advantages of the present disclosure will become readily apparent to those skilled in the art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIG. 14A-B provides illustrations of example yields from reverse transcription and cDNA amplification in partitions with various cell numbers.

DETAILED DESCRIPTION

Figure 1:
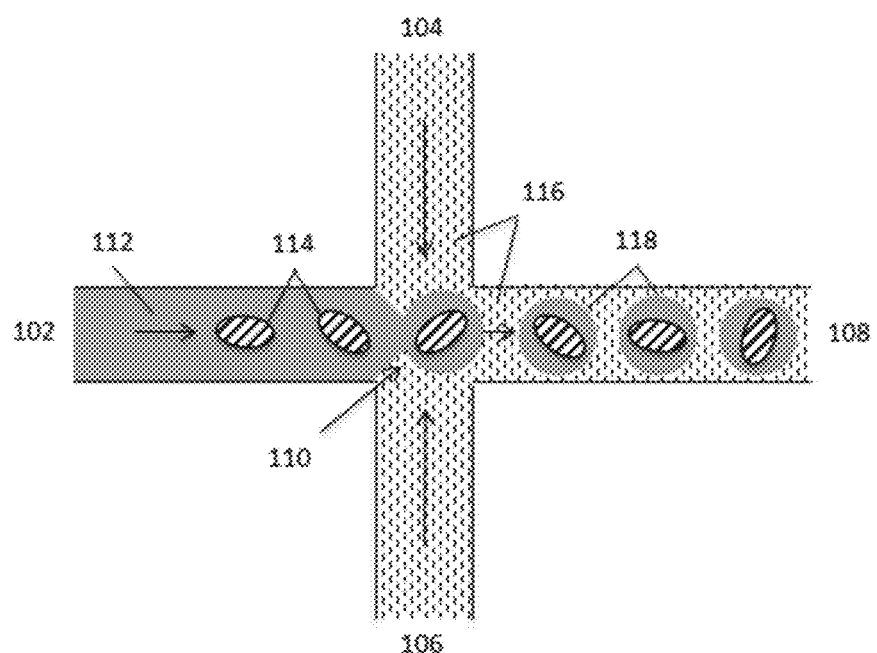
FIG. 1 schematically illustrates a microfluidic channel structure for partitioning individual or small groups of cells.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Where values are described as ranges, it will be understood that such disclosure includes the disclosure of all possible sub-ranges within such ranges, as well as specific numerical values that fall within such ranges irrespective of whether a specific numerical value or specific sub-range is expressly stated.

I. SINGLE CELL ANALYSIS

Advanced nucleic acid sequencing technologies have yielded monumental results in sequencing biological materials, including providing substantial sequence information on individual organisms, and relatively pure biological samples. However, these systems have not proven effective at being able to identify and characterize sub-populations of cells in biological samples that may represent a smaller minority of the overall make up of the sample, but for which individualized sequence information could prove even more valuable.

Most nucleic acid sequencing technologies derive the nucleic acids that they sequence from collections of cells derived from tissue or other samples. The cells can be processed, en masse, to extract the genetic material that represents an average of the population of cells, which can then be processed into sequencing ready DNA libraries that are configured for a given sequencing technology. As will be appreciated, although often discussed in terms of DNA or nucleic acids, the nucleic acids derived from the cells may include DNA, or RNA, including, e.g., mRNA, total RNA, or the like, that may be processed to produce cDNA for sequencing, e.g., using any of a variety of RNA-seq methods. Following from this processing, absent a cell specific marker, attribution of genetic material as being contributed by a subset of cells or all cells in a sample is virtually impossible in such an ensemble approach.

In addition to the inability to attribute characteristics to particular subsets of populations of cells, such ensemble sample preparation methods also are, from the outset, predisposed to primarily identifying and characterizing the majority constituents in the sample of cells, and are not designed to be able to pick out the minority constituents, e.g., genetic material contributed by one cell, a few cells, or a small percentage of total cells in the sample. Likewise, where analyzing expression levels, e.g., of mRNA, an ensemble approach would be predisposed to presenting potentially grossly inaccurate data from cell populations that are non-homogeneous in terms of expression levels. In some cases, where expression is high in a small minority of the cells in an analyzed population, and absent in the majority of the cells of the population, an ensemble method would indicate low level expression for the entire population.

This original majority bias is further magnified, and even overwhelming, through processing operations used in building up the sequencing libraries from these samples. In particular, most next generation sequencing technologies rely upon the geometric amplification of nucleic acid fragments, such as the polymerase chain reaction, in order to produce sufficient DNA for the sequencing library. However, such geometric amplification is biased toward amplification of majority constituents in a sample, and may not preserve the starting ratios of such minority and majority components. By way of example, if a sample includes 95% DNA from a particular cell type in a sample, e.g., host tissue cells, and 5% DNA from another cell type, e.g., cancer cells, PCR based amplification can preferentially amplify the majority DNA in place of the minority DNA, both as a function of comparative exponential amplification (the repeated doubling of the higher concentration quickly outpaces that of the smaller fraction) and as a function of sequestration of amplification reagents and resources (as the larger fraction is amplified, it preferentially utilizes primers and other amplification reagents).

While some of these difficulties may be addressed by utilizing different sequencing systems, such as single molecule systems that don't require amplification, the single molecule systems, as well as the ensemble sequencing methods of other next generation sequencing systems, can also have requirements for sufficiently large input DNA requirements. In particular, single molecule sequencing systems like the Pacific Biosciences SMRT Sequencing system can have sample input DNA requirements of from 500 nanograms (ng) to upwards of 10 micrograms (µg), which is far larger than what can be derived from individual cells or even small subpopulations of cells. Likewise, other NGS systems can be optimized for starting amounts of sample DNA in the sample of from approximately 50 ng to about 1 µg.

II. COMPARTMENTALIZATION AND CHARACTERIZATION OF CELLS

Disclosed herein, however, are methods and systems for characterizing nucleic acids from small populations of cells, and in some cases, for characterizing nucleic acids from individual cells, especially in the context of larger populations of cells. The methods and systems provide advantages of being able to provide the attribution advantages of the non-amplified single molecule methods with the high throughput of the other next generation systems, with the additional advantages of being able to process and sequence extremely low amounts of input nucleic acids derivable from individual cells or small collections of cells.

In particular, the methods described herein compartmentalize the analysis of individual cells or small populations of cells, including e.g., nucleic acids from individual cells or small groups of cells, and then allow that analysis to be attributed back to the individual cell or small group of cells from which the nucleic acids were derived. This can be accomplished regardless of whether the cell population represents a 50/50 mix of cell types, a 90/10 mix of cell types, or virtually any ratio of cell types, as well as a complete heterogeneous mix of different cell types, or any mixture between these. Differing cell types may include cells or biologic organisms from different tissue types of an individual, from different individuals, from differing genera, species, strains, variants, or any combination of any or all of the foregoing. For example, differing cell types may include normal and tumor tissue from an individual, multiple different bacterial species, strains and/or variants from environmental, forensic, microbiome or other samples, or any of a variety of other mixtures of cell types.

In one aspect, the methods and systems described herein, provide for the compartmentalization, depositing or partitioning of the nucleic acid contents of individual cells from a sample material containing cells, into discrete compartments or partitions (referred to interchangeably herein as partitions), where each partition maintains separation of its own contents from the contents of other partitions. Unique identifiers, e.g., barcodes, may be previously, subsequently or concurrently delivered to the partitions that hold the compartmentalized or partitioned cells, in order to allow for the later attribution of the characteristics of the individual cells to the particular compartment.

As used herein, in some aspects, the partitions refer to containers or vessels (such as wells, microwells, tubes, through ports in nanoarray substrates, e.g., BioTrove nanoarrays, or other containers). In many some aspects, however, the compartments or partitions comprise partitions that are flowable within fluid streams. These partitions may be comprised of, e.g., microcapsules or micro-vesicles that have an outer barrier surrounding an inner fluid center or core, or they may be a porous matrix that is capable of entraining and/or retaining materials within its matrix. In some aspects, however, these partitions comprise droplets of aqueous fluid within a non-aqueous continuous phase, e.g., an oil phase. A variety of different vessels are described in, for example, U.S. patent application Ser. No. 13/966,150, filed Aug. 13, 2013, the full disclosure of which is incorporated herein by reference in its entirety for all purposes. Likewise, emulsion systems for creating stable droplets in non-aqueous or oil continuous phases are described in detail in, e.g., U.S. Patent Publication No. 2010/0105112, the full disclosure of which is incorporated herein by reference in its entirety for all purposes.

In the case of droplets in an emulsion, allocating individual cells to discrete partitions may generally be accomplished by introducing a flowing stream of cells in an aqueous fluid into a flowing stream of a non-aqueous fluid, such that droplets are generated at the junction of the two streams. By providing the aqueous cell-containing stream at a certain concentration level of cells, one can control the level of occupancy of the resulting partitions in terms of numbers of cells. In some cases, where single cell partitions are desired, it may be desirable to control the relative flow rates of the fluids such that, on average, the partitions contain less than one cell per partition, in order to ensure that those partitions that are occupied, are primarily singly occupied. Likewise, one may wish to control the flow rate to provide that a higher percentage of partitions are occupied, e.g., allowing for only a small percentage of unoccupied partitions. In some aspects, the flows and channel architectures are controlled as to ensure a desired number of singly occupied partitions, less than a certain level of unoccupied partitions and less than a certain level of multiply occupied partitions.

In many cases, the systems and methods are used to ensure that the substantial majority of occupied partitions (partitions containing one or more microcapsules) include no more than 1 cell per occupied partition. In some cases, the partitioning process is controlled such that fewer than 25% of the occupied partitions contain more than one cell, and in many cases, fewer than 20% of the occupied partitions have more than one cell, while in some cases, fewer than 10% or even fewer than 5% of the occupied partitions include more than one cell per partition.

Additionally or alternatively, in many cases, it is desirable to avoid the creation of excessive numbers of empty partitions. While this may be accomplished by providing sufficient numbers of cells into the partitioning zone, the poissonian distribution would expectedly increase the number of partitions that would include multiple cells. As such, in accordance with aspects described herein, the flow of one or more of the cells, or other fluids directed into the partitioning zone are controlled such that, in many cases, no more than 50% of the generated partitions are unoccupied, i.e., including less than 1 cell, no more than 25% of the generated partitions, no more than 10% of the generated partitions, may be unoccupied. Further, in some aspects, these flows are controlled so as to present non-poissonian distribution of single occupied partitions while providing lower levels of unoccupied partitions. Restated, in some aspects, the above noted ranges of unoccupied partitions can be achieved while still providing any of the single occupancy rates described above. For example, in many cases, the use of the systems and methods described herein creates resulting partitions that have multiple occupancy rates of from less than 25%, less than 20%, less than 15%, less than 10%, and in many cases, less than 5%, while having unoccupied partitions of from less than 50%, less than 40%, less than 30%, less than 20%, less than 10%, and in some cases, less than 5%.

As will be appreciated, the above-described occupancy rates are also applicable to partitions that include both cells and beads carrying the barcode oligonucleotides. In particular, in some aspects, a substantial percentage of the overall occupied partitions will include both a bead and a cell. In particular, it may be desirable to provide that at least 50% of the partitions are occupied by at least one cell and at least one bead, or at least 75% of the partitions may be so occupied, or even at least 80% or at least 90% of the partitions may be so occupied. Further, in those cases where it is desired to provide a single cell and a single bead within a partition, at least 50% of the partitions can be so occupied, at least 60%, at least 70%, at least 80% or even at least 90% of the partitions can be so occupied.

Although described in terms of providing substantially singly occupied partitions, above, in certain cases, it is desirable to provide multiply occupied partitions, e.g., containing two, three, four or more cells and/or beads within a single partition. Accordingly, as noted above, the flow characteristics of the cell and/or bead containing fluids and partitioning fluids may be controlled to provide for such multiply occupied partitions. In particular, the flow parameters may be controlled to provide a desired occupancy rate at greater than 50% of the partitions, greater than 75%, and in some cases greater than 80%, 90%, 95%, or higher.

Additionally, in many cases, the multiple beads within a single partition may comprise different reagents associated therewith. In such cases, it may be advantageous to introduce different beads into a common channel or droplet generation junction, from different bead sources, i.e., containing different associated reagents, through different channel inlets into such common channel or droplet generation junction. In such cases, the flow and frequency of the different beads into the channel or junction may be controlled to provide for the desired ratio of microcapsules from each source, while ensuring the desired pairing or combination of such beads into a partition with the desired number of cells.

The partitions described herein are often characterized by having extremely small volumes, e.g., less than 10 less than 5 µL, less than 1 µL, less than 900 picoliters (pL), less than 800 pL, less than 700 pL, less than 600 pL, less than 500 pL, less than 400 pL, less than 300 pL, less than 200 pL, less than 100 pL, less than 50 pL, less than 20 pL, less than 10 pL, less than 1 pL, less than 500 nanoliters (nL), or even less than 100 nL, 50 nL, or even less.

For example, in the case of droplet based partitions, the droplets may have overall volumes that are less than 1000 pL, less than 900 pL, less than 800 pL, less than 700 pL, less than 600 pL, less than 500 pL, less than 400 pL, less than 300 pL, less than 200 pL, less than 100 pL, less than 50 pL, less than 20 pL, less than 10 pL, or even less than 1 pL. Where co-partitioned with beads, it will be appreciated that the sample fluid volume, e.g., including co-partitioned cells, within the partitions may be less than 90% of the above described volumes, less than 80%, less than 70%, less than 60%, less than 50%, less than 40%, less than 30%, less than 20%, or even less than 10% the above described volumes.

As is described elsewhere herein, partitioning species may generate a population of partitions. In such cases, any suitable number of partitions can be generated to generate the population of partitions. For example, in a method described herein, a population of partitions may be generated that comprises at least about 1,000 partitions, at least about 5,000 partitions, at least about 10,000 partitions, at least about 50,000 partitions, at least about 100,000 partitions, at least about 500,000 partitions, at least about 1,000,000 partitions, at least about 5,000,000 partitions at least about 10,000,000 partitions, at least about 50,000,000 partitions, at least about 100,000,000 partitions, at least about 500,000,000 partitions or at least about 1,000,000,000 partitions. Moreover, the population of partitions may comprise both unoccupied partitions (e.g., empty partitions) and occupied partitions In certain cases, microfluidic channel networks are particularly suited for generating partitions as described herein. Examples of such microfluidic devices include those described in detail in Provisional U.S. Patent Application No. 61/977,804, filed Apr. 4, 2014, the full disclosure of which is incorporated herein by reference in its entirety for all purposes. Alternative mechanisms may also be employed in the partitioning of individual cells, including porous membranes through which aqueous mixtures of cells are extruded into non-aqueous fluids. Such systems are generally available from, e.g., Nanomi, Inc.

An example of a simplified microfluidic channel structure for partitioning individual cells is illustrated in FIG. 1. As described elsewhere herein, in some cases, the majority of occupied partitions include no more than one cell per occupied partition and, in some cases, some of the generated partitions are unoccupied. In some cases, though, some of the occupied partitions may include more than one cell. In some cases, the partitioning process may be controlled such that fewer than 25% of the occupied partitions contain more than one cell, and in many cases, fewer than 20% of the occupied partitions have more than one cell, while in some cases, fewer than 10% or even fewer than 5% of the occupied partitions include more than one cell per partition. As shown, the channel structure can include channel segments 102, 104, 106 and 108 communicating at a channel junction 110. In operation, a first aqueous fluid 112 that includes suspended cells 114, may be transported along channel segment 102 into junction 110, while a second fluid 116 that is immiscible with the aqueous fluid 112 is delivered to the junction 110 from channel segments 104 and 106 to create discrete droplets 118 of the aqueous fluid including individual cells 114, flowing into channel segment 108.

In some aspects, this second fluid 116 comprises an oil, such as a fluorinated oil, that includes a fluorosurfactant for stabilizing the resulting droplets, e.g., inhibiting subsequent coalescence of the resulting droplets. Examples of particularly useful partitioning fluids and fluorosurfactants are described for example, in U.S. Patent Publication No. 2010/0105112, the full disclosure of which is hereby incorporated herein by reference in its entirety for all purposes.

In other aspects, in addition to or as an alternative to droplet based partitioning, cells may be encapsulated within a microcapsule that comprises an outer shell or layer or porous matrix in which is entrained one or more individual cells or small groups of cells, and may include other reagents. Encapsulation of cells may be carried out by a variety of processes. In general, such processes combine an aqueous fluid containing the cells to be analyzed with a polymeric precursor material that may be capable of being formed into a gel or other solid or semi-solid matrix upon application of a particular stimulus to the polymer precursor. Such stimuli include, e.g., thermal stimuli (either heating or cooling), photo-stimuli (e.g., through photo-curing), chemical stimuli (e.g., through crosslinking, polymerization initiation of the precursor (e.g., through added initiators), or the like.

Preparation of microcapsules comprising cells may be carried out by a variety of methods. For example, air knife droplet or aerosol generators may be used to dispense droplets of precursor fluids into gelling solutions in order to form microcapsules that include individual cells or small groups of cells. Likewise, membrane based encapsulation systems, such as those available from, e.g., Nanomi, Inc., may be used to generate microcapsules as described herein. In some aspects, microfluidic systems like that shown in FIG. 1 may be readily used in encapsulating cells as described herein. In particular, and with reference to FIG. 1, the aqueous fluid comprising the cells and the polymer precursor material is flowed into channel junction 110, where it is partitioned into droplets 118 comprising the individual cells 114, through the flow of non-aqueous fluid 116. In the case of encapsulation methods, non-aqueous fluid 116 may also include an initiator to cause polymerization and/or crosslinking of the polymer precursor to form the microcapsule that includes the entrained cells. Examples of particularly useful polymer precursor/initiator pairs include those described in, e.g., U.S. Patent Application Nos. 61/940,318, filed Feb. 7, 2014, 61/991,018, Filed May 9, 2014, and U.S. patent application Ser. No. 14/316,383, filed Jun. 26, 2014, the full disclosures of which are hereby incorporated herein by reference in their entireties for all purposes.

For example, in the case where the polymer precursor material comprises a linear polymer material, e.g., a linear polyacrylamide, PEG, or other linear polymeric material, the activation agent may comprise a cross-linking agent, or a chemical that activates a cross-linking agent within the formed droplets. Likewise, for polymer precursors that comprise polymerizable monomers, the activation agent may comprise a polymerization initiator. For example, in certain cases, where the polymer precursor comprises a mixture of acrylamide monomer with a N,N'-bis-(acryloyl) cystamine (BAC) comonomer, an agent such as tetraethylmethylenediamine (TEMED) may be provided within the second fluid streams in channel segments 104 and 106, which initiates the copolymerization of the acrylamide and BAC into a cross-linked polymer network or, hydrogel.

Upon contact of the second fluid stream 116 with the first fluid stream 112 at junction 110 in the formation of droplets, the TEMED may diffuse from the second fluid 116 into the aqueous first fluid 112 comprising the linear polyacrylamide, which will activate the crosslinking of the polyacrylamide within the droplets, resulting in the formation of the gel, e.g., hydrogel, microcapsules 118, as solid or semi-solid beads or particles entraining the cells 114. Although described in terms of polyacrylamide encapsulation, other 'activatable' encapsulation compositions may also be employed in the context of the methods and compositions described herein. For example, formation of alginate droplets followed by exposure to divalent metal ions, e.g., Ca2+, can be used as an encapsulation process using the described processes. Likewise, agarose droplets may also be transformed into capsules through temperature based gelling, e.g., upon cooling, or the like. As will be appreciated, in some cases, encapsulated cells can be selectively releasable from the microcapsule, e.g., through passage of time, or upon application of a particular stimulus, that degrades the microcapsule sufficiently to allow the cell, or its contents to be released from the microcapsule, e.g., into an additional partition, such as a droplet. For example, in the case of the polyacrylamide polymer described above, degradation of the microcapsule may be accomplished through the introduction of an appropriate reducing agent, such as DTT or the like, to cleave disulfide bonds that cross link the polymer matrix (See, e.g., U.S. Provisional Patent Application Nos. 61/940,318, filed Feb. 7, 2014, 61/991,018, Filed May 9, 2014, and U.S. patent application Ser. No. 14/316,383, filed Jun. 26, 2014, the full disclosures of which are hereby incorporated herein by reference in their entirety for all purposes.

As will be appreciated, encapsulated cells or cell populations provide certain potential advantages of being storable, and more portable than droplet based partitioned cells. Furthermore, in some cases, it may be desirable to allow cells to be analyzed to incubate for a select period of time, in order to characterize changes in such cells over time, either in the presence or absence of different stimuli. In such cases, encapsulation of individual cells may allow for longer incubation than simple partitioning in emulsion droplets, although in some cases, droplet partitioned cells may also be incubated form different periods of time, e.g., at least 10 seconds, at least 30 seconds, at least 1 minute, at least 5 minutes, at least 10 minutes, at least 30 minutes, at least 1 hour, at least 2 hours, at least 5 hours, or at least 10 hours or more. As alluded to above, the encapsulation of cells may constitute the partitioning of the cells into which other reagents are co-partitioned. Alternatively, encapsulated cells may be readily deposited into other partitions, e.g., droplets, as described above.

In accordance with certain aspects, the cells may be partitioned along with lysis reagents in order to release the contents of the cells within the partition. In such cases, the lysis agents can be contacted with the cell suspension concurrently with, or immediately prior to the introduction of the cells into the partitioning junction/droplet generation zone, e.g., through an additional channel or channels upstream of channel junction 110. Examples of lysis agents include bioactive reagents, such as lysis enzymes that are used for lysis of different cell types, e.g., gram positive or negative bacteria, plants, yeast, mammalian, etc., such as lysozymes, achromopeptidase, lysostaphin, labiase, kitalase, lyticase, and a variety of other lysis enzymes available from, e.g., Sigma-Aldrich, Inc. (St Louis, Mo.), as well as other commercially available lysis enzymes. Other lysis agents may additionally or alternatively be co-partitioned with the cells to cause the release of the cell's contents into the partitions. For example, in some cases, surfactant based lysis solutions may be used to lyse cells, although these may be less desirable for emulsion based systems where the surfactants can interfere with stable emulsions. In some cases, lysis solutions may include non-ionic surfactants such as, for example, TritonX-100 and Tween 20. In some cases, lysis solutions may include ionic surfactants such as, for example, sarcosyl and sodium dodecyl sulfate (SDS). Similarly, lysis methods that employ other methods may be used, such as electroporation, thermal, acoustic or mechanical cellular disruption may also be used in certain cases, e.g., non-emulsion based partitioning such as encapsulation of cells that may be in addition to or in place of droplet partitioning, where any pore size of the encapsulate is sufficiently small to retain nucleic acid fragments of a desired size, following cellular disruption.

In addition to the lysis agents co-partitioned with the cells described above, other reagents can also be co-partitioned with the cells, including, for example, DNase and RNase inactivating agents or inhibitors, such as proteinase K, chelating agents, such as EDTA, and other reagents employed in removing or otherwise reducing negative activity or impact of different cell lysate components on subsequent processing of nucleic acids. In addition, in the case of encapsulated cells, the cells may be exposed to an appropriate stimulus to release the cells or their contents from a co-partitioned microcapsule. For example, in some cases, a chemical stimulus may be co-partitioned along with an encapsulated cell to allow for the degradation of the microcapsule and release of the cell or its contents into the larger partition. In some cases, this stimulus may be the same as the stimulus described elsewhere herein for release of oligonucleotides from their respective bead or partition. In alternative aspects, this may be a different and non-overlapping stimulus, in order to allow an encapsulated cell to be released into a partition at a different time from the release of oligonucleotides into the same partition.

Additional reagents may also be co-partitioned with the cells, such as endonucleases to fragment the cell's DNA, DNA polymerase enzymes and dNTPs used to amplify the cell's nucleic acid fragments and to attach the barcode oligonucleotides to the amplified fragments. Additional reagents may also include reverse transcriptase enzymes, including enzymes with terminal transferase activity, primers and oligonucleotides, and switch oligonucleotides (also referred to herein as "switch oligos") which can be used for template switching. In some cases, template switching can be used to increase the length of a cDNA. In one example of template switching, cDNA can be generated from reverse transcription of a template, e.g., cellular mRNA, where a reverse transcriptase with terminal transferase activity can add additional nucleotides, e.g., polyC, to the cDNA that are not encoded by the template, such, as at an end of the cDNA. Switch oligos can include sequences complementary to the additional nucleotides, e.g. polyG. The additional nucleotides (e.g., polyC) on the cDNA can hybridize to the sequences complementary to the additional nucleotides (e.g., polyG) on the switch oligo, whereby the switch oligo can be used by the reverse transcriptase as template to further extend the cDNA. Switch oligos may comprise deoxyribonucleic acids, ribonucleic acids, modified nucleic acids including locked nucleic acids (LNA), or any combination.

In some cases, the length of a switch oligo may be 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250 nucleotides or longer.

In some cases, the length of a switch oligo may be at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249 or 250 nucleotides or longer.

In some cases, the length of a switch oligo may be at most 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249 or 250 nucleotides.

Once the contents of the cells are released into their respective partitions, the nucleic acids contained therein may be further processed within the partitions. In accordance with the methods and systems described herein, the nucleic acid contents of individual cells are generally provided with unique identifiers such that, upon characterization of those nucleic acids they may be attributed as having been derived from the same cell or cells. The ability to attribute characteristics to individual cells or groups of cells is provided by the assignment of unique identifiers specifically to an individual cell or groups of cells, which is another advantageous aspect of the methods and systems described herein. In particular, unique identifiers, e.g., in the form of nucleic acid barcodes are assigned or associated with individual cells or populations of cells, in order to tag or label the cell's components (and as a result, its characteristics) with the unique identifiers. These unique identifiers are then used to attribute the cell's components and characteristics to an individual cell or group of cells. In some aspects, this is carried out by co-partitioning the individual cells or groups of cells with the unique identifiers. In some aspects, the unique identifiers are provided in the form of oligonucleotides that comprise nucleic acid barcode sequences that may be attached to or otherwise associated with the nucleic acid contents of individual cells, or to other components of the cells, and particularly to fragments of those nucleic acids. The oligonucleotides are partitioned such that as between oligonucleotides in a given partition, the nucleic acid barcode sequences contained therein are the same, but as between different partitions, the oligonucleotides can, and do have differing barcode sequences, or at least represent a large number of different barcode sequences across all of the partitions in a given analysis. In some aspects, only one nucleic acid barcode sequence can be associated with a given partition, although in some cases, two or more different barcode sequences may be present.

The nucleic acid barcode sequences can include from 6 to about 20 or more nucleotides within the sequence of the oligonucleotides. In some cases, the length of a barcode sequence may be 6, 7, 8, 9, 10, 11, 12, 13, 14, 15, 16, 17, 18, 19, 20 nucleotides or longer. In some cases, the length of a barcode sequence may be at least 6, 7, 8, 9, 10, 11, 12, 13, 14, 15, 16, 17, 18, 19, 20 nucleotides or longer. In some cases, the length of a barcode sequence may be at most 6, 7, 8, 9, 10, 11, 12, 13, 14, 15, 16, 17, 18, 19, 20 nucleotides or shorter. These nucleotides may be completely contiguous, i.e., in a single stretch of adjacent nucleotides, or they may be separated into two or more separate subsequences that are separated by 1 or more nucleotides. In some cases, separated barcode subsequences can be from about 4 to about 16 nucleotides in length. In some cases, the barcode subsequence may be 4, 5, 6, 7, 8, 9, 10, 11, 12, 13, 14, 15, 16 nucleotides or longer. In some cases, the barcode subsequence may be at least 4, 5, 6, 7, 8, 9, 10, 11, 12, 13, 14, 15, 16 nucleotides or longer. In some cases, the barcode subsequence may be at most 4, 5, 6, 7, 8, 9, 10, 11, 12, 13, 14, 15, 16 nucleotides or shorter.

The co-partitioned oligonucleotides can also comprise other functional sequences useful in the processing of the nucleic acids from the co-partitioned cells. These sequences include, e.g., targeted or random/universal amplification primer sequences for amplifying the genomic DNA from the individual cells within the partitions while attaching the associated barcode sequences, sequencing primers or primer recognition sites, hybridization or probing sequences, e.g., for identification of presence of the sequences or for pulling down barcoded nucleic acids, or any of a number of other potential functional sequences. Again, co-partitioning of oligonucleotides and associated barcodes and other functional sequences, along with sample materials is described in, for example, U.S. Patent Application Nos. 61/940,318, filed Feb. 7, 2014, 61/991,018, filed May 9, 2014, and U.S. patent application Ser. No. 14/316,383, filed Jun. 26, 2014, as well as U.S. patent application Ser. No. 14/175,935, filed Feb. 7, 2014, the full disclosures of which are incorporated herein by reference in their entireties for all purposes. As will be appreciated other mechanisms of co-partitioning of oligonucleotides may also be employed, including, e.g., coalescence of two or more droplets, where one droplet contains oligonucleotides, or microdispensing of oligonucleotides into partitions, e.g., droplets within microfluidic systems.

Briefly, in one example, beads, microparticles or microcapsules are provided that each include large numbers of the above described oligonucleotides releasably attached to the beads, where all of the oligonucleotides attached to a particular bead will include the same nucleic acid barcode sequence, but where a large number of diverse barcode sequences are represented across the population of beads used. In particularly useful examples, hydrogel beads, e.g., comprising polyacrylamide polymer matrices, are used as a solid support and delivery vehicle for the oligonucleotides into the partitions, as they are capable of carrying large numbers of oligonucleotide molecules, and may be configured to release those oligonucleotides upon exposure to a particular stimulus, as described elsewhere herein. In some cases, the population of beads will provide a diverse barcode sequence library that includes at least 1,000 different barcode sequences, at least 5,000 different barcode sequences, at least 10,000 different barcode sequences, at least at least 50,000 different barcode sequences, at least 100,000 different barcode sequences, at least 1,000,000 different barcode sequences, at least 5,000,000 different barcode sequences, or at least 10,000,000 different barcode sequences. Additionally, each bead can be provided with large numbers of oligonucleotide molecules attached. In particular, the number of molecules of oligonucleotides including the barcode sequence on an individual bead can be at least 1,000 oligonucleotide molecules, at least 5,000 oligonucleotide molecules, at least 10,000 oligonucleotide molecules, at least 50,000 oligonucleotide molecules, at least 100,000 oligonucleotide molecules, at least 500,000 oligonucleotides, at least 1,000,000 oligonucleotide molecules, at least 5,000,000 oligonucleotide molecules, at least 10,000,000 oligonucleotide molecules, at least 50,000,000 oligonucleotide molecules, at least 100,000,000 oligonucleotide molecules, and in some cases at least 1 billion oligonucleotide molecules.

Moreover, when the population of beads is partitioned, the resulting population of partitions can also include a diverse barcode library that includes at least 1,000 different barcode sequences, at least 5,000 different barcode sequences, at least 10,000 different barcode sequences, at least at least 50,000 different barcode sequences, at least 100,000 different barcode sequences, at least 1,000,000 different barcode sequences, at least 5,000,000 different barcode sequences, or at least 10,000,000 different barcode sequences. Additionally, each partition of the population can include at least 1,000 oligonucleotide molecules, at least 5,000 oligonucleotide molecules, at least 10,000 oligonucleotide molecules, at least 50,000 oligonucleotide molecules, at least 100,000 oligonucleotide molecules, at least 500,000 oligonucleotides, at least 1,000,000 oligonucleotide molecules, at least 5,000,000 oligonucleotide molecules, at least 10,000,000 oligonucleotide molecules, at least 50,000,000 oligonucleotide molecules, at least 100,000,000 oligonucleotide molecules, and in some cases at least 1 billion oligonucleotide molecules.

In some cases, it may be desirable to incorporate multiple different barcodes within a given partition, either attached to a single or multiple beads within the partition. For example, in some cases, a mixed, but known barcode sequences set may provide greater assurance of identification in the subsequent processing, e.g., by providing a stronger address or attribution of the barcodes to a given partition, as a duplicate or independent confirmation of the output from a given partition.

The oligonucleotides are releasable from the beads upon the application of a particular stimulus to the beads. In some cases, the stimulus may be a photo-stimulus, e.g., through cleavage of a photo-labile linkage that releases the oligonucleotides. In other cases, a thermal stimulus may be used, where elevation of the temperature of the beads environment will result in cleavage of a linkage or other release of the oligonucleotides form the beads. In still other cases, a chemical stimulus is used that cleaves a linkage of the oligonucleotides to the beads, or otherwise results in release of the oligonucleotides from the beads. Examples of this type of system are described in U.S. patent application Ser. No. 13/966,150, filed Aug. 13, 2013, as well as U.S. Provisional Patent Application Nos. 61/940,318, filed Feb. 7, 2014, 61/991,018, Filed May 9, 2014, and U.S. patent application Ser. No. 14/316,383, filed Jun. 26, 2014, the full disclosures of which are hereby incorporated herein by reference n their entireties for all purposes. In one case, such compositions include the polyacrylamide matrices described above for encapsulation of cells, and may be degraded for release of the attached oligonucleotides through exposure to a reducing agent, such as DTT.

Figure 2:
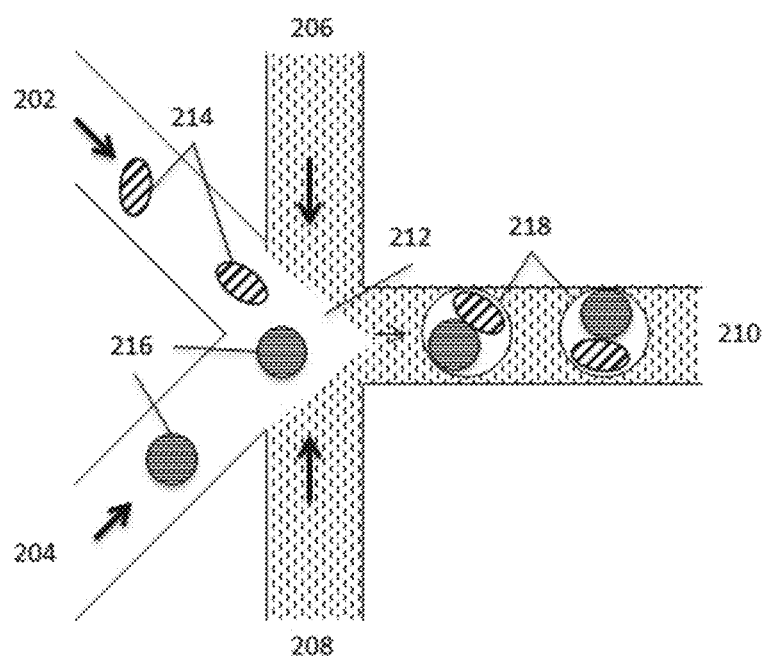
FIG. 2 schematically illustrates a microfluidic channel structure for co-partitioning cells and beads or microcapsules comprising additional reagents.

In accordance with the methods and systems described herein, the beads including the attached oligonucleotides are co-partitioned with the individual cells, such that a single bead and a single cell are contained within an individual partition. As noted above, while single cell/single bead occupancy is the most desired state, it will be appreciated that multiply occupied partitions (either in terms of cells, beads or both), or unoccupied partitions (either in terms of cells, beads or both) will often be present. An example of a microfluidic channel structure for co-partitioning cells and beads comprising barcode oligonucleotides is schematically illustrated in FIG. 2. As described elsewhere herein, in some aspects, a substantial percentage of the overall occupied partitions will include both a bead and a cell and, in some cases, some of the partitions that are generated will be unoccupied. In some cases, some of the partitions may have beads and cells that are not partitioned 1:1. In some cases, it may be desirable to provide multiply occupied partitions, e.g., containing two, three, four or more cells and/or beads within a single partition. As shown, channel segments 202, 204, 206, 208 and 210 are provided in fluid communication at channel junction 212. An aqueous stream comprising the individual cells 214, is flowed through channel segment 202 toward channel junction 212. As described above, these cells may be suspended within an aqueous fluid, or may have been pre-encapsulated, prior to the partitioning process.

Concurrently, an aqueous stream comprising the barcode carrying beads 216, is flowed through channel segment 204 toward channel junction 212. A non-aqueous partitioning fluid 216 is introduced into channel junction 212 from each of side channels 206 and 208, and the combined streams are flowed into outlet channel 210. Within channel junction 212, the two combined aqueous streams from channel segments 202 and 204 are combined, and partitioned into droplets 218, that include co-partitioned cells 214 and beads 216. As noted previously, by controlling the flow characteristics of each of the fluids combining at channel junction 212, as well as controlling the geometry of the channel junction, one can optimize the combination and partitioning to achieve a desired occupancy level of beads, cells or both, within the partitions 218 that are generated.

In some cases, lysis agents, e.g., cell lysis enzymes, may be introduced into the partition with the bead stream, e.g., flowing through channel segment 204, such that lysis of the cell only commences at or after the time of partitioning. Additional reagents may also be added to the partition in this configuration, such as endonucleases to fragment the cell's DNA, DNA polymerase enzyme and dNTPs used to amplify the cell's nucleic acid fragments and to attach the barcode oligonucleotides to the amplified fragments. As noted above, in many cases, a chemical stimulus, such as DTT, may be used to release the barcodes from their respective beads into the partition. In such cases, it may be particularly desirable to provide the chemical stimulus along with the cell-containing stream in channel segment 202, such that release of the barcodes only occurs after the two streams have been combined, e.g., within the partitions 218. Where the cells are encapsulated, however, introduction of a common chemical stimulus, e.g., that both releases the oligonucleotides form their beads, and releases cells from their microcapsules may generally be provided from a separate additional side channel (not shown) upstream of or connected to channel junction 212.

As will be appreciated, a number of other reagents may be co-partitioned along with the cells, beads, lysis agents and chemical stimuli, including, for example, protective reagents, like proteinase K, chelators, nucleic acid extension, replication, transcription or amplification reagents such as polymerases, reverse transcriptases, transposases which can be used for transposon based methods (e.g., Nextera), nucleoside triphosphates or NTP analogues, primer sequences and additional cofactors such as divalent metal ions used in such reactions, ligation reaction reagents, such as ligase enzymes and ligation sequences, dyes, labels, or other tagging reagents.

The channel networks, e.g., as described herein, can be fluidly coupled to appropriate fluidic components. For example, the inlet channel segments, e.g., channel segments 202, 204, 206 and 208 are fluidly coupled to appropriate sources of the materials they are to deliver to channel junction 212. For example, channel segment 202 will be fluidly coupled to a source of an aqueous suspension of cells 214 to be analyzed, while channel segment 204 would be fluidly coupled to a source of an aqueous suspension of beads 216. Channel segments 206 and 208 would then be fluidly connected to one or more sources of the non-aqueous fluid. These sources may include any of a variety of different fluidic components, from simple reservoirs defined in or connected to a body structure of a microfluidic device, to fluid conduits that deliver fluids from off-device sources, manifolds, or the like. Likewise, the outlet channel segment 210 may be fluidly coupled to a receiving vessel or conduit for the partitioned cells. Again, this may be a reservoir defined in the body of a microfluidic device, or it may be a fluidic conduit for delivering the partitioned cells to a subsequent process operation, instrument or component.

Figure 8:
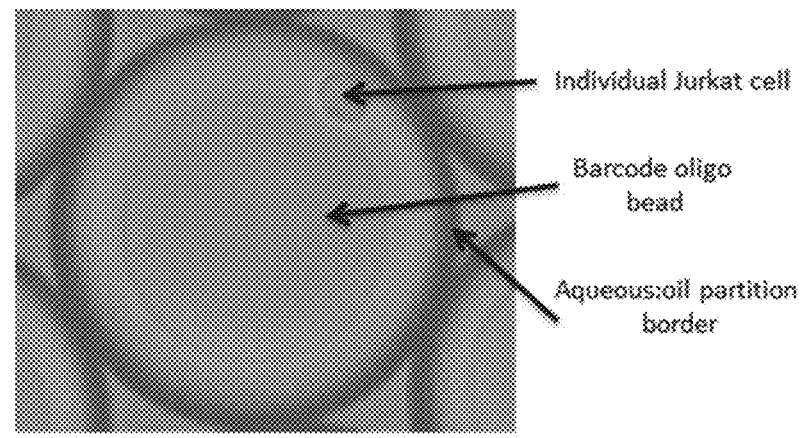
FIG. 8 provides an image of individual cells co-partitioned along with individual barcode bearing beads FIG. 9A-E provides schematic illustration of example barcoded oligonucleotide structures for use in analysis of RNA and example operations for performing RNA analysis.
Figure 8:
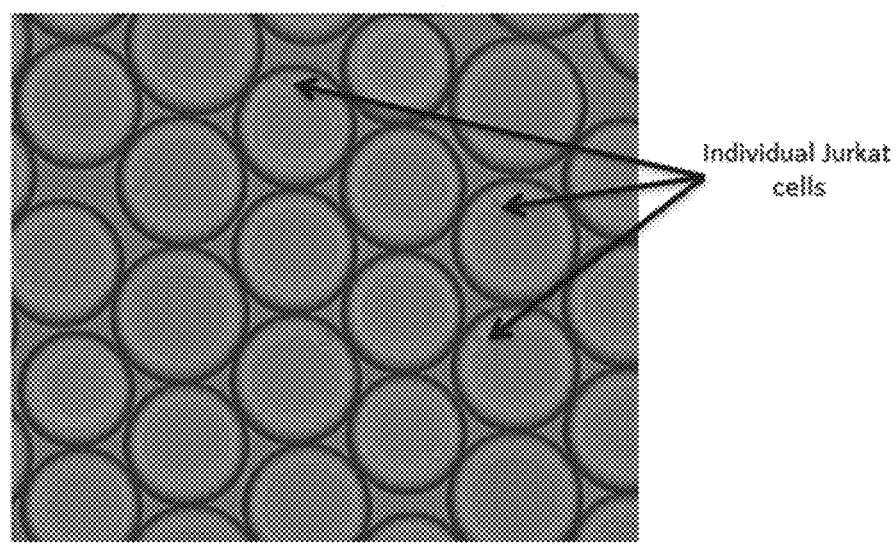

FIG. 8 shows images of individual Jurkat cells co-partitioned along with barcode oligonucleotide containing beads in aqueous droplets in an aqueous in oil emulsion. As illustrated, individual cells may be readily co-partitioned with individual beads. As will be appreciated, optimization of individual cell loading may be carried out by a number of methods, including by providing dilutions of cell populations into the microfluidic system in order to achieve the desired cell loading per partition as described elsewhere herein.

In operation, once lysed, the nucleic acid contents of the individual cells are then available for further processing within the partitions, including, e.g., fragmentation, amplification and barcoding, as well as attachment of other functional sequences. As noted above, fragmentation may be accomplished through the co-partitioning of shearing enzymes, such as endonucleases, in order to fragment the nucleic acids into smaller fragments. These endonucleases may include restriction endonucleases, including type II and type IIs restriction endonucleases as well as other nucleic acid cleaving enzymes, such as nicking endonucleases, and the like. In some cases, fragmentation may not be desired, and full length nucleic acids may be retained within the partitions, or in the case of encapsulated cells or cell contents, fragmentation may be carried out prior to partitioning, e.g., through enzymatic methods, e.g., those described herein, or through mechanical methods, e.g., mechanical, acoustic or other shearing.

Once co-partitioned, and the cells are lysed to release their nucleic acids, the oligonucleotides disposed upon the bead may be used to barcode and amplify fragments of those nucleic acids. A particularly elegant process for use of these barcode oligonucleotides in amplifying and barcoding fragments of sample nucleic acids is described in detail in U.S.

Provisional Patent Application Nos. 61/940,318, filed Feb. 7, 2014, 61/991,018, Filed May 9, 2014, and U.S. patent application Ser. No. 14/316,383, filed Jun. 26, 2014, and previously incorporated by reference. Briefly, in one aspect, the oligonucleotides present on the beads that are co-partitioned with the cells, are released from their beads into the partition with the cell's nucleic acids. The oligonucleotides can include, along with the barcode sequence, a primer sequence at its 5' end. This primer sequence may be a random oligonucleotide sequence intended to randomly prime numerous different regions on the cell's nucleic acids, or it may be a specific primer sequence targeted to prime upstream of a specific targeted region of the cell's genome.

Figure 3:
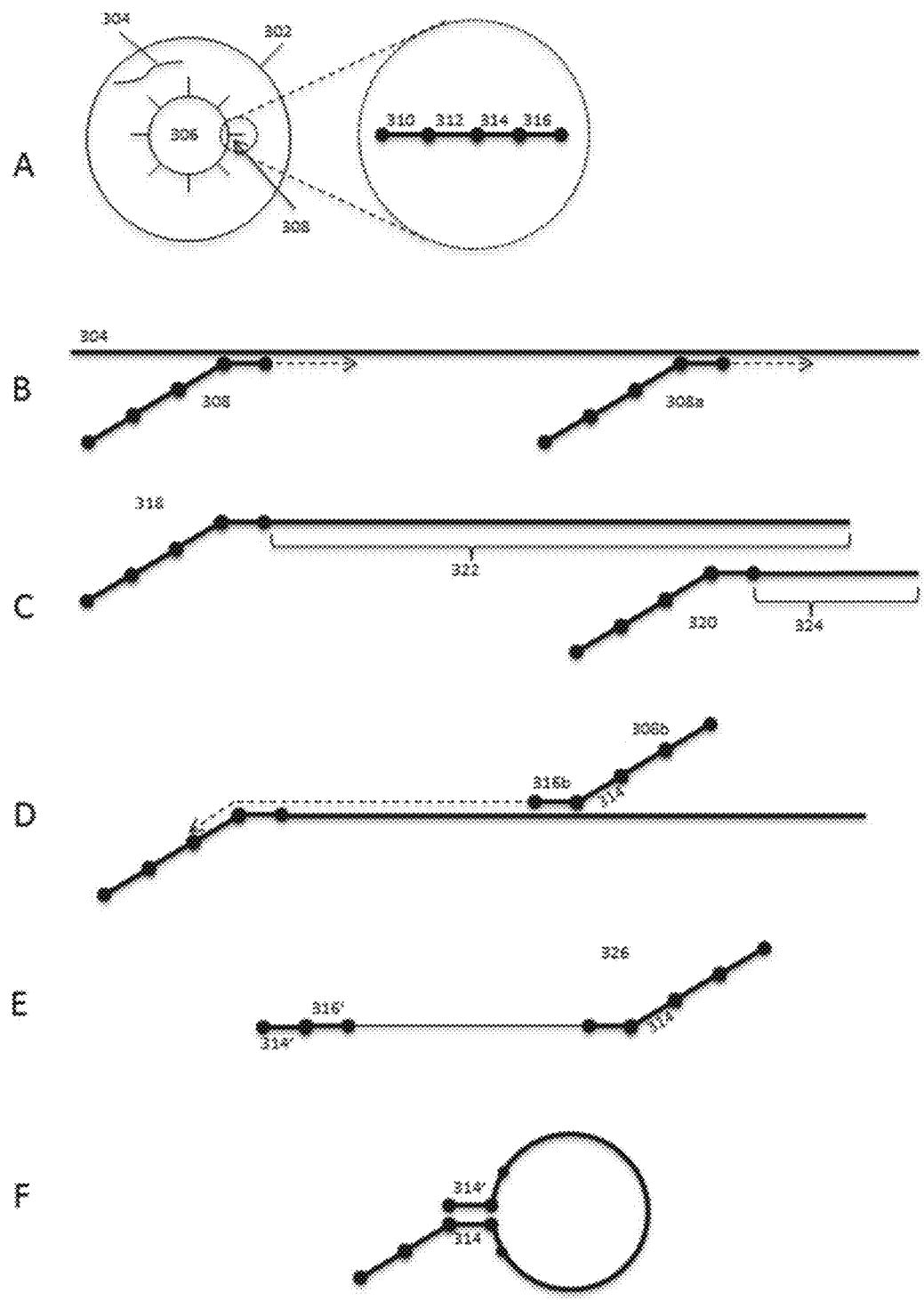
FIG. 3 schematically illustrates an example process for amplification and barcoding of cell's nucleic acids.

Once released, the primer portion of the oligonucleotide can anneal to a complementary region of the cell's nucleic acid. Extension reaction reagents, e.g., DNA polymerase, nucleoside triphosphates, co-factors (e.g., $Mg^{2+}$ or $Mn^{2+}$), that are also co-partitioned with the cells and beads, then extend the primer sequence using the cell's nucleic acid as a template, to produce a complementary fragment to the strand of the cell's nucleic acid to which the primer annealed, which complementary fragment includes the oligonucleotide and its associated barcode sequence. Annealing and extension of multiple primers to different portions of the cell's nucleic acids will result in a large pool of overlapping complementary fragments of the nucleic acid, each possessing its own barcode sequence indicative of the partition in which it was created. In some cases, these complementary fragments may themselves be used as a template primed by the oligonucleotides present in the partition to produce a complement of the complement that again, includes the barcode sequence. In some cases, this replication process is configured such that when the first complement is duplicated, it produces two complementary sequences at or near its termini, to allow formation of a hairpin structure or partial hairpin structure, the reduces the ability of the molecule to be the basis for producing further iterative copies. As described herein, the cell's nucleic acids may include any desired nucleic acids within the cell including, for example, the cell's DNA, e.g., genomic DNA, RNA, e.g., messenger RNA, and the like. For example, in some cases, the methods and systems described herein are used in characterizing expressed mRNA, including, e.g., the presence and quantification of such mRNA, and may include RNA sequencing processes as the characterization process. Alternatively or additionally, the reagents partitioned along with the cells may include reagents for the conversion of mRNA into cDNA, e.g., reverse transcriptase enzymes and reagents, to facilitate sequencing processes where DNA sequencing is employed. In some cases, where the nucleic acids to be characterized comprise RNA, e.g., mRNA, schematic illustration of one example of this is shown in FIG. 3.

As shown, oligonucleotides that include a barcode sequence are co-partitioned in, e.g., a droplet 302 in an emulsion, along with a sample nucleic acid 304. As noted elsewhere herein, the oligonucleotides 308 may be provided on a bead 306 that is co-partitioned with the sample nucleic acid 304, which oligonucleotides are releasable from the bead 306, as shown in panel A. The oligonucleotides 308 include a barcode sequence 312, in addition to one or more functional sequences, e.g., sequences 310, 314 and 316. For example, oligonucleotide 308 is shown as comprising barcode sequence 312, as well as sequence 310 that may function as an attachment or immobilization sequence for a given sequencing system, e.g., a P5 sequence used for attachment in flow cells of an Illumina Hiseq® or Miseq® system. As shown, the oligonucleotides also include a primer sequence 316, which may include a random or targeted N-mer for priming replication of portions of the sample nucleic acid 304. Also included within oligonucleotide 308 is a sequence 314 which may provide a sequencing priming region, such as a "read1" or R1 priming region, that is used to prime polymerase mediated, template directed sequencing by synthesis reactions in sequencing systems. As will be appreciated, the functional sequences may be selected to be compatible with a variety of different sequencing systems, e.g., 454 Sequencing, Ion Torrent Proton or PGM, Illumina X10, etc., and the requirements thereof. In many cases, the barcode sequence 312, immobilization sequence 310 and R1 sequence 314 may be common to all of the oligonucleotides attached to a given bead. The primer sequence 316 may vary for random N-mer primers, or may be common to the oligonucleotides on a given bead for certain targeted applications.

As will be appreciated, in some cases, the functional sequences may include primer sequences useful for RNA-seq applications. For example, in some cases, the oligonucleotides may include poly-T primers for priming reverse transcription of RNA for RNA-seq. In still other cases, oligonucleotides in a given partition, e.g., included on an individual bead, may include multiple types of primer sequences in addition to the common barcode sequences, such as both DNA-sequencing and RNA sequencing primers, e.g., poly-T primer sequences included within the oligonucleotides coupled to the bead. In such cases, a single partitioned cell may be both subjected to DNA and RNA sequencing processes.

Based upon the presence of primer sequence 316, the oligonucleotides can prime the sample nucleic acid as shown in panel B, which allows for extension of the oligonucleotides 308 and 308a using polymerase enzymes and other extension reagents also co-partitioned with the bead 306 and sample nucleic acid 304. As shown in panel C, following extension of the oligonucleotides that, for random N-mer primers, would anneal to multiple different regions of the sample nucleic acid 304; multiple overlapping complements or fragments of the nucleic acid are created, e.g., fragments 318 and 320. Although including sequence portions that are complementary to portions of sample nucleic acid, e.g., sequences 322 and 324, these constructs are generally referred to herein as comprising fragments of the sample nucleic acid 304, having the attached barcode sequences.

The barcoded nucleic acid fragments may then be subjected to characterization, e.g., through sequence analysis, or they may be further amplified in the process, as shown in panel D. For example, additional oligonucleotides, e.g., oligonucleotide 308b, also released from bead 306, may prime the fragments 318 and 320. This shown in for fragment 318. In particular, again, based upon the presence of the random N-mer primer 316b in oligonucleotide 308b (which in many cases can be different from other random N-mers in a given partition, e.g., primer sequence 316), the oligonucleotide anneals with the fragment 318, and is extended to create a complement 326 to at least a portion of fragment 318 which includes sequence 328, that comprises a duplicate of a portion of the sample nucleic acid sequence. Extension of the oligonucleotide 308b continues until it has replicated through the oligonucleotide portion 308 of fragment 318. As noted elsewhere herein, and as illustrated in panel D, the oligonucleotides may be configured to prompt a stop in the replication by the polymerase at a desired point, e.g., after replicating through sequences 316 and 314 of oligonucleotide 308 that is included within fragment 318. As described herein, this may be accomplished by different methods, including, for example, the incorporation of different nucleotides and/or nucleotide analogues that are not capable of being processed by the polymerase enzyme used. For example, this may include the inclusion of uracil containing nucleotides within the sequence region 312 to prevent a non-uracil tolerant polymerase to cease replication of that region. As a result a fragment 326 is created that includes the full-length oligonucleotide 308b at one end, including the barcode sequence 312, the attachment sequence 310, the R1 primer region 314, and the random N-mer sequence 316b. At the other end of the sequence may be included the complement 316' to the random N-mer of the first oligonucleotide 308, as well as a complement to all or a portion of the R1 sequence, shown as sequence 314'. The R1 sequence 314 and its complement 314' are then able to hybridize together to form a partial hairpin structure 328. As will be appreciated because the random N-mers differ among different oligonucleotides, these sequences and their complements would not be expected to participate in hairpin formation, e.g., sequence 316', which is the complement to random N-mer 316, would not be expected to be complementary to random N-mer sequence 316b. This would not be the case for other applications, e.g., targeted primers, where the N-mers would be common among oligonucleotides within a given partition.

By forming these partial hairpin structures, it allows for the removal of first level duplicates of the sample sequence from further replication, e.g., preventing iterative copying of copies. The partial hairpin structure also provides a useful structure for subsequent processing of the created fragments, e.g., fragment 326.

In general, the amplification of the cell's nucleic acids is carried out until the barcoded overlapping fragments within the partition constitute at least 1× coverage of the particular portion or all of the cell's genome, at least 2×, at least 3×, at least 4×, at least 5×, at least 10×, at least 20×, at least 40× or more coverage of the genome or its relevant portion of interest. Once the barcoded fragments are produced, they may be directly sequenced on an appropriate sequencing system, e.g., an Illumina Hiseq®, Miseq® or X10 system, or they may be subjected to additional processing, such as further amplification, attachment of other functional sequences, e.g., second sequencing primers, for reverse reads, sample index sequences, and the like.

Figure 4:
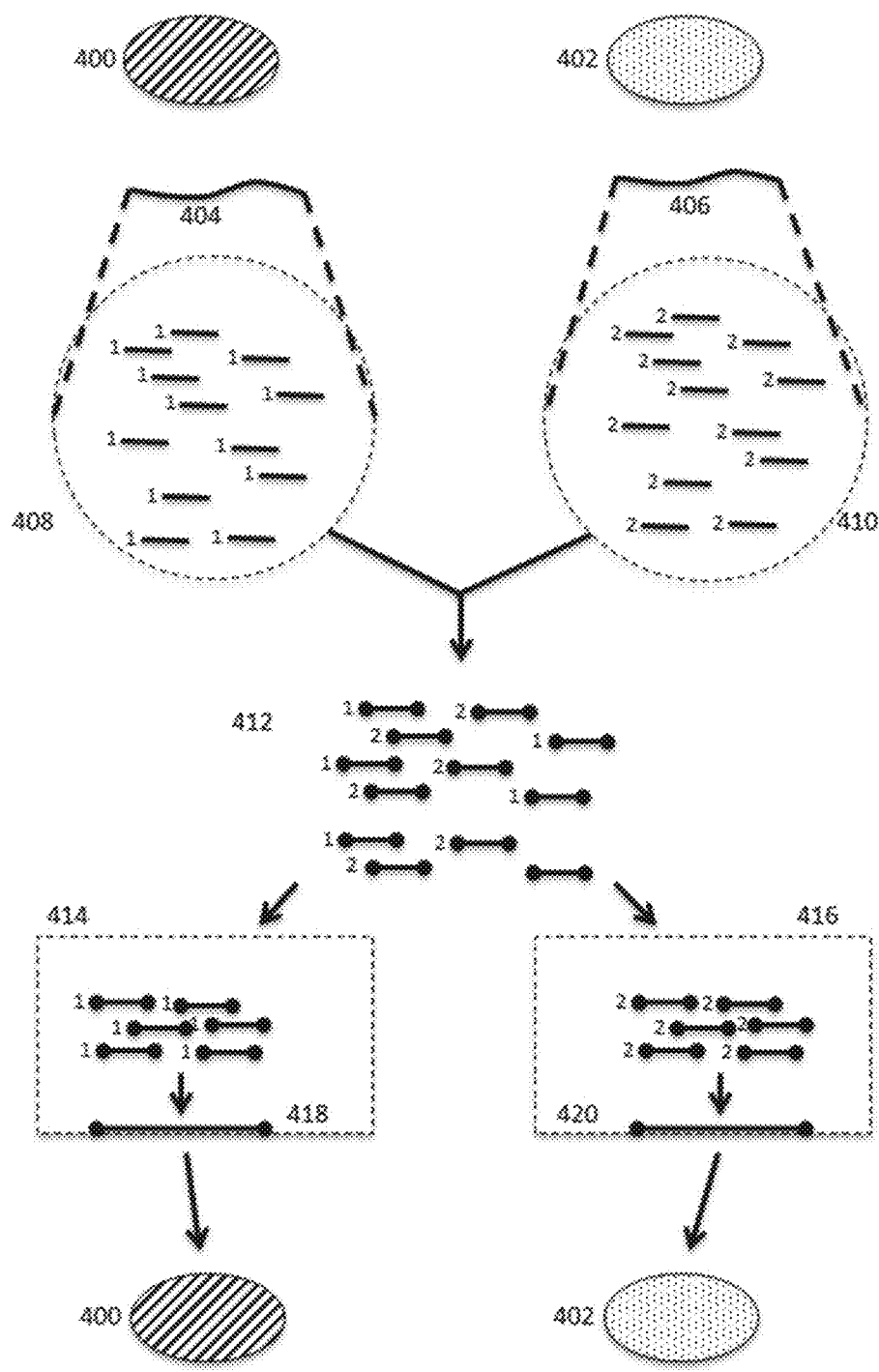
FIG. 4 provides a schematic illustration of use of barcoding of cell's nucleic acids in attributing sequence data to individual cells or groups of cells for use in their characterization.

All of the fragments from multiple different partitions may then be pooled for sequencing on high throughput sequencers as described herein, where the pooled fragments comprise a large number of fragments derived from the nucleic acids of different cells or small cell populations, but where the fragments from the nucleic acids of a given cell will share the same barcode sequence. In particular, because each fragment is coded as to its partition of origin, and consequently its single cell or small population of cells, the sequence of that fragment may be attributed back to that cell or those cells based upon the presence of the barcode, which will also aid in applying the various sequence fragments from multiple partitions to assembly of individual genomes for different cells. This is schematically illustrated in FIG. 4. As shown in one example, a first nucleic acid 404 from a first cell 400, and a second nucleic acid 406 from a second cell 402 are each partitioned along with their own sets of barcode oligonucleotides as described above. The nucleic acids may comprise a chromosome, entire genome or other large nucleic acid from the cells.

Within each partition, each cell's nucleic acids 404 and 406 is then processed to separately provide overlapping set of second fragments of the first fragment(s), e.g., second fragment sets 408 and 410. This processing also provides the second fragments with a barcode sequence that is the same for each of the second fragments derived from a particular first fragment. As shown, the barcode sequence for second fragment set 408 is denoted by "1" while the barcode sequence for fragment set 410 is denoted by "2". A diverse library of barcodes may be used to differentially barcode large numbers of different fragment sets. However, it is not necessary for every second fragment set from a different first fragment to be barcoded with different barcode sequences. In fact, in many cases, multiple different first fragments may be processed concurrently to include the same barcode sequence. Diverse barcode libraries are described in detail elsewhere herein.

The barcoded fragments, e.g., from fragment sets 408 and 410, may then be pooled for sequencing using, for example, sequence by synthesis technologies available from Illumina or Ion Torrent division of Thermo-Fisher, Inc. Once sequenced, the sequence reads 412 can be attributed to their respective fragment set, e.g., as shown in aggregated reads 414 and 416, at least in part based upon the included barcodes, and in some cases, in part based upon the sequence of the fragment itself. The attributed sequence reads for each fragment set are then assembled to provide the assembled sequence for each cell's nucleic acids, e.g., sequences 418 and 420, which in turn, may be attributed to individual cells, e.g., cells 400 and 402.

While described in terms of analyzing the genetic material present within cells, the methods and systems described herein may have much broader applicability, including the ability to characterize other aspects of individual cells or cell populations, by allowing for the allocation of reagents to individual cells, and providing for the attributable analysis or characterization of those cells in response to those reagents. These methods and systems are particularly valuable in being able to characterize cells for, e.g., research, diagnostic, pathogen identification, and many other purposes. By way of example, a wide range of different cell surface features, e.g., cell surface proteins like cluster of differentiation or CD proteins, have significant diagnostic relevance in characterization of diseases like cancer.

In one particularly useful application, the methods and systems described herein may be used to characterize cell features, such as cell surface features, e.g., proteins, receptors, etc. In particular, the methods described herein may be used to attach reporter molecules to these cell features, that when partitioned as described above, may be barcoded and analyzed, e.g., using DNA sequencing technologies, to ascertain the presence, and in some cases, relative abundance or quantity of such cell features within an individual cell or population of cells.

In a particular example, a library of potential cell binding ligands, e.g., antibodies, antibody fragments, cell surface receptor binding molecules, or the like, maybe provided associated with a first set of nucleic acid reporter molecules, e.g., where a different reporter oligonucleotide sequence is associated with a specific ligand, and therefore capable of binding to a specific cell surface feature. In some aspects, different members of the library may be characterized by the presence of a different oligonucleotide sequence label, e.g., an antibody to a first type of cell surface protein or receptor would have associated with it a first known reporter oligonucleotide sequence, while an antibody to a second receptor protein would have a different known reporter oligonucleotide sequence associated with it. Prior to co-partitioning, the cells would be incubated with the library of ligands, that may represent antibodies to a broad panel of different cell surface features, e.g., receptors, proteins, etc., and which include their associated reporter oligonucleotides. Unbound ligands are washed from the cells, and the cells are then co-partitioned along with the barcode oligonucleotides described above. As a result, the partitions will include the cell or cells, as well as the bound ligands and their known, associated reporter oligonucleotides.

Without the need for lysing the cells within the partitions, one could then subject the reporter oligonucleotides to the barcoding operations described above for cellular nucleic acids, to produce barcoded, reporter oligonucleotides, where the presence of the reporter oligonucleotides can be indicative of the presence of the particular cell surface feature, and the barcode sequence will allow the attribution of the range of different cell surface features to a given individual cell or population of cells based upon the barcode sequence that was co-partitioned with that cell or population of cells. As a result, one may generate a cell-by-cell profile of the cell surface features within a broader population of cells. This aspect of the methods and systems described herein, is described in greater detail below.

Figure 5:
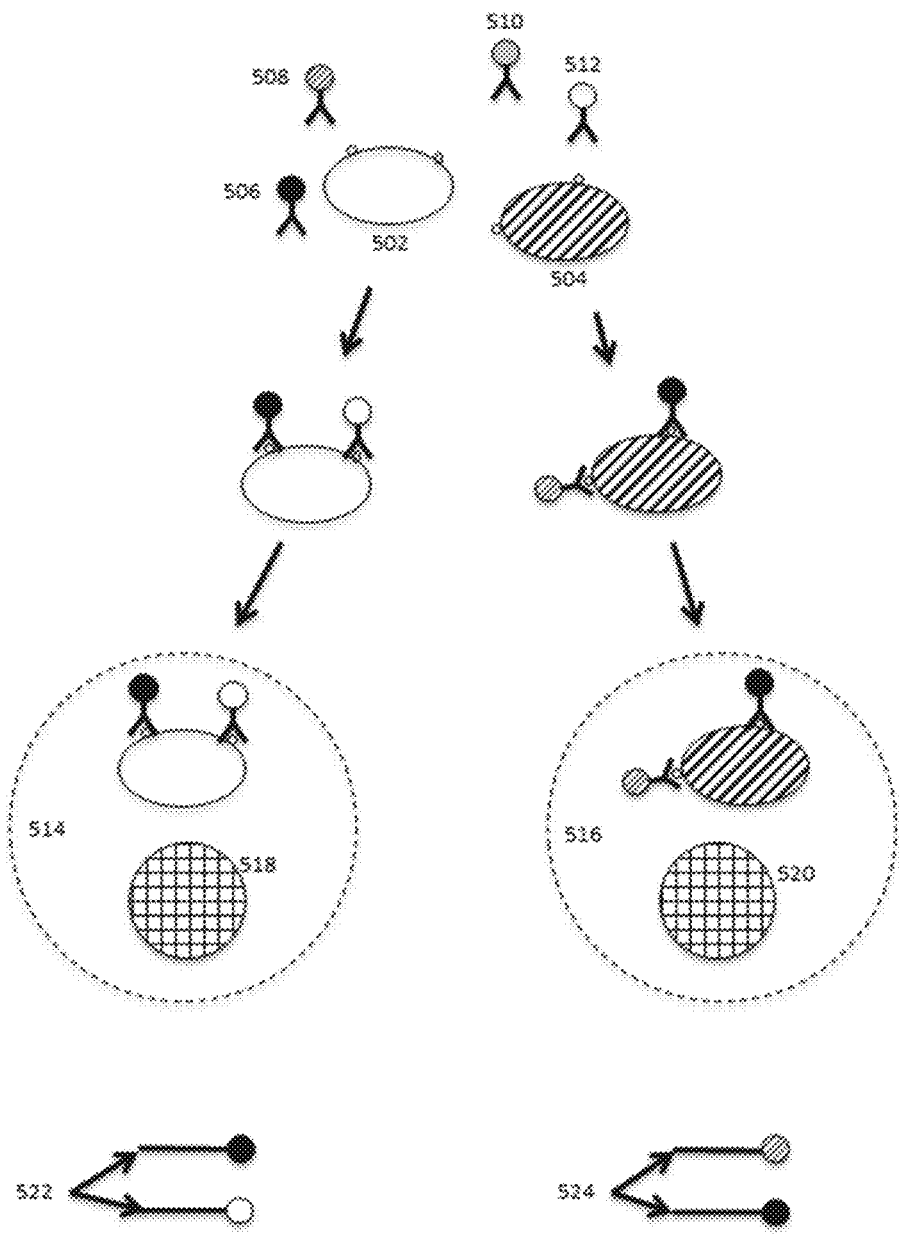
FIG. 5 provides a schematic illustrating cells associated with labeled cell-binding ligands.

This example is schematically illustrated in FIG. 5. As shown, a population of cells, represented by cells 502 and 504 are incubated with a library of cell surface associated reagents, e.g., antibodies, cell surface binding proteins, ligands or the like, where each different type of binding group includes an associated nucleic acid reporter molecule associated with it, shown as ligands and associated reporter molecules 506, 508, 510 and 512 (with the reporter molecules being indicated by the differently shaded circles). Where the cell expresses the surface features that are bound by the library, the ligands and their associated reporter molecules can become associated or coupled with the cell surface. Individual cells are then partitioned into separate partitions, e.g., droplets 514 and 516, along with their associated ligand/reporter molecules, as well as an individual barcode oligonucleotide bead as described elsewhere herein, e.g., beads 522 and 524, respectively. As with other examples described herein, the barcoded oligonucleotides are released from the beads and used to attach the barcode sequence the reporter molecules present within each partition with a barcode that is common to a given partition, but which varies widely among different partitions. For example, as shown in FIG. 5, the reporter molecules that associate with cell 502 in partition 514 are barcoded with barcode sequence 518, while the reporter molecules associated with cell 504 in partition 516 are barcoded with barcode 520. As a result, one is provided with a library of oligonucleotides that reflects the surface ligands of the cell, as reflected by the reporter molecule, but which is substantially attributable to an individual cell by virtue of a common barcode sequence, allowing a single cell level profiling of the surface characteristics of the cell. As will be appreciated, this process is not limited to cell surface receptors but may be used to identify the presence of a wide variety of specific cell structures, chemistries or other characteristics.

III. BARCODING

Downstream applications, for example DNA sequencing, may rely on the barcodes to identify the origin of a sequence and, for example, to assemble a larger sequence from sequenced fragments. Therefore, it may be desirable to add barcodes to the polynucleotide fragments generated by the methods described herein. Barcodes may be of a variety of different formats, including polynucleotide barcodes. Depending upon the specific application, barcodes may be attached to polynucleotide fragments in a reversible or irreversible manner. Barcodes may also allow for identification and/or quantification of individual polynucleotide fragments during sequencing.

Barcodes may be loaded into partitions so that one or more barcodes are introduced into a particular partition. Each partition may contain a different set of barcodes. This may be accomplished by directly dispensing the barcodes into the partitions, enveloping the barcodes (e.g., in a droplet of an emulsion), or by placing the barcodes within a container that is placed in a partition (e.g., a microcapsule).

For example, a population of microcapsules may be prepared such that a first microcapsule in the population comprises multiple copies of identical barcodes (e.g., polynucleotide bar codes, etc.) and a second microcapsule in the population comprises multiple copies of a barcode that differs from the barcode within the first microcapsule. In some cases, the population of microcapsules may comprise multiple microcapsules (e.g., greater than about 2, 3, 4, 5, 6, 7, 8, 9, 10, 15, 20, 25, 30, 35, 40, 45, 50, 100, 500, 1000, 5000, 10000, 100000, 1000000, 10000000, 100000000, or 1000000000 microcapsules), each containing multiple copies of a barcode that differs from that contained in the other microcapsules. In some cases, the population may comprise greater than about 2, 3, 4, 5, 6, 7, 8, 9, 10, 15, 20, 25, 30, 35, 40, 45, 50, 100, 500, 1000, 5000, 10000, 100000, 1000000, 10000000, 100000000, or 1000000000 microcapsules with identical sets of barcodes. In some cases, the population may comprise greater than about 2, 3, 4, 5, 6, 7, 8, 9, 10, 15, 20, 25, 30, 35, 40, 45, 50, 100, 500, 1000, 5000, 10000, 100000, 1000000, 10000000, 100000000, or 1000000000 microcapsules, wherein the microcapsules each comprise a different combination of barcodes. For example, in some cases the different combinations overlap, such that a first microcapsule may comprise, e.g., barcodes A, B, and C, while a second microcapsule may comprise barcodes A, B, and D. In another example, the different combinations do not overlap, such that a first microcapsule may comprise, e.g., barcodes A, B, and C, while a second microcapsule may comprise barcodes D, E, and F. The use of microcapsules is, of course, optional. All of the combinations described above, and throughout this disclosure, may also be generated by dispending barcodes (and other reagents) directly into partitions (e.g., microwells).

The barcodes may be loaded into the partitions at an expected or predicted ratio of barcodes per species to be barcoded (e.g., polynucleotide fragment, strand of polynucleotide, cell, etc.). In some cases, the barcodes are loaded into partitions such that more than about 1, 2, 3, 4, 5, 6, 7, 8, 9, 10, 20, 50, 100, 500, 1000, 5000, 10000, or 200000 barcodes are loaded per species. In some cases, the barcodes are loaded in the partitions so that less than about 1, 2, 3, 4, 5, 6, 7, 8, 9, 10, 20, 50, 100, 500, 1000, 5000, 10000, or 200000 barcodes are loaded per species. In some cases, the average number of barcodes loaded per species is less than, or greater than, about 0.0001, 0.001, 0.01, 0.1, 1, 2, 3, 4, 5, 6, 7, 8, 9, 10, 20, 50, 100, 500, 1000, 5000, 10000, or 200000 barcodes per species.

When more than one barcode is present per polynucleotide fragment, such barcodes may be copies of the same barcode, or multiple different barcodes. For example, the attachment process may be designed to attach multiple identical barcodes to a single polynucleotide fragment, or multiple different barcodes to the polynucleotide fragment.

A microcapsule may be any of a number of sizes or shapes. In some cases, the shape of the microcapsule may be spherical, ellipsoidal, cylindrical, hexagonal or any other symmetrical or non-symmetrical shape. Any cross-section of the microcapsule may also be of any appropriate shape, include but not limited to: circular, oblong, square, rectangular, hexagonal, or other symmetrical or non-symmetrical shape. In some cases, the microcapsule may be of a specific shape that complements an opening (e.g., surface of a microwell) of the device. For example, the microcapsule may be spherical and the opening of a microwell of the device may be circular.

The microcapsules may be of uniform size (e.g., all of the microcapsules are the same size) or heterogeneous size (e.g., some of the microcapsules are of different sizes). A dimension (e.g., diameter, cross-section, side, etc.) of a microcapsule may be at least about 0.001 µm, 0.01 µm, 0.1 µm, 0.5 µm, 1 µm, 5 µm, 10 µm, 50 µm, 100 µm, 200 µm, 300 µm, 400 µm, 500 µm, 600 µm, 700 µm, 800 µm, 900 µm or 1 nm. In some cases, the microcapsule comprises a microwell that is at most about 0.001 µm, 0.01 µm, 0.1 µm, 0.5 µm, 1 µm, 5 µm, 10 µm, 50 µm, 100 µm, 200 µm, 300 µm, 400 µm, 500 µm, 600 µm, 700 µm, 800 µm, 900 µm or 1 nm.

In some cases, microcapsules are of a size and/or shape so as to allow a limited number of microcapsules to be deposited in individual partitions (e.g., microwells, droplets) of the microcapsule array. Microcapsules may have a specific size and/or shape such that exactly or no more than 1, 2, 3, 4, 5, 6, 7, 8, 9, or 10 capsules fit into an individual microwell; in some cases, on average 1, 2, 3, 4, 5, 6, 7, 8, 9, or 10 capsules fit into an individual microwell. In still further cases, at least 1, 2, 3, 4, 5, 6, 7, 8, 9, 10, 100, 500, or 1000 capsules fit into an individual microwell.

The methods provided herein may comprise loading a partition (e.g., a microwell, droplet of an emulsion) with the reagents necessary for the attachment of barcodes to polynucleotide fragments. In the case of ligation reactions, reagents including restriction enzymes, ligase enzymes, buffers, adapters, barcodes and the like may be loaded into a partition. In the case barcoding by amplification, reagents including primers, DNA polymerases, DNTPs, buffers, barcodes and the like may be loaded into a partition. As described throughout this disclosure, these reagents may be loaded directly into the partition, or via a container such as a microcapsule. If the reagents are not disposed within a container, they may be loaded into a partition (e.g., a microwell) which may then be sealed with a wax or oil until the reagents are used.

Barcodes may be ligated to a polynucleotide fragment using sticky or blunt ends. Barcoded polynucleotide fragments may also be generated by amplifying a polynucleotide fragment with primers comprising barcodes.

Barcodes may be assembled combinatorially, from smaller components designed to assemble in a modular format. For example, three modules, 1A, 1B, and 1C may be combinatorially assembled to produce barcode 1ABC. Such combinatorial assembly may significantly reduce the cost of synthesizing a plurality of barcodes. For example, a combinatorial system consisting of 3 A modules, 3 B modules, and 3 C modules may generate 3*3*3=27 possible barcode sequences from only 9 modules.

Barcoding and beads of the present disclosure may be performed and used as described in, for example, WO2014/028537 and WO 2014/124338, each of which is entirely incorporated herein by reference.

IV. APPLICATIONS OF SINGLE CELL ANALYSIS

There are a wide variety of different applications of the single cell processing and analysis methods and systems described herein, including analysis of specific individual ells, analysis of different cell types within populations of differing cell types, analysis and characterization of large populations of cells for environmental, human health, epidemiological forensic, or any of a wide variety of different applications.

A particularly valuable application of the single cell analysis processes described herein is in the sequencing and characterization of cancer cells. In particular, conventional analytical techniques, including the ensemble sequencing processes alluded to above, are not highly adept at picking small variations in genomic make-up of cancer cells, particularly where those exist in a sea of normal tissue cells. Further, even as between tumor cells, wide variations can exist and can be masked by the ensemble approaches to sequencing (See, e.g., Patel, et al., Single-cell RNA-seq highlights intratumoral heterogeneity in primary glioblastoma, Science DOI: 10.1126/science.1254257 (Published online Jun. 12, 2014). Cancer cells may be derived from solid tumors, hematological malignancies, cell lines, or obtained as circulating tumor cells, and subjected to the partitioning processes described above. Upon analysis, one can identify individual cell sequences as deriving from a single cell or small group of cells, and distinguish those over normal tissue cell sequences. Further, as described in U.S. Provisional Patent Application No. 62/017,808, filed Jun. 26, 2014, the full disclosures of which is hereby incorporated herein by reference in its entirety for all purposes, one may also obtain phased sequence information from each cell, allowing clearer characterization of the haplotype variants within a cancer cell. The single cell analysis approach is particularly useful for systems and methods involving low quantities of input nucleic acids, as described in U.S. Provisional Patent Application No. 62/017,580, filed Jun. 26, 2014, the full disclosures of which is hereby incorporated herein by reference in its entirety for all purposes.

As with cancer cell analysis, the analysis and diagnosis of fetal health or abnormality through the analysis of fetal cells is a difficult task using conventional techniques. In particular, in the absence of relatively invasive procedures, such as amniocentesis obtaining fetal cell samples can employ harvesting those cells from the maternal circulation. As will be appreciated, such circulating fetal cells make up an extremely small fraction of the overall cellular population of that circulation. As a result complex analyses are performed in order to characterize what of the obtained data is likely derived from fetal cells as opposed to maternal cells. By employing the single cell characterization methods and systems described herein, however, one can attribute genetic make up to individual cells, and categorize those cells as maternal or fetal based upon their respective genetic make-up. Further, the genetic sequence of fetal cells may be used to identify any of a number of genetic disorders, including, e.g., aneuploidy such as Down syndrome, Edwards syndrome, and Patau syndrome.

The ability to characterize individual cells from larger diverse populations of cells is also of significant value in both environmental testing as well as in forensic analysis, where samples may, by their nature, be made up of diverse populations of cells and other material that "contaminate" the sample, relative to the cells for which the sample is being tested, e.g., environmental indicator organisms, toxic organisms, and the like for, e.g., environmental and food safety testing, victim and/or perpetrator cells in forensic analysis for sexual assault, and other violent crimes, and the like.

Additional useful applications of the above described single cell sequencing and characterization processes are in the field of neuroscience research and diagnosis. In particular, neural cells can include long interspersed nuclear elements (LINEs), or 'jumping' genes that can move around the genome, which cause each neuron to differ from its neighbor cells. Research has shown that the number of LINEs in human brain exceeds that of other tissues, e.g., heart and liver tissue, with between 80 and 300 unique insertions (See, e.g., Coufal, N. G. et al. *Nature* 460, 1127-1131 (2009)). These differences have been postulated as being related to a person's susceptibility to neuro-logical disorders (see, e.g., Muotri, A. R. et al. *Nature* 468, 443-446 (2010)), or provide the brain with a diversity with which to respond to challenges. As such, the methods described herein may be used in the sequencing and characterization of individual neural cells.

The single cell analysis methods described herein are also useful in the analysis of gene expression, as noted above, both in terms of identification of RNA transcripts and their quantitation. In particular, using the single cell level analysis methods described herein, one can isolate and analyze the RNA transcripts present in individual cells, populations of cells, or subsets of populations of cells. In particular, in some cases, the barcode oligonucleotides may be configured to prime, replicate and consequently yield barcoded fragments of RNA from individual cells. For example, in some cases, the barcode oligonucleotides may include mRNA specific priming sequences, e.g., poly-T primer segments that allow priming and replication of mRNA in a reverse transcription reaction or other targeted priming sequences. Alternatively or additionally, random RNA priming may be carried out using random N-mer primer segments of the barcode oligonucleotides.

Figure 6:
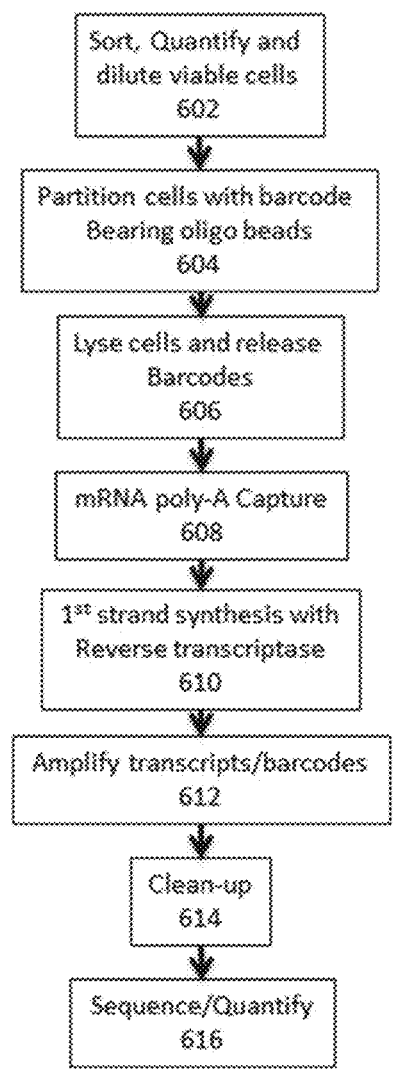
FIG. 6 provides a schematic illustration of an example workflow for performing RNA analysis using the methods described herein.

FIG. 6 provides a schematic of one example method for RNA expression analysis in individual cells using the methods described herein. As shown, at operation 602 a cell containing sample is sorted for viable cells, which are quantified and diluted for subsequent partitioning. At operation 604, the individual cells separately co-partitioned with gel beads bearing the barcoding oligonucleotides as described herein. The cells are lysed and the barcoded oligonucleotides released into the partitions at operation 606, where they interact with and hybridize to the mRNA at operation 608, e.g., by virtue of a poly-T primer sequence, which is complementary to the poly-A tail of the mRNA. Using the poly-T barcode oligonucleotide as a priming sequence, a reverse transcription reaction is carried out at operation 610 to synthesize a cDNA transcript of the mRNA that includes the barcode sequence. The barcoded cDNA transcripts are then subjected to additional amplification at operation 612, e.g., using a PCR process, purification at operation 614, before they are placed on a nucleic acid sequencing system for determination of the cDNA sequence and its associated barcode sequence(s). In some cases, as shown, operations 602 through 608 can occur while the reagents remain in their original droplet or partition, while operations 612 through 616 can occur in bulk (e.g., outside of the partition). In the case where a partition is a droplet in an emulsion, the emulsion can be broken and the contents of the droplet pooled in order to complete operations 612 through 616. In some cases, barcode oligonucleotides may be digested with exonucleases after the emulsion is broken. Exonuclease activity can be inhibited by ethylenediaminetetraacetic acid (EDTA) following primer digestion. In some cases, operation 610 may be performed either within the partitions based upon co-partitioning of the reverse transcription mixture, e.g., reverse transcriptase and associated reagents, or it may be performed in bulk.

As noted elsewhere herein, the structure of the barcode oligonucleotides may include a number of sequence elements in addition to the oligonucleotide barcode sequence. One example of a barcode oligonucleotide for use in RNA analysis as described above is shown in FIG. 7. As shown, the overall oligonucleotide 702 is coupled to a bead 704 by a releasable linkage 706, such as a disulfide linker. The oligonucleotide may include functional sequences that are used in subsequent processing, such as functional sequence 708, which may include one or more of a sequencer specific flow cell attachment sequence, e.g., a P5 sequence for Illumina sequencing systems, as well as sequencing primer sequences, e.g., a R1 primer for Illumina sequencing systems. A barcode sequence 710 is included within the structure for use in barcoding the sample RNA. An mRNA specific priming sequence, such as poly-T sequence 712 is also included in the oligonucleotide structure. An anchoring sequence segment 714 may be included to ensure that the poly-T sequence hybridizes at the sequence end of the mRNA. This anchoring sequence can include a random short sequence of nucleotides, e.g., 1-mer, 2-mer, 3-mer or longer sequence, which will ensure that the poly-T segment is more likely to hybridize at the sequence end of the poly-A tail of the mRNA. An additional sequence segment 716 may be provided within the oligonucleotide sequence. In some cases, this additional sequence provides a unique molecular sequence segment, e.g., as a random sequence (e.g., such as a random N-mer sequence) that varies across individual oligonucleotides coupled to a single bead, whereas barcode sequence 710 can be constant among oligonucleotides tethered to an individual bead. This unique sequence serves to provide a unique identifier of the starting mRNA molecule that was captured, in order to allow quantitation of the number of original expressed RNA. As will be appreciated, although shown as a single oligonucleotide tethered to the surface of a bead, individual bead can include tens to hundreds of thousands or even millions of individual oligonucleotide molecules, where, as noted, the barcode segment can be constant or relatively constant for a given bead, but where the variable or unique sequence segment will vary across an individual bead. This unique molecular sequence segment may include from 5 to about 8 or more nucleotides within the sequence of the oligonucleotides. In some cases, the unique molecular sequence segment can be 2, 3, 4, 5, 6, 7, 8, 9, 10, 11, 12, 13, 14, 15, 16, 17, 18, 19 or 20 nucleotides in length or longer. In some cases, the unique molecular sequence segment can be at least 2, 3, 4, 5, 6, 7, 8, 9, 10, 11, 12, 13, 14, 15, 16, 17, 18, 19 or 20 nucleotides in length or longer. In some cases, the unique molecular sequence segment can be at most 2, 3, 4, 5, 6, 7, 8, 9, 10, 11, 12, 13, 14, 15, 16, 17, 18, 19 or 20 nucleotides in length or shorter.

Figure 7:
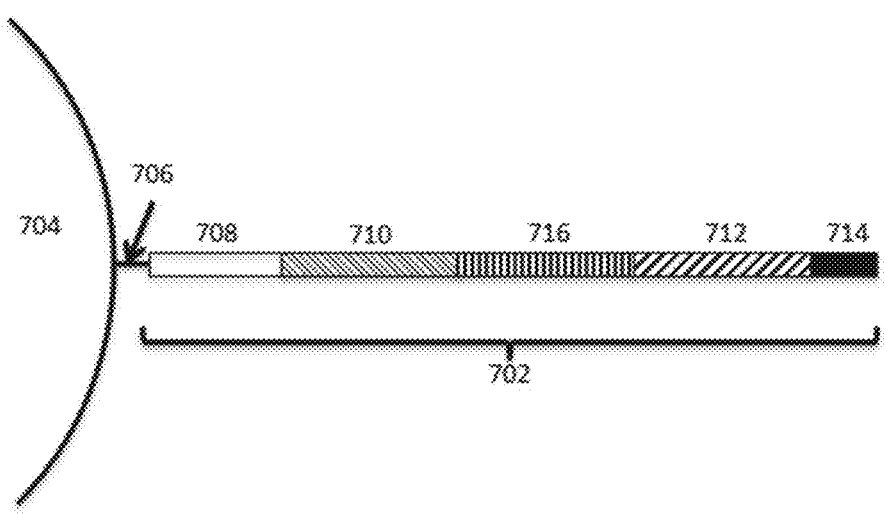
FIG. 7 provides a schematic illustration of an example barcoded oligonucleotide structure for use in analysis of ribonucleic (RNA) using the methods described herein.

In operation, and with reference to FIGS. 6 and 7, a cell is co-partitioned along with a barcode bearing bead and lysed while the barcoded oligonucleotides are released from the bead. The poly-T portion of the released barcode oligonucleotide then hybridizes to the poly-A tail of the mRNA. The poly-T segment then primes the reverse transcription of the mRNA to produce a cDNA transcript of the mRNA, but which includes each of the sequence segments 708-716 of the barcode oligonucleotide. Again, because the oligonucleotide 702 includes an anchoring sequence 714, it will more likely hybridize to and prime reverse transcription at the sequence end of the poly-A tail of the mRNA. Within any given partition, all of the cDNA transcripts of the individual mRNA molecules will include a common barcode sequence segment 710. However, by including the unique random N-mer sequence, the transcripts made from different mRNA molecules within a given partition will vary at this unique sequence. This provides a quantitation feature that can be identifiable even following any subsequent amplification of the contents of a given partition, e.g., the number of unique segments associated with a common barcode can be indicative of the quantity of mRNA originating from a single partition, and thus, a single cell. As noted above, the transcripts are then amplified, cleaned up and sequenced to identify the sequence of the cDNA transcript of the mRNA, as well as to sequence the barcode segment and the unique sequence segment.

As noted elsewhere herein, while a poly-T primer sequence is described, other targeted or random priming sequences may also be used in priming the reverse transcription reaction. Likewise, although described as releasing the barcoded oligonucleotides into the partition along with the contents of the lysed cells, it will be appreciated that in some cases, the gel bead bound oligonucleotides may be used to hybridize ad capture the mRNA on the solid phase of the gel beads, in order to facilitate the separation of the RNA from other cell contents.

Figure 9A:
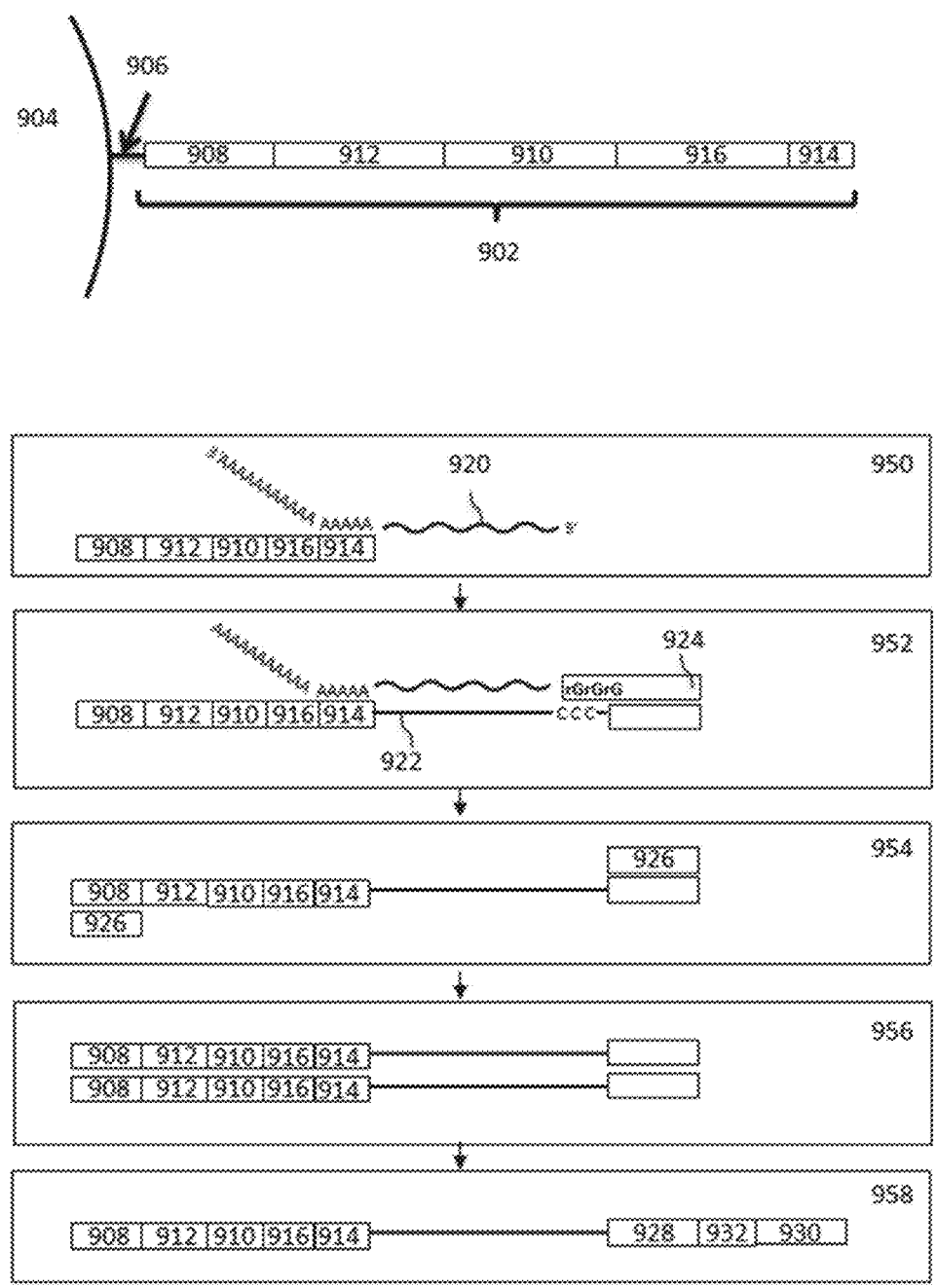

An additional example of a barcode oligonucleotide for use in RNA analysis, including messenger RNA (mRNA, including mRNA obtained from a cell) analysis, is shown in FIG. 9A. As shown, the overall oligonucleotide 902 can be coupled to a bead 904 by a releasable linkage 906, such as a disulfide linker. The oligonucleotide may include functional sequences that are used in subsequent processing, such as functional sequence 908, which may include a sequencer specific flow cell attachment sequence, e.g., a P5 sequence for Illumina sequencing systems, as well as functional sequence 910, which may include sequencing primer sequences, e.g., a R1 primer binding site for Illumina sequencing systems. A barcode sequence 912 is included within the structure for use in barcoding the sample RNA. An RNA specific (e.g., mRNA specific) priming sequence, such as poly-T sequence 914 is also included in the oligonucleotide structure. An anchoring sequence segment (not shown) may be included to ensure that the poly-T sequence hybridizes at the sequence end of the mRNA. An additional sequence segment 916 may be provided within the oligonucleotide sequence. This additional sequence can provide a unique molecular sequence segment, e.g., as a random N-mer sequence that varies across individual oligonucleotides coupled to a single bead, whereas barcode sequence 912 can be constant among oligonucleotides tethered to an individual bead. As described elsewhere herein, this unique sequence can serve to provide a unique identifier of the starting mRNA molecule that was captured, in order to allow quantitation of the number of original expressed RNA, e.g., mRNA counting. As will be appreciated, although shown as a single oligonucleotide tethered to the surface of a bead, individual beads can include tens to hundreds of thousands or even millions of individual oligonucleotide molecules, where, as noted, the barcode segment can be constant or relatively constant for a given bead, but where the variable or unique sequence segment will vary across an individual bead.

In an example method of cellular RNA (e.g., mRNA) analysis and in reference to FIG. 9A, a cell is co-partitioned along with a barcode bearing bead, switch oligo 924, and other reagents such as reverse transcriptase, a reducing agent and dNTPs into a partition (e.g., a droplet in an emulsion). In operation 950, the cell is lysed while the barcoded oligonucleotides 902 are released from the bead (e.g., via the action of the reducing agent) and the poly-T segment 914 of the released barcode oligonucleotide then hybridizes to the poly-A tail of mRNA 920 that is released from the cell. Next, in operation 952 the poly-T segment 914 is extended in a reverse transcription reaction using the mRNA as a template to produce a cDNA transcript 922 complementary to the mRNA and also includes each of the sequence segments 908, 912, 910, 916 and 914 of the barcode oligonucleotide. Terminal transferase activity of the reverse transcriptase can add additional bases to the cDNA transcript (e.g., polyC). The switch oligo 924 may then hybridize with the additional bases added to the cDNA transcript and facilitate template switching. A sequence complementary to the switch oligo sequence can then be incorporated into the cDNA transcript 922 via extension of the cDNA transcript 922 using the switch oligo 924 as a template. Within any given partition, all of the cDNA transcripts of the individual mRNA molecules will include a common barcode sequence segment 912. However, by including the unique random N-mer sequence 916, the transcripts made from different mRNA molecules within a given partition will vary at this unique sequence. As described elsewhere herein, this provides a quantitation feature that can be identifiable even following any subsequent amplification of the contents of a given partition, e.g., the number of unique segments associated with a common barcode can be indicative of the quantity of mRNA originating from a single partition, and thus, a single cell. Following operation 952, the cDNA transcript 922 is then amplified with primers 926 (e.g., PCR primers) in operation 954. Next, the amplified product is then purified (e.g., via solid phase reversible immobilization (SPRI)) in operation 956. At operation 958, the amplified product is then sheared, ligated to additional functional sequences, and further amplified (e.g., via PCR). The functional sequences may include a sequencer specific flow cell attachment sequence 930, e.g., a P7 sequence for Illumina sequencing systems, as well as functional sequence 928, which may include a sequencing primer binding site, e.g., for a R2 primer for Illumina sequencing systems, as well as functional sequence 932, which may include a sample index, e.g., an i7 sample index sequence for Illumina sequencing systems. In some cases, operations 950 and 952 can occur in the partition, while operations 954, 956 and 958 can occur in bulk solution (e.g., in a pooled mixture outside of the partition). In the case where a partition is a droplet in an emulsion, the emulsion can be broken and the contents of the droplet pooled in order to complete operations 954, 956 and 958. In some cases, operation 954 may be completed in the partition. In some cases, barcode oligonucleotides may be digested with exonucleases after the emulsion is broken. Exonuclease activity can be inhibited by ethylenediaminetetraacetic acid (EDTA) following primer digestion. Although described in terms of specific sequence references used for certain sequencing systems, e.g., Illumina systems, it will be understood that the reference to these sequences is for illustration purposes only, and the methods described herein may be configured for use with other sequencing systems incorporating specific priming, attachment, index, and other operational sequences used in those systems, e.g., systems available from Ion Torrent, Oxford Nanopore, Genia, Pacific Biosciences, Complete Genomics, and the like.

In an alternative example of a barcode oligonucleotide for use in RNA (e.g., cellular RNA) analysis as shown in FIG. 9A, functional sequence 908 may be a P7 sequence and functional sequence 910 may be a R2 primer binding site. Moreover, the functional sequence 930 may be a P5 sequence, functional sequence 928 may be a R1 primer binding site, and functional sequence 932 may be an i5 sample index sequence for Illumina sequencing systems. The configuration of the constructs generated by such a barcode oligonucleotide can help minimize (or avoid) sequencing of the poly-T sequence during sequencing.

Figure 9B:
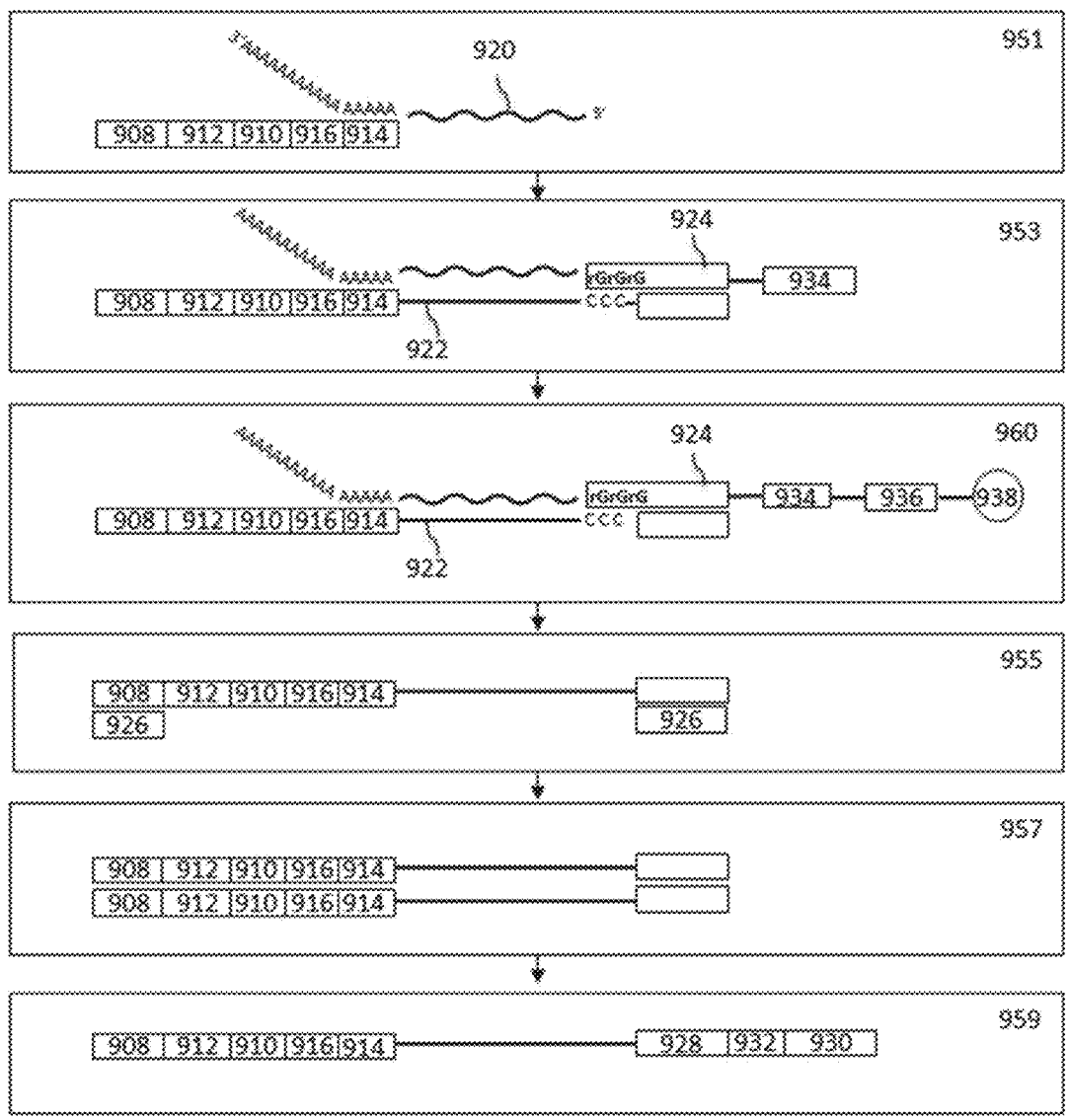

Shown in FIG. 9B is another example method for RNA analysis, including cellular mRNA analysis. In this method, the switch oligo 924 is co-partitioned with the individual cell and barcoded bead along with reagents such as reverse transcriptase, a reducing agent and dNTPs into a partition (e.g., a droplet in an emulsion). The switch oligo 924 may be labeled with an additional tag 934, e.g. biotin. In operation 951, the cell is lysed while the barcoded oligonucleotides 902 (e.g., as shown in FIG. 9A) are released from the bead (e.g., via the action of the reducing agent). In some cases, sequence 908 is a P7 sequence and sequence 910 is a R2 primer binding site. In other cases, sequence 908 is a P5 sequence and sequence 910 is a R1 primer binding site. Next, the poly-T segment 914 of the released barcode oligonucleotide hybridizes to the poly-A tail of mRNA 920 that is released from the cell. In operation 953, the poly-T segment 914 is then extended in a reverse transcription reaction using the mRNA as a template to produce a cDNA transcript 922 complementary to the mRNA and also includes each of the sequence segments 908, 912, 910, 916 and 914 of the barcode oligonucleotide. Terminal transferase activity of the reverse transcriptase can add additional bases to the cDNA transcript (e.g., polyC). The switch oligo 924 may then hybridize with the cDNA transcript and facilitate template switching. A sequence complementary to the switch oligo sequence can then be incorporated into the cDNA transcript 922 via extension of the cDNA transcript 922 using the switch oligo 924 as a template. Next, an isolation operation 960 can be used to isolate the cDNA transcript 922 from the reagents and oligonucleotides in the partition. The additional tag 934, e.g. biotin, can be contacted with an interacting tag 936, e.g., streptavidin, which may be attached to a magnetic bead 938. At operation 960 the cDNA can be isolated with a pull-down operation (e.g., via magnetic separation, centrifugation) before amplification (e.g., via PCR) in operation 955, followed by purification (e.g., via solid phase reversible immobilization (SPRI)) in operation 957 and further processing (shearing, ligation of sequences 928, 932 and 930 and subsequent amplification (e.g., via PCR)) in operation 959. In some cases where sequence 908 is a P7 sequence and sequence 910 is a R2 primer binding site, sequence 930 is a P5 sequence and sequence 928 is a R1 primer binding site and sequence 932 is an i5 sample index sequence. In some cases where sequence 908 is a P5 sequence and sequence 910 is a R1 primer binding site, sequence 930 is a P7 sequence and sequence 928 is a R2 primer binding site and sequence 932 is an i7 sample index sequence. In some cases, as shown, operations 951 and 953 can occur in the partition, while operations 960, 955, 957 and 959 can occur in bulk solution (e.g., in a pooled mixture outside of the partition). In the case where a partition is a droplet in an emulsion, the emulsion can be broken and the contents of the droplet pooled in order to complete operation 960. The operations 955, 957, and 959 can then be carried out following operation 960 after the transcripts are pooled for processing.

Figure 9C:
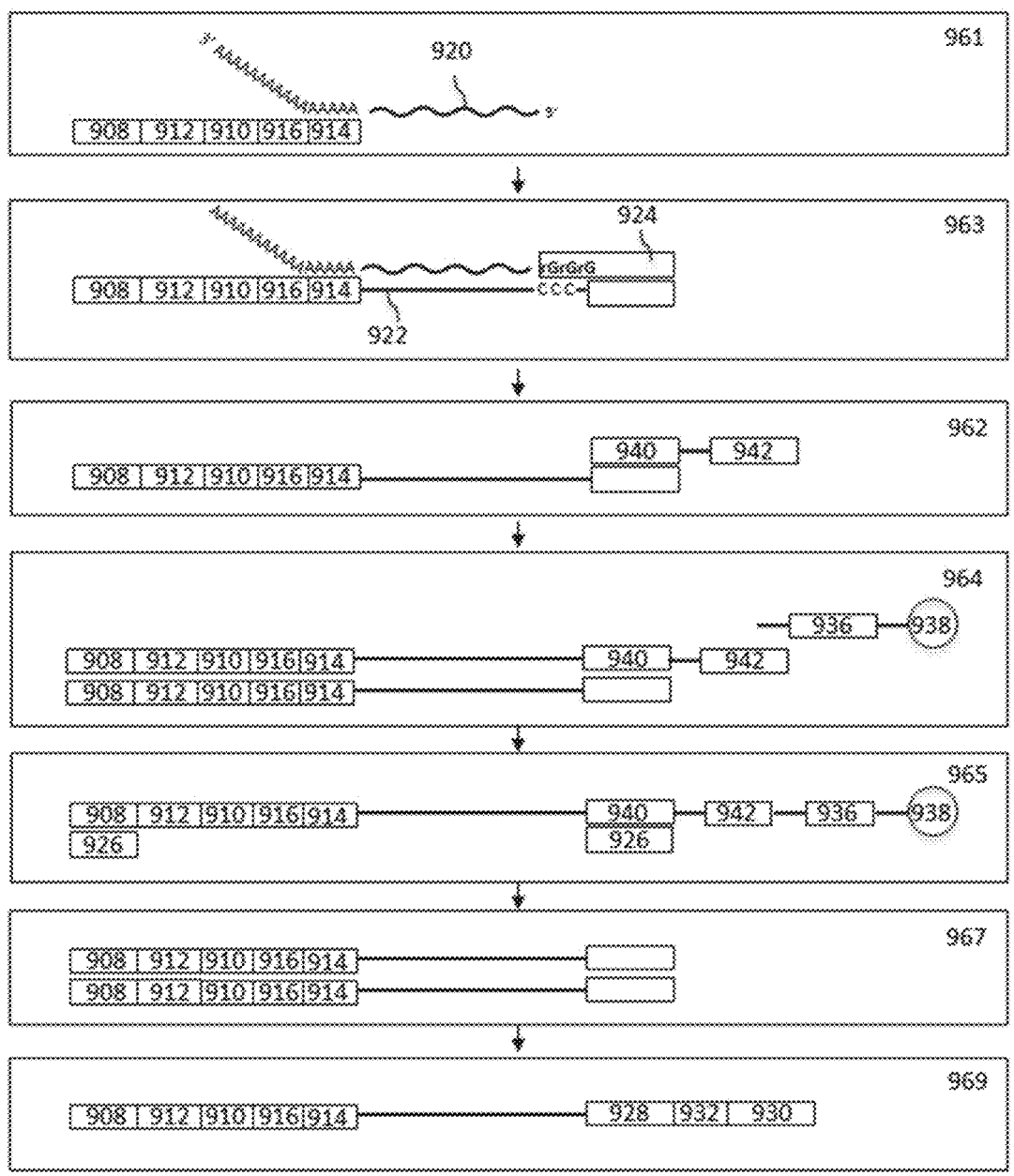

Shown in FIG. 9C is another example method for RNA analysis, including cellular mRNA analysis. In this method, the switch oligo 924 is co-partitioned with the individual cell and barcoded bead along with reagents such as reverse transcriptase, a reducing agent and dNTPs in a partition (e.g., a droplet in an emulsion). In operation 961, the cell is lysed while the barcoded oligonucleotides 902 (e.g., as shown in FIG. 9A) are released from the bead (e.g., via the action of the reducing agent). In some cases, sequence 908 is a P7 sequence and sequence 910 is a R2 primer binding site. In other cases, sequence 908 is a P5 sequence and sequence 910 is a R1 primer binding site. Next, the poly-T segment 914 of the released barcode oligonucleotide then hybridizes to the poly-A tail of mRNA 920 that is released from the cell. Next, in operation 963 the poly-T segment 914 is then extended in a reverse transcription reaction using the mRNA as a template to produce a cDNA transcript 922 complementary to the mRNA and also includes each of the sequence segments 908, 912, 910, 916 and 914 of the barcode oligonucleotide. Terminal transferase activity of the reverse transcriptase can add additional bases to the cDNA transcript (e.g., polyC). The switch oligo 924 may then hybridize with the cDNA transcript and facilitate template switching. A sequence complementary to the switch oligo sequence can then be incorporated into the cDNA transcript 922 via extension of the cDNA transcript 922 using the switch oligo 924 as a template. Following operation 961 and operation 963, mRNA 920 and cDNA transcript 922 are denatured in operation 962. At operation 964, a second strand is extended from a primer 940 having an additional tag 942, e.g. biotin, and hybridized to the cDNA transcript 922. Also in operation 964, the biotin labeled second strand can be contacted with an interacting tag 936, e.g. streptavidin, which may be attached to a magnetic bead 938. The cDNA can be isolated with a pull-down operation (e.g., via magnetic separation, centrifugation) before amplification (e.g., via polymerase chain reaction (PCR)) in operation 965, followed by purification (e.g., via solid phase reversible immobilization (SPRI)) in operation 967 and further processing (shearing, ligation of sequences 928, 932 and 930 and subsequent amplification (e.g., via PCR)) in operation 969. In some cases where sequence 908 is a P7 sequence and sequence 910 is a R2 primer binding site, sequence 930 is a P5 sequence and sequence 928 is a R1 primer binding site and sequence 932 is an i5 sample index sequence. In some cases where sequence 908 is a P5 sequence and sequence 910 is a R1 primer binding site, sequence 930 is a P7 sequence and sequence 928 is a R2 primer binding site and sequence 932 is an i7 sample index sequence. In some cases, operations 961 and 963 can occur in the partition, while operations 962, 964, 965, 967, and 969 can occur in bulk (e.g., outside the partition). In the case where a partition is a droplet in an emulsion, the emulsion can be broken and the contents of the droplet pooled in order to complete operations 962, 964, 965, 967 and 969.

Figure 9D:
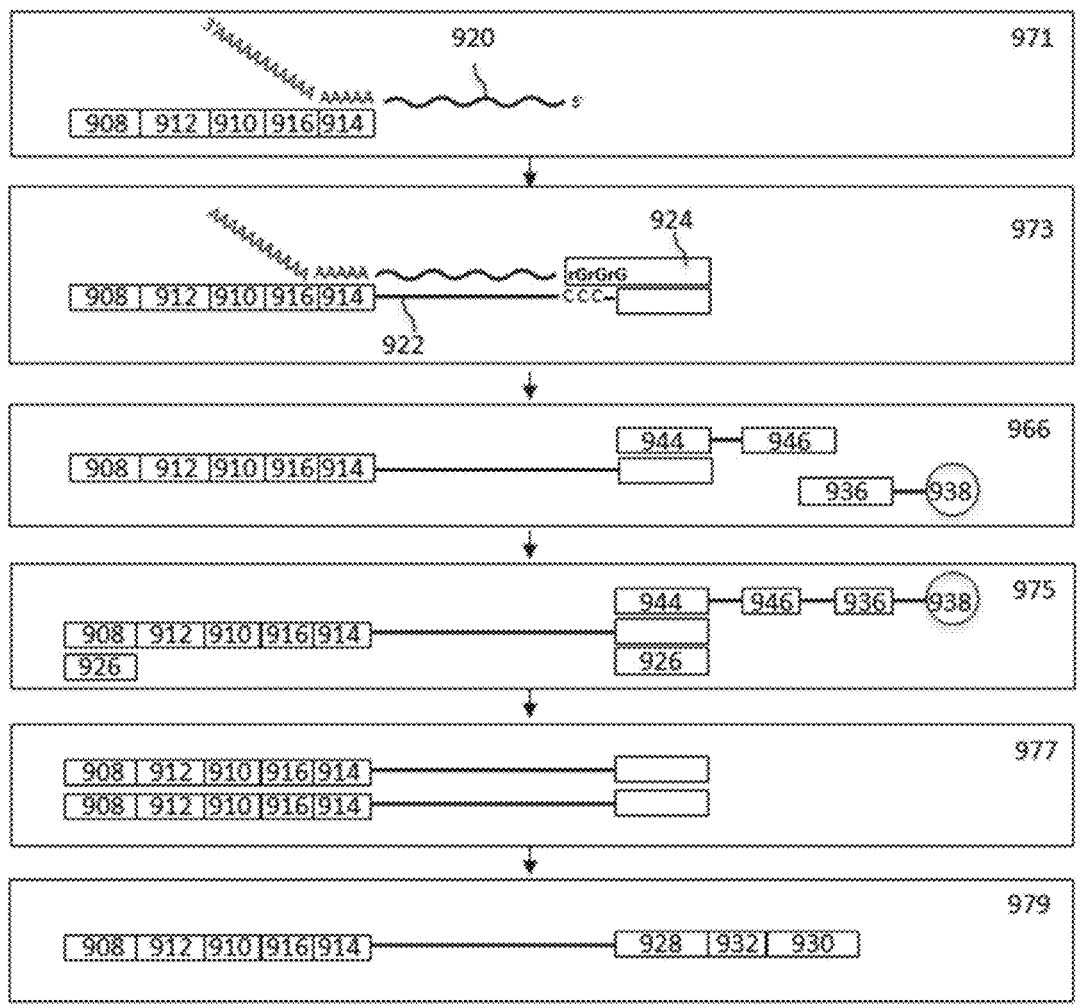

Shown in FIG. 9D is another example method for RNA analysis, including cellular mRNA analysis. In this method, the switch oligo 924 is co-partitioned with the individual cell and barcoded bead along with reagents such as reverse transcriptase, a reducing agent and dNTPs. In operation 971, the cell is lysed while the barcoded oligonucleotides 902 (e.g., as shown in FIG. 9A) are released from the bead (e.g., via the action of the reducing agent). In some cases, sequence 908 is a P7 sequence and sequence 910 is a R2 primer binding site. In other cases, sequence 908 is a P5 sequence and sequence 910 is a R1 primer binding site. Next the poly-T segment 914 of the released barcode oligonucleotide then hybridizes to the poly-A tail of mRNA 920 that is released from the cell. Next in operation 973, the poly-T segment 914 is then extended in a reverse transcription reaction using the mRNA as a template to produce a cDNA transcript 922 complementary to the mRNA and also includes each of the sequence segments 908, 912, 910, 916 and 914 of the barcode oligonucleotide. Terminal transferase activity of the reverse transcriptase can add additional bases to the cDNA transcript (e.g., polyC). The switch oligo 924 may then hybridize with the cDNA transcript and facilitate template switching. A sequence complementary to the switch oligo sequence can then be incorporated into the cDNA transcript 922 via extension of the cDNA transcript 922 using the switch oligo 924 as a template. In operation 966, the mRNA 920, cDNA transcript 922 and switch oligo 924 can be denatured, and the cDNA transcript 922 can be hybridized with a capture oligonucleotide 944 labeled with an additional tag 946, e.g. biotin. In this operation, the biotin-labeled capture oligonucleotide 944, which is hybridized to the cDNA transcript, can be contacted with an interacting tag 936, e.g. streptavidin, which may be attached to a magnetic bead 938. Following separation from other species (e.g., excess barcoded oligonucleotides) using a pull-down operation (e.g., via magnetic separation, centrifugation), the cDNA transcript can be amplified (e.g., via PCR) with primers 926 at operation 975, followed by purification (e.g., via solid phase reversible immobilization (SPRI)) in operation 977 and further processing (shearing, ligation of sequences 928, 932 and 930 and subsequent amplification (e.g., via PCR)) in operation 979. In some cases where sequence 908 is a P7 sequence and sequence 910 is a R2 primer binding site, sequence 930 is a P5 sequence and sequence 928 is a R1 primer binding site and sequence 932 is an i5 sample index sequence. In other cases where sequence 908 is a P5 sequence and sequence 910 is a R1 primer binding site, sequence 930 is a P7 sequence and sequence 928 is a R2 primer binding site and sequence 932 is an i7 sample index sequence. In some cases, operations 971 and 973 can occur in the partition, while operations 966, 975, 977 (purification), and 979 can occur in bulk (e.g., outside the partition). In the case where a partition is a droplet in an emulsion, the emulsion can be broken and the contents of the droplet pooled in order to complete operations 966, 975, 977 and 979.

Figure 9E:
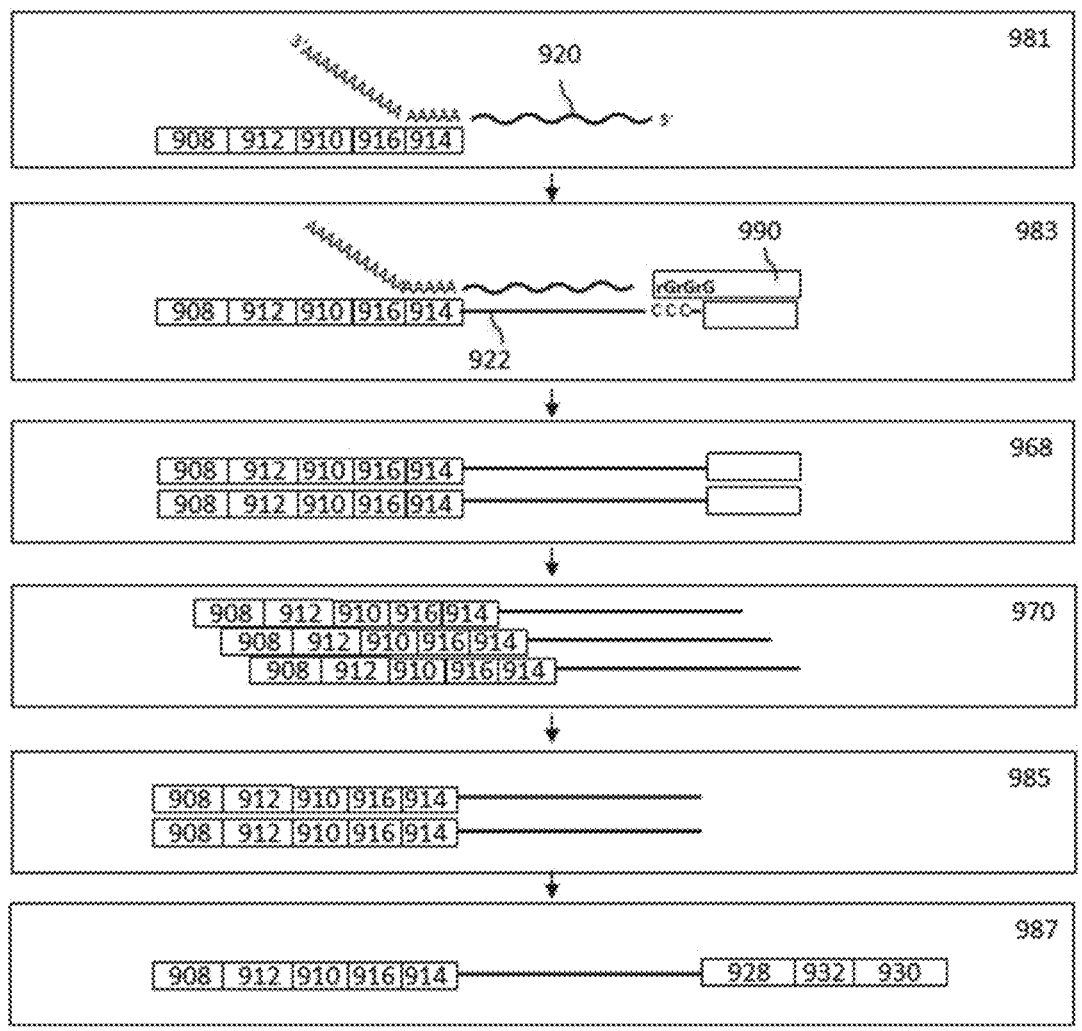

Shown in FIG. 9E is another example method for RNA analysis, including cellular RNA analysis. In this method, an individual cell is co-partitioned along with a barcode bearing bead, a switch oligo 990, and other reagents such as reverse transcriptase, a reducing agent and dNTPs into a partition (e.g., a droplet in an emulsion). In operation 981, the cell is lysed while the barcoded oligonucleotides (e.g., 902 as shown in FIG. 9A) are released from the bead (e.g., via the action of the reducing agent). In some cases, sequence 908 is a P7 sequence and sequence 910 is a R2 primer binding site. In other cases, sequence 908 is a P5 sequence and sequence 910 is a R1 primer binding site. Next, the poly-T segment of the released barcode oligonucleotide then hybridizes to the poly-A tail of mRNA 920 released from the cell. Next at operation 983, the poly-T segment is then extended in a reverse transcription reaction to produce a cDNA transcript 922 complementary to the mRNA and also includes each of the sequence segments 908, 912, 910, 916 and 914 of the barcode oligonucleotide. Terminal transferase activity of the reverse transcriptase can add additional bases to the cDNA transcript (e.g., polyC). The switch oligo 990 may then hybridize with the cDNA transcript and facilitate template switching. A sequence complementary to the switch oligo sequence and including a T7 promoter sequence, can be incorporated into the cDNA transcript 922. At operation 968, a second strand is synthesized and at operation 970 the T7 promoter sequence can be used by T7 polymerase to produce RNA transcripts in in vitro transcription. At operation 985 the RNA transcripts can be purified (e.g., via solid phase reversible immobilization (SPRI)), reverse transcribed to form DNA transcripts, and a second strand can be synthesized for each of the DNA transcripts. In some cases, prior to purification, the RNA transcripts can be contacted with a DNase (e.g., DNAase I) to break down residual DNA. At operation 987 the DNA transcripts are then fragmented and ligated to additional functional sequences, such as sequences 928, 932 and 930 and, in some cases, further amplified (e.g., via PCR). In some cases where sequence 908 is a P7 sequence and sequence 910 is a R2 primer binding site, sequence 930 is a P5 sequence and sequence 928 is a R1 primer binding site and sequence 932 is an i5 sample index sequence. In some cases where sequence 908 is a P5 sequence and sequence 910 is a R1 primer binding site, sequence 930 is a P7 sequence and sequence 928 is a R2 primer binding site and sequence 932 is an i7 sample index sequence. In some cases, prior to removing a portion of the DNA transcripts, the DNA transcripts can be contacted with an RNase to break down residual RNA. In some cases, operations 981 and 983 can occur in the partition, while operations 968, 970, 985 and 987 can occur in bulk (e.g., outside the partition). In the case where a partition is a droplet in an emulsion, the emulsion can be broken and the contents of the droplet pooled in order to complete operations 968, 970, 985 and 987.

Figure 10:
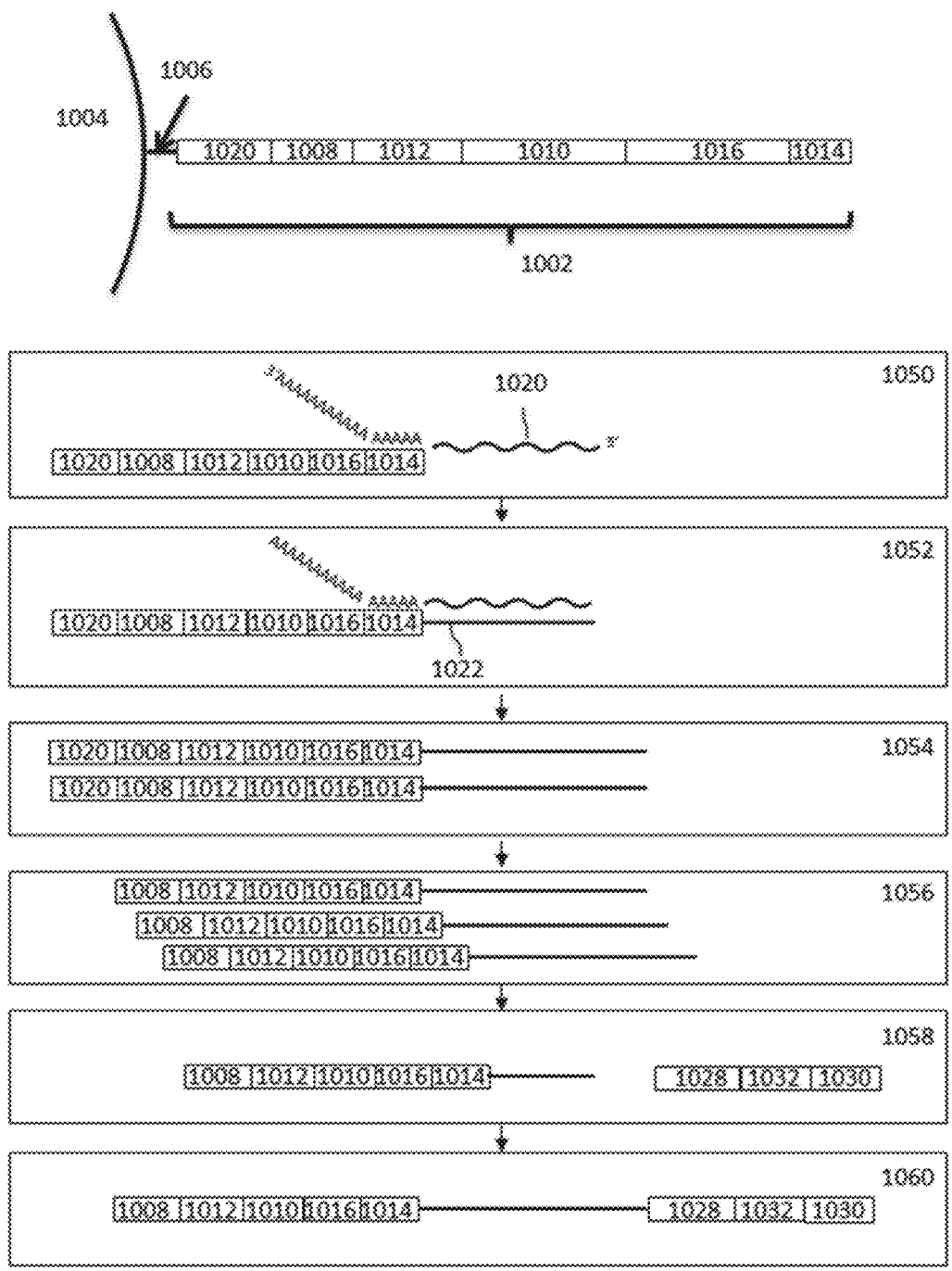
FIG. 10 provides schematic illustration of example barcoded oligonucleotide structure for use in example analysis of RNA and use of a sequence for in vitro transcription.

Another example of a barcode oligonucleotide for use in RNA analysis, including messenger RNA (mRNA, including mRNA obtained from a cell) analysis is shown in FIG. 10. As shown, the overall oligonucleotide 1002 is coupled to a bead 1004 by a releasable linkage 1006, such as a disulfide linker. The oligonucleotide may include functional sequences that are used in subsequent processing, such as functional sequence 1008, which may include a sequencer specific flow cell attachment sequence, e.g., a P7 sequence, as well as functional sequence 1010, which may include sequencing primer sequences, e.g., a R2 primer binding site. A barcode sequence 1012 is included within the structure for use in barcoding the sample RNA. An RNA specific (e.g., mRNA specific) priming sequence, such as poly-T sequence 1014 may be included in the oligonucleotide structure. An anchoring sequence segment (not shown) may be included to ensure that the poly-T sequence hybridizes at the sequence end of the mRNA. An additional sequence segment 1016 may be provided within the oligonucleotide sequence. This additional sequence can provide a unique molecular sequence segment, as described elsewhere herein. An additional functional sequence 1020 may be included for in vitro transcription, e.g., a T7 RNA polymerase promoter sequence. As will be appreciated, although shown as a single oligonucleotide tethered to the surface of a bead, individual beads can include tens to hundreds of thousands or even millions of individual oligonucleotide molecules, where, as noted, the barcode segment can be constant or relatively constant for a given bead, but where the variable or unique sequence segment will vary across an individual bead.

In an example method of cellular RNA analysis and in reference to FIG. 10, a cell is co-partitioned along with a barcode bearing bead, and other reagents such as reverse transcriptase, reducing agent and dNTPs into a partition (e.g., a droplet in an emulsion). In operation 1050, the cell is lysed while the barcoded oligonucleotides 1002 are released (e.g., via the action of the reducing agent) from the bead, and the poly-T segment 1014 of the released barcode oligonucleotide then hybridizes to the poly-A tail of mRNA 1020. Next at operation 1052, the poly-T segment is then extended in a reverse transcription reaction using the mRNA as template to produce a cDNA transcript 1022 of the mRNA and also includes each of the sequence segments 1020, 1008, 1012, 1010, 1016, and 1014 of the barcode oligonucleotide. Within any given partition, all of the cDNA transcripts of the individual mRNA molecules will include a common barcode sequence segment 1012. However, by including the unique random N-mer sequence, the transcripts made from different mRNA molecules within a given partition will vary at this unique sequence. As described elsewhere herein, this provides a quantitation feature that can be identifiable even following any subsequent amplification of the contents of a given partition, e.g., the number of unique segments associated with a common barcode can be indicative of the quantity of mRNA originating from a single partition, and thus, a single cell. At operation 1054 a second strand is synthesized and at operation 1056 the T7 promoter sequence can be used by T7 polymerase to produce RNA transcripts in in vitro transcription. At operation 1058 the transcripts are fragmented (e.g., sheared), ligated to additional functional sequences, and reverse transcribed. The functional sequences may include a sequencer specific flow cell attachment sequence 1030, e.g., a P5 sequence, as well as functional sequence 1028, which may include sequencing primers, e.g., a R1 primer binding sequence, as well as functional sequence 1032, which may include a sample index, e.g., an i5 sample index sequence. At operation 1060 the RNA transcripts can be reverse transcribed to DNA, the DNA amplified (e.g., via PCR), and sequenced to identify the sequence of the cDNA transcript of the mRNA, as well as to sequence the barcode segment and the unique sequence segment. In some cases, operations 1050 and 1052 can occur in the partition, while operations 1054, 1056, 1058 and 1060 can occur in bulk (e.g., outside the partition). In the case where a partition is a droplet in an emulsion, the emulsion can be broken and the contents of the droplet pooled in order to complete operations 1054, 1056, 1058 and 1060.

In an alternative example of a barcode oligonucleotide for use in RNA (e.g., cellular RNA) analysis as shown in FIG. 10, functional sequence 1008 may be a P5 sequence and functional sequence 1010 may be a R1 primer binding site. Moreover, the functional sequence 1030 may be a P7 sequence, functional sequence 1028 may be a R2 primer binding site, and functional sequence 1032 may be an i7 sample index sequence.

Figure 11:
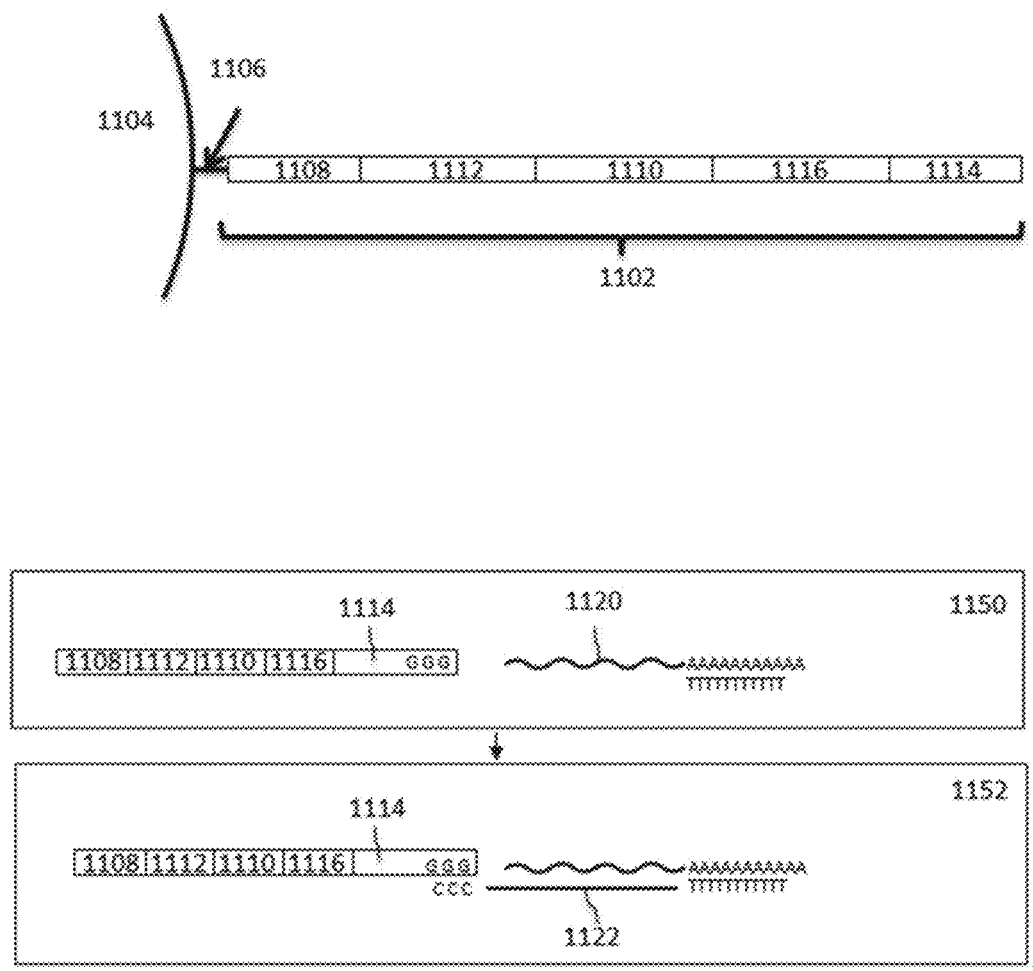
FIG. 11 provides schematic illustration of an example barcoded oligonucleotide structure for use in analysis of RNA and example operations for performing RNA analysis.

An additional example of a barcode oligonucleotide for use in RNA analysis, including messenger RNA (mRNA, including mRNA obtained from a cell) analysis is shown in FIG. 11. As shown, the overall oligonucleotide 1102 is coupled to a bead 1104 by a releasable linkage 1106, such as a disulfide linker. The oligonucleotide may include functional sequences that are used in subsequent processing, such as functional sequence 1108, which may include a sequencer specific flow cell attachment sequence, e.g., a P5 sequence, as well as functional sequence 1110, which may include sequencing primer sequences, e.g., a R1 primer binding site. In some cases, sequence 1108 is a P7 sequence and sequence 1110 is a R2 primer binding site. A barcode sequence 1112 is included within the structure for use in barcoding the sample RNA. An additional sequence segment 1116 may be provided within the oligonucleotide sequence. In some cases, this additional sequence can provide a unique molecular sequence segment, as described elsewhere herein. An additional sequence 1114 may be included to facilitate template switching, e.g., polyG. As will be appreciated, although shown as a single oligonucleotide tethered to the surface of a bead, individual beads can include tens to hundreds of thousands or even millions of individual oligonucleotide molecules, where, as noted, the barcode segment can be constant or relatively constant for a given bead, but where the variable or unique sequence segment will vary across an individual bead.

In an example method of cellular mRNA analysis and in reference to FIG. 11, a cell is co-partitioned along with a barcode bearing bead, poly-T sequence, and other reagents such as reverse transcriptase, a reducing agent and dNTPs into a partition (e.g., a droplet in an emulsion). In operation 1150, the cell is lysed while the barcoded oligonucleotides are released from the bead (e.g., via the action of the reducing agent) and the poly-T sequence hybridizes to the poly-A tail of mRNA 1120 released from the cell. Next, in operation 1152, the poly-T sequence is then extended in a reverse transcription reaction using the mRNA as a template to produce a cDNA transcript 1122 complementary to the mRNA. Terminal transferase activity of the reverse transcriptase can add additional bases to the cDNA transcript (e.g., polyC). The additional bases added to the cDNA transcript, e.g., polyC, can then to hybridize with 1114 of the barcoded oligonucleotide. This can facilitate template switching and a sequence complementary to the barcode oligonucleotide can be incorporated into the cDNA transcript. The transcripts can be further processed (e.g., amplified, portions removed, additional sequences added, etc.) and characterized as described elsewhere herein, e.g., by sequencing. The configuration of the constructs generated by such a method can help minimize (or avoid) sequencing of the poly-T sequence during sequencing.

Figure 12A:
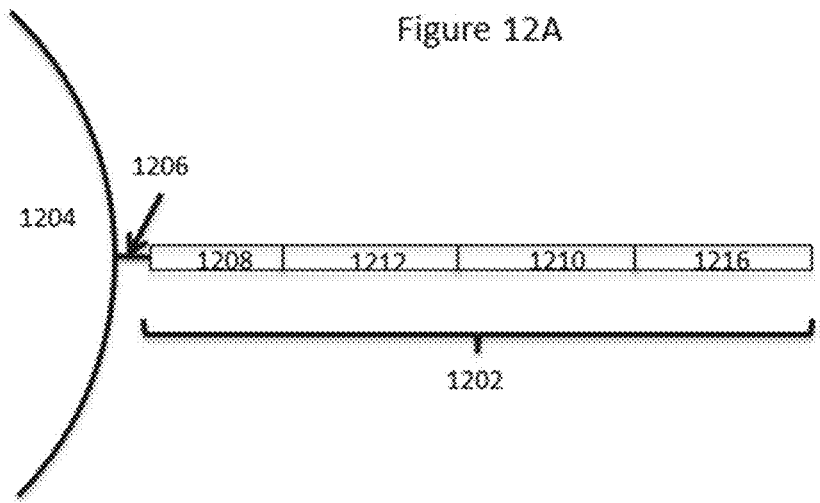
FIG. 12A-B provides schematic illustration of example barcoded oligonucleotide structure for use in analysis of RNA.

An additional example of a barcode oligonucleotide for use in RNA analysis, including cellular RNA analysis is shown in FIG. 12A. As shown, the overall oligonucleotide 1202 is coupled to a bead 1204 by a releasable linkage 1206, such as a disulfide linker. The oligonucleotide may include functional sequences that are used in subsequent processing, such as functional sequence 1208, which may include a sequencer specific flow cell attachment sequence, e.g., a P5 sequence, as well as functional sequence 1210, which may include sequencing primer sequences, e.g., a R1 primer binding site. In some cases, sequence 1208 is a P7 sequence and sequence 1210 is a R2 primer binding site. A barcode sequence 1212 is included within the structure for use in barcoding the sample RNA. An additional sequence segment 1216 may be provided within the oligonucleotide sequence. In some cases, this additional sequence can provide a unique molecular sequence segment, as described elsewhere herein. As will be appreciated, although shown as a single oligonucleotide tethered to the surface of a bead, individual beads can include tens to hundreds of thousands or even millions of individual oligonucleotide molecules, where, as noted, the barcode segment can be constant or relatively constant for a given bead, but where the variable or unique sequence segment will vary across an individual bead. In an example method of cellular RNA analysis using this barcode, a cell is co-partitioned along with a barcode bearing bead and other reagents such as RNA ligase and a reducing agent into a partition (e.g. a droplet in an emulsion). The cell is lysed while the barcoded oligonucleotides are released (e.g., via the action of the reducing agent) from the bead. The barcoded oligonucleotides can then be ligated to the 5' end of mRNA transcripts while in the partitions by RNA ligase. Subsequent operations may include purification (e.g., via solid phase reversible immobilization (SPRI)) and further processing (shearing, ligation of functional sequences, and subsequent amplification (e.g., via PCR)), and these operations may occur in bulk (e.g., outside the partition). In the case where a partition is a droplet in an emulsion, the emulsion can be broken and the contents of the droplet pooled for the additional operations.

Figure 12B:
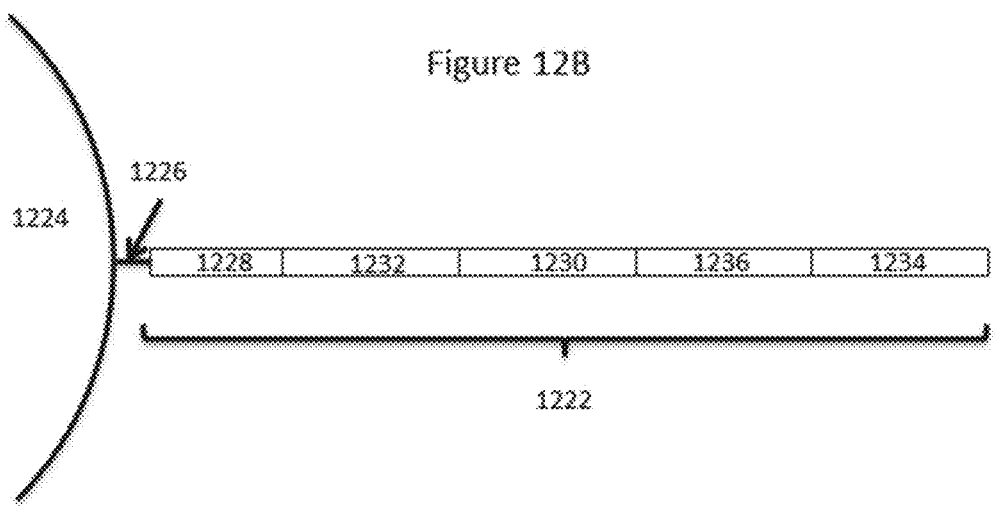

An additional example of a barcode oligonucleotide for use in RNA analysis, including cellular RNA analysis is shown in FIG. 12B. As shown, the overall oligonucleotide 1222 is coupled to a bead 1224 by a releasable linkage 1226, such as a disulfide linker. The oligonucleotide may include functional sequences that are used in subsequent processing, such as functional sequence 1228, which may include a sequencer specific flow cell attachment sequence, e.g., a P5 sequence, as well as functional sequence 1230, which may include sequencing primer sequences, e.g., a R1 primer binding site. In some cases, sequence 1228 is a P7 sequence and sequence 1230 is a R2 primer binding site. A barcode sequence 1232 is included within the structure for use in barcoding the sample RNA. A priming sequence 1234 (e.g., a random priming sequence) can also be included in the oligonucleotide structure, e.g., a random hexamer. An additional sequence segment 1236 may be provided within the oligonucleotide sequence. In some cases, this additional sequence provides a unique molecular sequence segment, as described elsewhere herein. As will be appreciated, although shown as a single oligonucleotide tethered to the surface of a bead, individual beads can include tens to hundreds of thousands or even millions of individual oligonucleotide molecules, where, as noted, the barcode segment can be constant or relatively constant for a given bead, but where the variable or unique sequence segment will vary across an individual bead. In an example method of cellular mRNA analysis using the barcode oligonucleotide of FIG. 12B, a cell is co-partitioned along with a barcode bearing bead and additional reagents such as reverse transcriptase, a reducing agent and dNTPs into a partition (e.g., a droplet in an emulsion). The cell is lysed while the barcoded oligonucleotides are released from the bead (e.g., via the action of the reducing agent). In some cases, sequence 1228 is a P7 sequence and sequence 1230 is a R2 primer binding site. In other cases, sequence 1228 is a P5 sequence and sequence 1230 is a R1 primer binding site. The priming sequence 1234 of random hexamers can randomly hybridize cellular mRNA. The random hexamer sequence can then be extended in a reverse transcription reaction using mRNA from the cell as a template to produce a cDNA transcript complementary to the mRNA and also includes each of the sequence segments 1228, 1232, 1230, 1236, and 1234 of the barcode oligonucleotide. Subsequent operations may include purification (e.g., via solid phase reversible immobilization (SPRI)), further processing (shearing, ligation of functional sequences, and subsequent amplification (e.g., via PCR)), and these operations may occur in bulk (e.g., outside the partition). In the case where a partition is a droplet in an emulsion, the emulsion can be broken and the contents of the droplet pooled for additional operations. Additional reagents that may be co-partitioned along with the barcode bearing bead may include oligonucleotides to block ribosomal RNA (rRNA) and nucleases to digest genomic DNA and cDNA from cells. Alternatively, rRNA removal agents may be applied during additional processing operations. The configuration of the constructs generated by such a method can help minimize (or avoid) sequencing of the poly-T sequence during sequencing.

The single cell analysis methods described herein may also be useful in the analysis of the whole transcriptome. Referring back to the barcode of FIG. 12B, the priming sequence 1234 may be a random N-mer. In some cases, sequence 1228 is a P7 sequence and sequence 1230 is a R2 primer binding site. In other cases, sequence 1228 is a P5 sequence and sequence 1230 is a R1 primer binding site. In an example method of whole transcriptome analysis using this barcode, the individual cell is co-partitioned along with a barcode bearing bead, poly-T sequence, and other reagents such as reverse transcriptase, polymerase, a reducing agent and dNTPs into a partition (e.g., droplet in an emulsion). In an operation of this method, the cell is lysed while the barcoded oligonucleotides are released from the bead (e.g., via the action of the reducing agent) and the poly-T sequence hybridizes to the poly-A tail of cellular mRNA. In a reverse transcription reaction using the mRNA as template, cDNA transcripts of cellular mRNA can be produced. The RNA can then be degraded with an RNase. The priming sequence 1234 in the barcoded oligonucleotide can then randomly hybridize to the cDNA transcripts. The oligonucleotides can be extended using polymerase enzymes and other extension reagents co-partitioned with the bead and cell similar to as shown in FIG. 3 to generate amplification products (e.g., barcoded fragments), similar to the example amplification product shown in FIG. 3 (panel F). The barcoded nucleic acid fragments may, in some cases subjected to further processing (e.g., amplification, addition of additional sequences, clean up processes, etc. as described elsewhere herein) characterized, e.g., through sequence analysis. In this operation, sequencing signals can come from full length RNA.

Although operations with various barcode designs have been discussed individually, individual beads can include barcode oligonucleotides of various designs for simultaneous use.

In addition to characterizing individual cells or cell subpopulations from larger populations, the processes and systems described herein may also be used to characterize individual cells as a way to provide an overall profile of a cellular, or other organismal population. A variety of applications require the evaluation of the presence and quantification of different cell or organism types within a population of cells, including, for example, microbiome analysis and characterization, environmental testing, food safety testing, epidemiological analysis, e.g., in tracing contamination or the like. In particular, the analysis processes described above may be used to individually characterize, sequence and/or identify large numbers of individual cells within a population. This characterization may then be used to assemble an overall profile of the originating population, which can provide important prognostic and diagnostic information.

For example, shifts in human microbiomes, including, e.g., gut, buccal, epidermal microbiomes, etc., have been identified as being both diagnostic and prognostic of different conditions or general states of health. Using the single cell analysis methods and systems described herein, one can again, characterize, sequence and identify individual cells in an overall population, and identify shifts within that population that may be indicative of diagnostic ally relevant factors. By way of example, sequencing of bacterial 16S ribosomal RNA genes has been used as a highly accurate method for taxonomic classification of bacteria. Using the targeted amplification and sequencing processes described above can provide identification of individual cells within a population of cells. One may further quantify the numbers of different cells within a population to identify current states or shifts in states over time. See, e.g., Morgan et al, PLoS Comput. Biol., Ch. 12, December 2012, 8(12):e1002808, and Ram et al., Syst. Biol. Reprod. Med., June 2011, 57(3):162-170, each of which is incorporated herein by reference in its entirety for all purposes. Likewise, identification and diagnosis of infection or potential infection may also benefit from the single cell analyses described herein, e.g., to identify microbial species present in large mixes of other cells or other biological material, cells and/or nucleic acids, including the environments described above, as well as any other diagnostically relevant environments, e.g., cerebrospinal fluid, blood, fecal or intestinal samples, or the like.

The foregoing analyses may also be particularly useful in the characterization of potential drug resistance of different cells, e.g., cancer cells, bacterial pathogens, etc., through the analysis of distribution and profiling of different resistance markers/mutations across cell populations in a given sample. Additionally, characterization of shifts in these markers/mutations across populations of cells over time can provide valuable insight into the progression, alteration, prevention, and treatment of a variety of diseases characterized by such drug resistance issues.

Although described in terms of cells, it will be appreciated that any of a variety of individual biological organisms, or components of organisms are encompassed within this description, including, for example, cells, viruses, organelles, cellular inclusions, vesicles, or the like. Additionally, where referring to cells, it will be appreciated that such reference includes any type of cell, including without limitation prokaryotic cells, eukaryotic cells, bacterial, fungal, plant, mammalian, or other animal cell types, mycoplasmas, normal tissue cells, tumor cells, or any other cell type, whether derived from single cell or multicellular organisms.

Similarly, analysis of different environmental samples to profile the microbial organisms, viruses, or other biological contaminants that are present within such samples, can provide important information about disease epidemiology, and potentially aid in forecasting disease outbreaks, epidemics an pandemics.

As described above, the methods, systems and compositions described herein may also be used for analysis and characterization of other aspects of individual cells or populations of cells. In one example process, a sample is provided that contains cells that are to be analyzed and characterized as to their cell surface proteins. Also provided is a library of antibodies, antibody fragments, or other molecules having a binding affinity to the cell surface proteins or antigens (or other cell features) for which the cell is to be characterized (also referred to herein as cell surface feature binding groups). For ease of discussion, these affinity groups are referred to herein as binding groups. The binding groups can include a reporter molecule that is indicative of the cell surface feature to which the binding group binds. In particular, a binding group type that is specific to one type of cell surface feature will comprise a first reporter molecule, while a binding group type that is specific to a different cell surface feature will have a different reporter molecule associated with it. In some aspects, these reporter molecules will comprise oligonucleotide sequences. Oligonucleotide based reporter molecules provide advantages of being able to generate significant diversity in terms of sequence, while also being readily attachable to most biomolecules, e.g., antibodies, etc., as well as being readily detected, e.g., using sequencing or array technologies. In the example process, the binding groups include oligonucleotides attached to them. Thus, a first binding group type, e.g., antibodies to a first type of cell surface feature, will have associated with it a reporter oligonucleotide that has a first nucleotide sequence. Different binding group types, e.g., antibodies having binding affinity for other, different cell surface features, will have associated therewith reporter oligonucleotides that comprise different nucleotide sequences, e.g., having a partially or completely different nucleotide sequence. In some cases, for each type of cell surface feature binding group, e.g., antibody or antibody fragment, the reporter oligonucleotide sequence may be known and readily identifiable as being associated with the known cell surface feature binding group. These oligonucleotides may be directly coupled to the binding group, or they may be attached to a bead, molecular lattice, e.g., a linear, globular, cross-linked, or other polymer, or other framework that is attached or otherwise associated with the binding group, which allows attachment of multiple reporter oligonucleotides to a single binding group.

In the case of multiple reporter molecules coupled to a single binding group, such reporter molecules can comprise the same sequence, or a particular binding group will include a known set of reporter oligonucleotide sequences. As between different binding groups, e.g., specific for different cell surface features, the reporter molecules can be different and attributable to the particular binding group.

Attachment of the reporter groups to the binding groups may be achieved through any of a variety of direct or indirect, covalent or non-covalent associations or attachments. For example, in the case of oligonucleotide reporter groups associated with antibody based binding groups, such oligonucleotides may be covalently attached to a portion of an antibody or antibody fragment using chemical conjugation techniques (e.g., Lightning-Link® antibody labeling kits available from Innova Biosciences), as well as other non-covalent attachment mechanisms, e.g., using biotinylated antibodies and oligonucleotides (or beads that include one or more biotinylated linker, coupled to oligonucleotides) with an avidin or streptavidin linker. Antibody and oligonucleotide biotinylation techniques are available (See, e.g., Fang, et al., *Fluoride-Cleavable Biotinylation Phosphoramidite for 5'-end-Labeling and Affinity Purification of Synthetic Oligonucleotides*, Nucleic Acids Res. Jan. 15, 2003; 31(2):708-715, DNA 3' End Biotinylation Kit, available from Thermo Scientific, the full disclosures of which are incorporated herein by reference in their entirety for all purposes). Likewise, protein and peptide biotinylation techniques have been developed and are readily available (See, e.g., U.S. Pat. No. 6,265,552, the full disclosures of which are incorporated herein by reference in their entirety for all purposes).

The reporter oligonucleotides may be provided having any of a range of different lengths, depending upon the diversity of reporter molecules desired or a given analysis, the sequence detection scheme employed, and the like. In some cases, these reporter sequences can be greater than about 5 nucleotides in length, greater than about 10 nucleotides in length, greater than about 20, 30, 40, 50, 60, 70, 80, 90, 100, 120, 150 or even 200 nucleotides in length. In some cases, these reporter nucleotides may be less than about 250 nucleotides in length, less than about 200, 180, 150, 120 100, 90, 80, 70, 60, 50, 40, or even 30 nucleotides in length. In many cases, the reporter oligonucleotides may be selected to provide barcoded products that are already sized, and otherwise configured to be analyzed on a sequencing system. For example, these sequences may be provided at a length that ideally creates sequenceable products of a desired length for particular sequencing systems. Likewise, these reporter oligonucleotides may include additional sequence elements, in addition to the reporter sequence, such as sequencer attachment sequences, sequencing primer sequences, amplification primer sequences, or the complements to any of these.

In operation, a cell-containing sample is incubated with the binding molecules and their associated reporter oligonucleotides, for any of the cell surface features desired to be analyzed. Following incubation, the cells are washed to remove unbound binding groups. Following washing, the cells are partitioned into separate partitions, e.g., droplets, along with the barcode carrying beads described above, where each partition includes a limited number of cells, e.g., in some cases, a single cell. Upon releasing the barcodes from the beads, they will prime the amplification and barcoding of the reporter oligonucleotides. As noted above, the barcoded replicates of the reporter molecules may additionally include functional sequences, such as primer sequences, attachment sequences or the like.

The barcoded reporter oligonucleotides are then subjected to sequence analysis to identify which reporter oligonucleotides bound to the cells within the partitions. Further, by also sequencing the associated barcode sequence, one can identify that a given cell surface feature likely came from the same cell as other, different cell surface features, whose reporter sequences include the same barcode sequence, i.e., they were derived from the same partition.

Based upon the reporter molecules that emanate from an individual partition based upon the presence of the barcode sequence, one may then create a cell surface profile of individual cells from a population of cells. Profiles of individual cells or populations of cells may be compared to profiles from other cells, e.g., 'normal' cells, to identify variations in cell surface features, which may provide diagnostically relevant information. In particular, these profiles may be particularly useful in the diagnosis of a variety of disorders that are characterized by variations in cell surface receptors, such as cancer and other disorders.

Methods of the disclosure may be applicable to processing samples for the detection of changes in gene expression. A sample may comprise a cell, mRNA, or cDNA reverse transcribed from mRNA. The sample may be a pooled sample, comprising extracts from several different cells or tissues, or a sample comprising extracts from a single cell or tissue.

methods of the invention may be used to fragment and barcode the polynucleotides of the cell for Cells may be placed directly into a partition (e.g., a microwell) and lysed. After lysis, the sequencing. Polynucleotides may also be extracted from cells prior to introducing them into a partition used in a method of the invention. Reverse transcription of mRNA may be performed in a partition described herein, or outside of such a partition. Sequencing cDNA may provide an indication of the abundance of a particular transcript in a particular cell over time, or after exposure to a particular condition.

It may be desirable to retain the option of identifying and tracking individual molecules or analytes after or during sample preparation. In some cases, one or more unique molecular identifiers, sometimes known in the art as a 'molecular barcodes,' are used as sample preparation reagents. These molecules may comprise a variety of different forms such as oligonucleotide bar codes, antibodies or antibody fragments, fluorophores, nanoparticles, and other elements or combinations thereof. Depending upon the specific application, molecular barcodes may reversibly or irreversibly bind to the target analyte and allow for identification and/or quantification of individual analytes after recovery from a device after sample preparation.

A device of this disclosure may be applicable to nucleic acid sequencing, protein detection, single molecule analysis and other methods that require a) precise measurement of the presence and amount of a specific analyte b) multiplex reactions in which multiple analytes are pooled for analysis. A device of this disclosure may utilize the microwells of the microwell array or other type of partition (e.g., droplets) to physically partition target analytes. This physical partitioning allows for individual analytes to acquire one or more molecular barcodes. After sample preparation, individual analytes may be pooled or combined and extracted from a device for multiplex analysis. For most applications, multiplex analysis substantially decreases the cost of analysis as well as increases through-put of the process, such as in the case of the nucleic acid sequencing. Molecular barcodes may allow for the identification and quantification of individual molecules even after pooling of a plurality of analytes. For example, with respect to nucleic acid sequencing, molecular barcodes may permit the sequencing of individual nucleic acids, even after the pooling of a plurality of different nucleic acids.

Oligonucleotide barcodes, in some cases, may be particularly useful in nucleic acid sequencing. In general, an oligonucleotide barcode may comprise a unique sequence (e.g., a barcode sequence) that gives the oligonucleotide barcode its identifying functionality. The unique sequence may be random or non-random. Attachment of the barcode sequence to a nucleic acid of interest may associate the barcode sequence with the nucleic acid of interest. The barcode may then be used to identify the nucleic acid of interest during sequencing, even when other nucleic acids of interest (e.g., comprising different barcodes) are present. In cases where a nucleic acid of interest is fragmented prior to sequencing, an attached barcode may be used to identify fragments as belonging to the nucleic acid of interest during sequencing.

An oligonucleotide barcode may consist solely of a unique barcode sequence or may be included as part of an oligonucleotide of longer sequence length. Such an oligonucleotide may be an adaptor required for a particular sequencing chemistry and/or method. For example, such adaptors may include, in addition to an oligonucleotide barcode, immobilization sequence regions necessary to immobilize (e.g., via hybridization) the adaptor to a solid surface (e.g., solid surfaces in a sequencer flow cell channel); sequence regions required for the binding of sequencing primers; and/or a random sequence (e.g., a random N-mer) that may be useful, for example, in random amplification schemes. An adaptor can be attached to a nucleic acid to be sequenced, for example, by amplification, ligation, or any other method described herein.

Moreover, an oligonucleotide barcode, and/or a larger oligonucleotide comprising an oligonucleotide barcode may comprise natural nucleic acid bases and/or may comprise non-natural bases. For example, in cases where an oligonucleotide barcode or a larger oligonucleotide comprising an oligonucleotide barcode is DNA, the oligonucleotide may comprise the natural DNA bases adenine, guanine, cytosine, and thymine and/or may comprise non-natural bases such as uracil.

V. DEVICES AND SYSTEMS

Also provided herein are the microfluidic devices used for partitioning the cells as described above. Such microfluidic devices can comprise channel networks for carrying out the partitioning process like those set forth in FIGS. 1 and 2. Examples of particularly useful microfluidic devices are described in U.S. Provisional Patent Application No. 61/977,804, filed Apr. 4, 2014, and incorporated herein by reference in its entirety for all purposes. Briefly, these microfluidic devices can comprise channel networks, such as those described herein, for partitioning cells into separate partitions, and co-partitioning such cells with oligonucleotide barcode library members, e.g., disposed on beads. These channel networks can be disposed within a solid body, e.g., a glass, semiconductor or polymer body structure in which the channels are defined, where those channels communicate at their termini with reservoirs for receiving the various input fluids, and for the ultimate deposition of the partitioned cells, etc., from the output of the channel networks. By way of example, and with reference to FIG. 2, a reservoir fluidly coupled to channel 202 may be provided with an aqueous suspension of cells 214, while a reservoir coupled to channel 204 may be provided with an aqueous suspension of beads 216 carrying the oligonucleotides. Channel segments 206 and 208 may be provided with a non-aqueous solution, e.g., an oil, into which the aqueous fluids are partitioned as droplets at the channel junction 212. Finally, an outlet reservoir may be fluidly coupled to channel 210 into which the partitioned cells and beads can be delivered and from which they may be harvested. As will be appreciated, while described as reservoirs, it will be appreciated that the channel segments may be coupled to any of a variety of different fluid sources or receiving components, including tubing, manifolds, or fluidic components of other systems.

Also provided are systems that control flow of these fluids through the channel networks e.g., through applied pressure differentials, centrifugal force, electrokinetic pumping, capillary or gravity flow, or the like.

VI. KITS

Also provided herein are kits for analyzing individual cells or small populations of cells. The kits may include one, two, three, four, five or more, up to all of partitioning fluids, including both aqueous buffers and non-aqueous partitioning fluids or oils, nucleic acid barcode libraries that are releasably associated with beads, as described herein, microfluidic devices, reagents for disrupting cells amplifying nucleic acids, and providing additional functional sequences on fragments of cellular nucleic acids or replicates thereof, as well as instructions for using any of the foregoing in the methods described herein.

VII. COMPUTER CONTROL SYSTEMS

Figure 17:
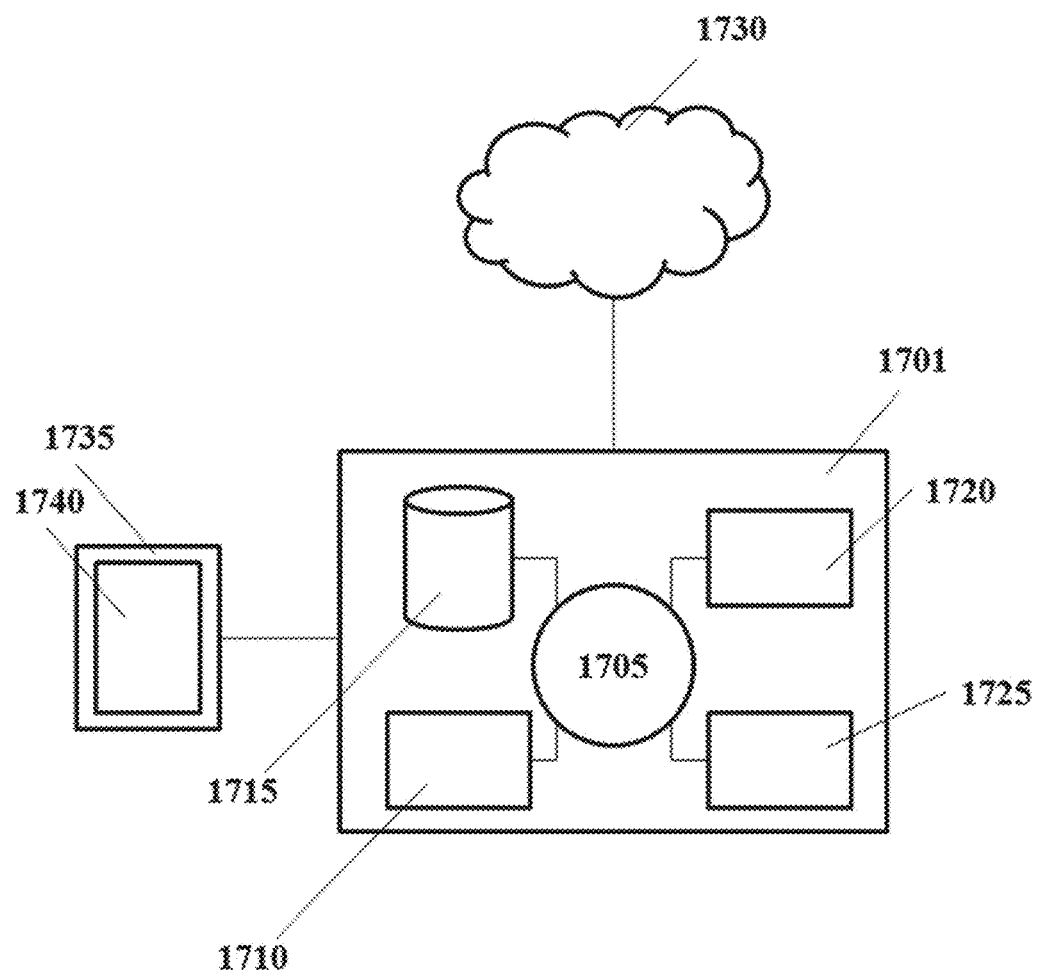
FIG. 17 shows an example computer control system that is programmed or otherwise configured to implement methods provided herein.

The present disclosure provides computer control systems that are programmed to implement methods of the disclosure. FIG. 17 shows a computer system 1701 that is programmed or otherwise configured to implement methods of the disclosure including nucleic acid sequencing methods, interpretation of nucleic acid sequencing data and analysis of cellular nucleic acids, such as RNA (e.g., mRNA), and characterization of cells from sequencing data. The computer system 1701 can be an electronic device of a user or a computer system that is remotely located with respect to the electronic device. The electronic device can be a mobile electronic device.

The computer system 1701 includes a central processing unit (CPU, also "processor" and "computer processor" herein) 1705, which can be a single core or multi core processor, or a plurality of processors for parallel processing. The computer system 1701 also includes memory or memory location 1710 (e.g., random-access memory, read-only memory, flash memory), electronic storage unit 1715 (e.g., hard disk), communication interface 1720 (e.g., network adapter) for communicating with one or more other systems, and peripheral devices 1725, such as cache, other memory, data storage and/or electronic display adapters. The memory 1710, storage unit 1715, interface 1720 and peripheral devices 1725 are in communication with the CPU 1705 through a communication bus (solid lines), such as a motherboard. The storage unit 1715 can be a data storage unit (or data repository) for storing data. The computer system 1701 can be operatively coupled to a computer network ("network") 1730 with the aid of the communication interface 1720. The network 1730 can be the Internet, an internet and/or extranet, or an intranet and/or extranet that is in communication with the Internet. The network 1730 in some cases is a telecommunication and/or data network. The network 1730 can include one or more computer servers, which can enable distributed computing, such as cloud computing. The network 1730, in some cases with the aid of the computer system 1701, can implement a peer-to-peer network, which may enable devices coupled to the computer system 1701 to behave as a client or a server.

The CPU 1705 can execute a sequence of machine-readable instructions, which can be embodied in a program or software. The instructions may be stored in a memory location, such as the memory 1710. The instructions can be directed to the CPU 1705, which can subsequently program or otherwise configure the CPU 1705 to implement methods of the present disclosure. Examples of operations performed by the CPU 1705 can include fetch, decode, execute, and writeback.

The CPU 1705 can be part of a circuit, such as an integrated circuit. One or more other components of the system 1701 can be included in the circuit. In some cases, the circuit is an application specific integrated circuit (ASIC).

The storage unit 1715 can store files, such as drivers, libraries and saved programs. The storage unit 1715 can store user data, e.g., user preferences and user programs. The computer system 1701 in some cases can include one or more additional data storage units that are external to the computer system 1701, such as located on a remote server that is in communication with the computer system 1701 through an intranet or the Internet.

The computer system 1701 can communicate with one or more remote computer systems through the network 1730. For instance, the computer system 1701 can communicate with a remote computer system of a user. Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 1701 via the network 1730.

Methods as described herein can be implemented by way of machine (e.g., computer processor) executable code stored on an electronic storage location of the computer system 1701, such as, for example, on the memory 1710 or electronic storage unit 1715. The machine executable or machine readable code can be provided in the form of software. During use, the code can be executed by the processor 1705. In some cases, the code can be retrieved from the storage unit 1715 and stored on the memory 1710 for ready access by the processor 1705. In some situations, the electronic storage unit 1715 can be precluded, and machine-executable instructions are stored on memory 1710.

The code can be pre-compiled and configured for use with a machine having a processor adapted to execute the code, or can be compiled during runtime. The code can be supplied in a programming language that can be selected to enable the code to execute in a pre-compiled or as-compiled fashion.

Aspects of the systems and methods provided herein, such as the computer system 1701, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 1701 can include or be in communication with an electronic display 1735 that comprises a user interface (UI) 1740 for providing, for example, results of nucleic acid sequencing, analysis of nucleic acid sequencing data, characterization of nucleic acid sequencing samples, cell characterizations, etc. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 1705. The algorithm can, for example, initiate nucleic acid sequencing, process nucleic acid sequencing data, interpret nucleic acid sequencing results, characterize nucleic acid samples, characterize cells, etc.

VIII. EXAMPLES

Example I Cellular RNA Analysis Using Emulsions

In an example, reverse transcription with template switching and cDNA amplification (via PCR) is performed in emulsion droplets with operations as shown in FIG. 9A. The reaction mixture that is partitioned for reverse transcription and cDNA amplification (via PCR) includes 1,000 cells or 10,000 cells or 10 ng of RNA, beads bearing barcoded oligonucleotides/0.2% Tx-100/5× Kapa buffer, 2× Kapa HS HiFi Ready Mix, 4 µM switch oligo, and Smartscribe. Where cells are present, the mixture is partitioned such that a majority or all of the droplets comprise a single cell and single bead. The cells are lysed while the barcoded oligonucleotides are released from the bead, and the poly-T segment of the barcoded oligonucleotide hybridizes to the poly-A tail of mRNA that is released from the cell as in operation 950. The poly-T segment is extended in a reverse transcription reaction as in operation 952 and the cDNA transcript is amplified as in operation 954. The thermal cycling conditions are 42° C. for 130 minutes; 98° C. for 2 min; and 35 cycles of the following 98° C. for 15 sec, 60° C. for 20 sec, and 72° C. for 6 min. Following thermal cycling, the emulsion is broken and the transcripts are purified with Dynabeads and 0.6×SPRI as in operation 956.

Figure 13A:
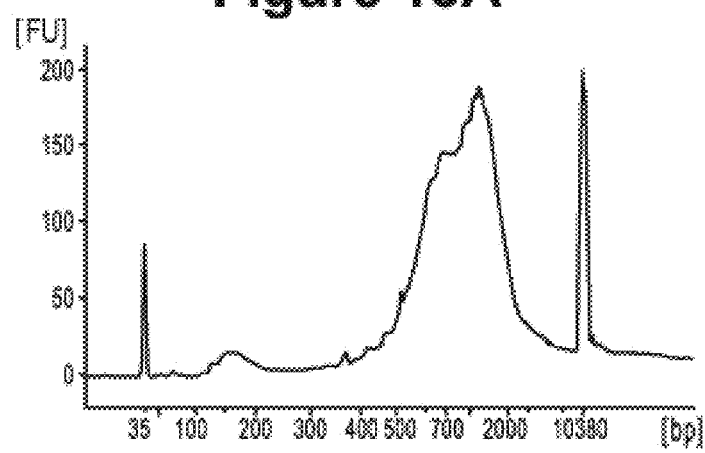
FIG. 13A-C provides illustrations of example yields from template switch reverse transcription and PCR in partitions.
Figure 13B:
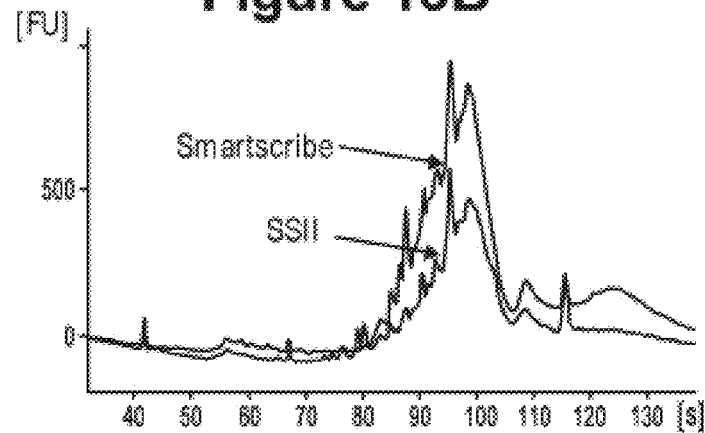
Figure 13C:
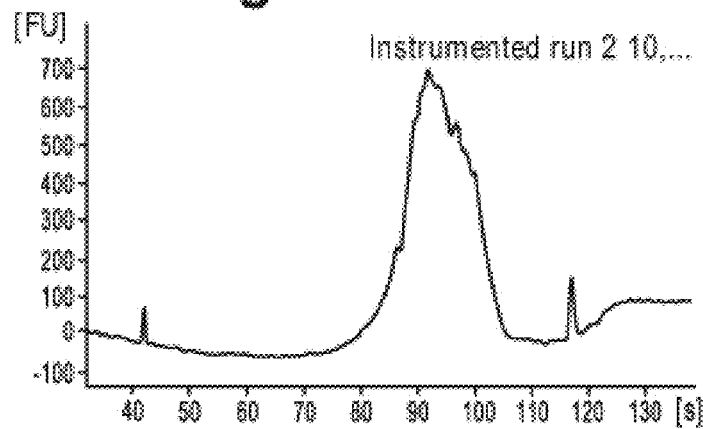

The yield from template switch reverse transcription and PCR in emulsions is shown for 1,000 cells in FIG. 13A and 10,000 cells in FIG. 13C and 10 ng of RNA in FIG. 13B (Smartscribe line). The cDNA transcripts from RT and PCR performed in emulsions for 10 ng RNA is sheared and ligated to functional sequences, cleaned up with 0.8×SPRI, and is further amplified by PCR as in operation 958. The amplification product is cleaned up with 0.8×SPRI. The yield from this processing is shown in FIG. 13B (SSII line).

Example II Cellular RNA Analysis Using Emulsions

Figure 14B:
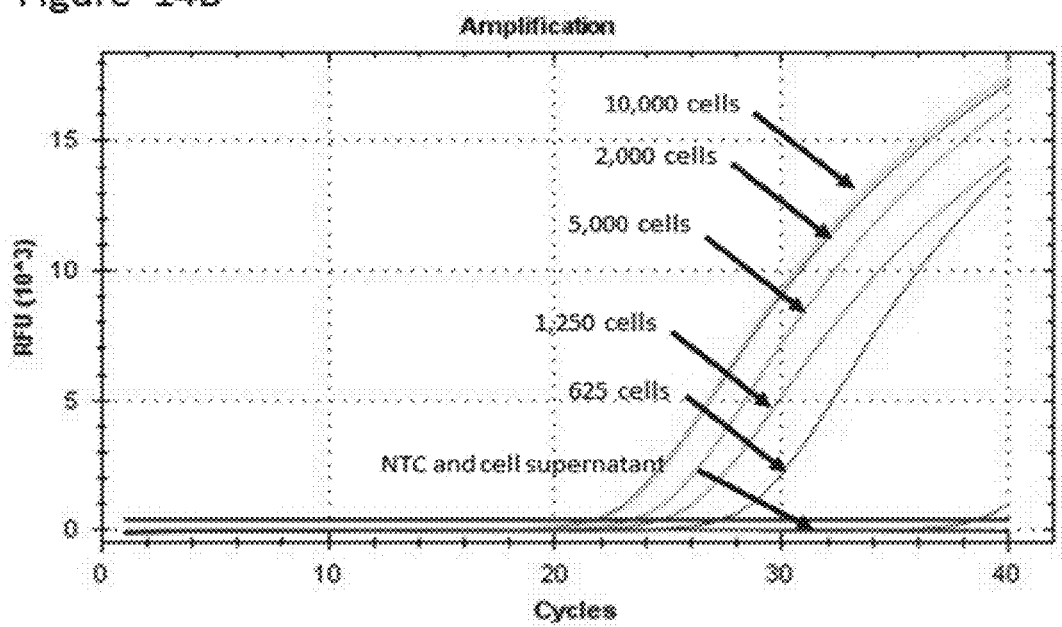

In another example, reverse transcription with template switching and cDNA amplification (via PCR) is performed in emulsion droplets with operations as shown in FIG. 9A. The reaction mixture that is partitioned for reverse transcription and cDNA amplification (via PCR) includes Jurkat cells, beads bearing barcoded oligonucleotides/0.2% TritonX-100/5×Kapa buffer, 2×Kapa HS HiFi Ready Mix, 4 µM switch oligo, and Smartscribe. The mixture is partitioned such that a majority or all of the droplets comprise a single cell and single bead. The cells are lysed while the barcoded oligonucleotides are released from the bead, and the poly-T segment of the barcoded oligonucleotide hybridizes to the poly-A tail of mRNA that is released from the cell as in operation 950. The poly-T segment is extended in a reverse transcription reaction as in operation 952 and the cDNA transcript is amplified as in operation 954. The thermal cycling conditions are 42° C. for 130 minutes; 98° C. for 2 min; and 35 cycles of the following 98° C. for 15 sec, 60° C. for 20 sec, and 72° C. for 6 min. Following thermal cycling, the emulsion is broken and the transcripts are cleaned-up with Dynabeads and 0.6×SPRI as in operation 956. The yield from reactions with various cell numbers (625 cells, 1,250 cells, 2,500 cells, 5,000 cells, and 10,000 cells) is shown in FIG. 14A. These yields are confirmed with GADPH qPCR assay results shown in FIG. 14B.

Example III RNA Analysis Using Emulsions

Figure 15:
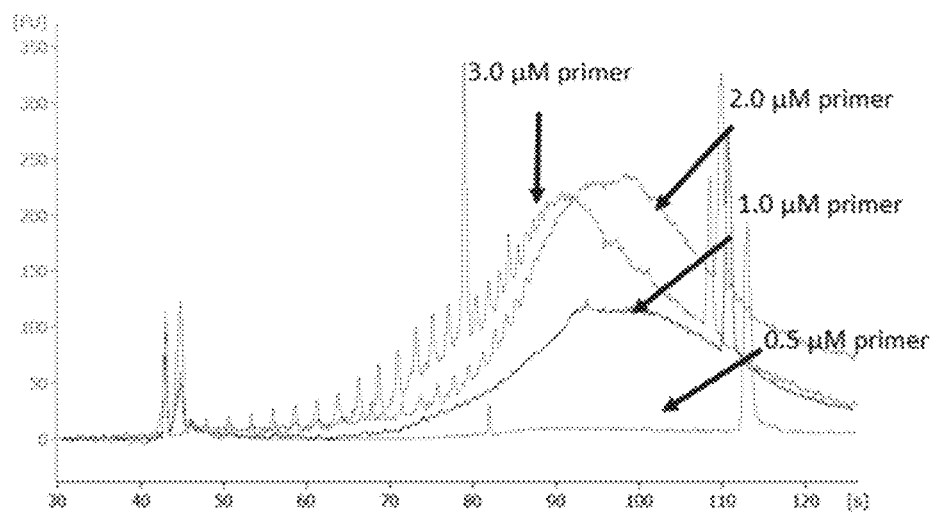
FIG. 15 provides an illustration of example yields from cDNA synthesis and real-time quantitative PCR at various input cell concentrations and also the effect of varying primer concentration on yield at a fixed cell input concentration.

In another example, reverse transcription is performed in emulsion droplets and cDNA amplification is performed in bulk in a manner similar to that as shown in FIG. 9C. The reaction mixture that is partitioned for reverse transcription includes beads bearing barcoded oligonucleotides, 10 ng Jurkat RNA (e.g., Jurkat mRNA), 5×First-Strand buffer, and Smartscribe. The barcoded oligonucleotides are released from the bead, and the poly-T segment of the barcoded oligonucleotide hybridizes to the poly-A tail of the RNA as in operation 961. The poly-T segment is extended in a reverse transcription reaction as in operation 963. The thermal cycling conditions for reverse transcription are one cycle at 42° C. for 2 hours and one cycle at 70° C. for 10 min. Following thermal cycling, the emulsion is broken and RNA and cDNA transcripts are denatured as in operation 962. A second strand is then synthesized by primer extension with a primer having a biotin tag as in operation 964. The reaction conditions for this primer extension include cDNA transcript as the first strand and biotinylated extension primer ranging in concentration from 0.5-3.0 μM. The thermal cycling conditions are one cycle at 98° C. for 3 min and one cycle of 98° C. for 15 sec, 60° C. for 20 sec, and 72° C. for 30 min. Following primer extension, the second strand is pulled down with Dynabeads MyOne Streptavidin C1 and T1, and cleaned-up with Agilent SureSelect XT buffers. The second strand is pre-amplified via PCR as in operation 965 with the following cycling conditions—one cycle at 98° C. for 3 min and one cycle of 98° C. for 15 sec, 60° C. for 20 sec, and 72° C. for 30 min. The yield for various concentrations of biotinylated primer (0.5 μM, 1.0 μM, 2.0 μM, and 3.0 μM) is shown in FIG. 15.

Example IV RNA Analysis Using Emulsions

Figure 16:
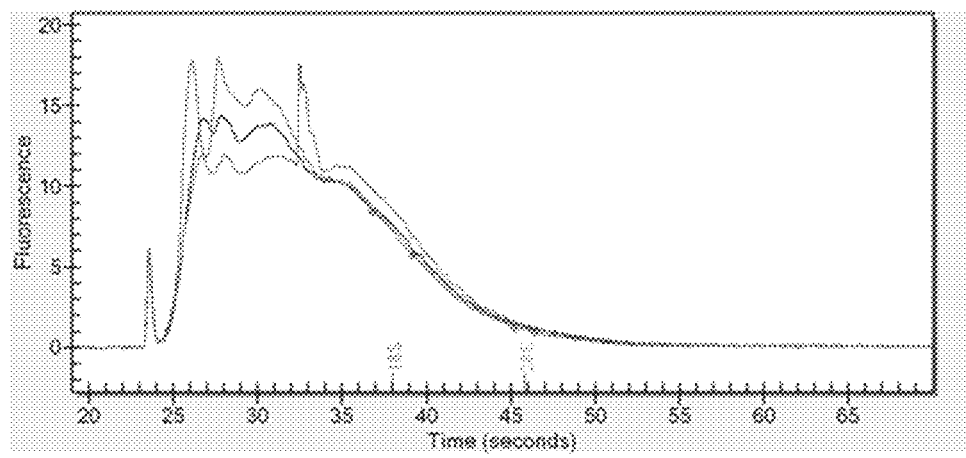
FIG. 16 provides an illustration of example yields from in vitro transcription.

In another example, in vitro transcription by T7 polymerase is used to produce RNA transcripts as shown in FIG. 10. The mixture that is partitioned for reverse transcription includes beads bearing barcoded oligonucleotides which also include a T7 RNA polymerase promoter sequence, 10 ng human RNA (e.g., human mRNA), 5× First-Strand buffer, and Smartscribe. The mixture is partitioned such that a majority or all of the droplets comprise a single bead. The barcoded oligonucleotides are released from the bead, and the poly-T segment of the barcoded oligonucleotide hybridizes to the poly-A tail of the RNA as in operation 1050. The poly-T segment is extended in a reverse transcription reaction as in operation 1052. The thermal cycling conditions are one cycle at 42° C. for 2 hours and one cycle at 70° C. for 10 min. Following thermal cycling, the emulsion is broken and the remaining operations are performed in bulk. A second strand is then synthesized by primer extension as in operation 1054. The reaction conditions for this primer extension include cDNA transcript as template and extension primer. The thermal cycling conditions are one cycle at 98° C. for 3 min and one cycle of 98° C. for 15 sec, 60° C. for 20 sec, and 72° C. for 30 min. Following this primer extension, the second strand is purified with 0.6×SPRI. As in operation 1056, in vitro transcription is then performed to produce RNA transcripts. In vitro transcription is performed overnight, and the transcripts are purified with 0.6×SPRI. The RNA yields from in vitro transcription are shown in FIG. 16.

While some embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A system for nucleic acid processing or analysis, comprising:
   (a) a plurality of antibody-oligonucleotide conjugates, wherein an antibody-oligonucleotide conjugate of said plurality of antibody-oligonucleotide conjugates comprises an antibody and an oligonucleotide reporter molecule comprising a reporter barcode sequence, and wherein said reporter barcode sequence identifies said antibody;
   (b) a plurality of beads comprising a plurality of barcode sequences, wherein a bead of said plurality of beads comprises a plurality of nucleic acid barcode molecules comprising a common barcode sequence; and
   (c) a microwell array comprising 1,000 microwells, wherein said microwell array is configured to partition a plurality of cells and said plurality of beads into microwells of said microwell array, wherein a microwell of said microwell array comprises: (i) a single cell of said plurality of cells; and (ii) said bead, and wherein said single cell is bound to said antibody-oligonucleotide conjugate.

2. The system of claim 1, wherein said plurality of nucleic acid barcode molecules is releasably attached to said bead.

3. The system of claim 1, wherein said plurality of nucleic acid barcode molecules is attached to said bead via a disulfide bond.

4. The system of claim 1, wherein, in said microwell, said bead comprises said oligonucleotide reporter molecule attached thereto.

5. The system of claim 1, wherein said bead is a magnetic bead.

6. The system of claim 5, further comprising a magnetic source configured to produce a magnetic field, wherein said magnetic bead is removable from said microwell using said magnetic field.

7. The system of claim 1, wherein said bead is a gel bead.

8. The system of claim 1, wherein said plurality of nucleic acid barcode molecules comprises a unique molecular sequence.

9. The system of claim 8, wherein said unique molecular sequence is a random sequence.

10. The system of claim 1, wherein said microwell array comprises 10,000 microwell.

11. The system of claim 1, wherein said microwell array comprises 100,000 microwell.

12. The system of claim 1, wherein said microwell array comprises 1,000,000 microwell.

13. The system of claim 1, wherein antibody-oligonucleotide conjugates of said plurality of antibody-oligonucleotide conjugates are configured to bind to a common antigen and comprise a common reporter barcode sequence.

14. The system of claim 1, wherein antibody-oligonucleotide conjugates of said plurality of antibody-oligonucleotide conjugates are configured to bind to different antigens and comprise different reporter barcode sequences.

15. The system of claim 1, wherein said antibody-oligonucleotide conjugate is bound to a surface feature of said single cell.

16. The system of claim 1, wherein said antibody-oligonucleotide conjugate is bound to a protein of said single cell.

17. The system of claim 1, wherein said plurality of nucleic acid barcode molecules comprise one or more functional sequences selected from the group consisting of a first primer sequence, a first primer binding sequence, a capture sequence configured to attach to said reporter molecule, and a first adapter sequence configured to permit attachment to a flow cell of a sequencer.

18. The system of claim 17, wherein said first primer sequence comprises a sequencing primer sequence, or wherein said first primer binding sequence comprises a sequencing primer binding sequence.

19. The system of claim 17, wherein said reporter molecule comprises one or more functional sequences selected from the group consisting of a second primer sequence, a second primer binding sequence, a sequence complementary to said capture sequence, and a second adapter sequence configured to permit attachment to said flow cell of said sequencer.

20. The system of claim 1, further comprising reagents configured to generate a barcoded nucleic acid molecule comprising said reporter barcode sequence and said common barcode sequence.

21. The system of claim 20, wherein said reagents comprise one or more components selected from the group consisting of a buffer, a polymerase, a ligase, and a primer.

22. The system of claim 20, further comprising a sequencing component comprising a sequencing instrument, wherein said sequencing component is configured to generate sequencing reads corresponding to said reporter barcode sequence and said common barcode sequence.

23. The system of claim 22, further comprising a computing component comprising a processor, a user interface, and an electronic display, wherein said computing component is configured to analyze said sequencing reads and display an analysis of nucleic acid sequencing data on said electronic display.

24. The system of claim 1, wherein said microwell of said microwell array is configured to accommodate a volume of less than about 500 nanoliters (nL).

25. The system of claim 1, wherein said common barcode sequence is different from barcode sequences of other barcode molecules attached to other beads in other microwells of said microwell array.

26. A system for nucleic acid processing, comprising:
a microwell array comprising a plurality of microwells configured to partition (i) a plurality of beads comprising nucleic acid molecules comprising barcode sequences, and (ii) a plurality of cells;
wherein said plurality of microwells comprises 1,000 microwells;
wherein a microwell of said plurality of microwells is configured to accommodate a volume of less than about 5 nanoliters (nL);
wherein said system is configured to partition said plurality of beads such that said barcode sequences are different across microwells of said microwell array;
wherein said microwell is configured to comprise: (i) a cell of said plurality of cells; and (ii) a bead of said plurality of beads, wherein said cell is bound to an antibody-oligonucleotide conjugate comprising an antibody and an oligonucleotide reporter molecule comprising a reporter barcode sequence, and wherein said reporter barcode sequence identifies said antibody.

27. A microfluidic system for nucleic acid processing or analysis, comprising:
(a) a plurality of antibody-oligonucleotide conjugates, wherein an antibody-oligonucleotide conjugate of said plurality of antibody-oligonucleotide conjugates comprises an antibody and an oligonucleotide reporter molecule comprising a reporter barcode sequence, and wherein said reporter barcode sequence identifies said antibody;
(b) a plurality of beads comprising a plurality of barcode sequences, wherein a bead of said plurality of beads comprises a plurality of nucleic acid barcode molecules comprising a common barcode sequence; and
(c) a microfluidic device comprising a channel network configured to partition a plurality of cells and said plurality of beads into a plurality of droplets, wherein a droplet of said plurality of droplets comprises: (i) a single cell of said plurality of cells; and (ii) said bead, and wherein said single cell is bound to said antibody-oligonucleotide conjugate.

28. A microfluidic system for nucleic acid processing, comprising:
a microfluidic device comprising a channel network configured to partition (i) a plurality of cells (ii) a plurality of beads, and (iii) a plurality of nucleic acid barcode molecules into a plurality of droplets,
wherein said plurality of nucleic acid barcode molecules comprises a plurality of nucleic acid barcode sequences that are different across said plurality of droplets,
wherein a droplet of said plurality of droplets comprises: (i) a cell of said plurality of cells; and (ii) a nucleic acid barcode molecule of said plurality of nucleic acid barcode molecules, wherein said cell is bound to an antibody-oligonucleotide conjugate comprising an antibody and an oligonucleotide reporter molecule comprising a reporter barcode sequence, wherein said reporter barcode sequence identifies said antibody, and wherein said nucleic acid barcode molecule is attached to a bead of said plurality of beads and comprises a barcode sequence of said plurality of barcode sequences.

29. The microfluidic system of claim 27, wherein a channel of said channel network is configured to receive an input fluid comprising said plurality of cells.

30. The microfluidic system of claim 27, wherein a channel of said channel network is fluidly coupled to an outlet reservoir that is configured to receive said droplet.

31. The system of claim 26, wherein said microwell comprises said cell of said plurality of cells.

32. The system of claim 26, wherein said microwell comprises said bead of said plurality of beads.

33. The system of claim 26, wherein said microwell comprises said cell of said plurality of cells and said bead of said plurality of beads.

34. The system of claim 26, wherein said bead is a gel bead.

35. The system of claim 26, wherein said bead comprises a disulfide bond.

36. The system of claim 26, wherein a nucleic acid molecule comprising a barcode sequence of said barcode sequences is attached to said bead via a covalent linkage.

37. The system of claim 36, wherein said covalent linkage is a disulfide bond.

38. The system of claim 26, wherein a nucleic acid molecule comprising a barcode sequence of said barcode sequences is releasably attached to said bead.

39. The system of claim 38, wherein said microwell comprises an agent configured to release said nucleic acid molecule from said bead.

40. The system of claim 26, wherein said antibody is configured to bind to a tumor cell.

41. The system of claim 26, wherein said antibody is configured to bind to a neural cell.

42. The system of claim 26, wherein said antibody is configured to bind to a cell surface feature of said cell.

43. The system of claim 42, wherein said cell surface feature is a cell surface protein.

44. The system of claim 26, wherein said antibody is configured to bind to a protein of said cell.

45. The system of claim 26, wherein said nucleic acid molecules comprising barcode sequences comprise a polythymine (poly-T) sequence.

46. The system of claim 26, wherein said nucleic acid molecules comprising barcode sequences comprise one or more functional sequences selected from the group consisting of a first primer sequence, a first primer binding sequence, a capture sequence configured to attach to said oligonucleotide reporter molecule, and a first adapter sequence configured to permit attachment to a flow cell of a sequencer.

47. The system of claim 46, wherein said oligonucleotide reporter molecule comprises one or more functional sequences selected from the group consisting of a second primer sequence, a second primer binding sequence, a sequence complementary to said capture sequence, and a second adapter sequence configured to permit attachment to said flow cell of said sequencer.

48. The system of claim 26, wherein said bead is a degradable bead.

49. The system of claim 48, wherein said microwell comprises an agent configured to degrade said bead.

50. The system of claim 49, wherein said agent is a reducing agent.

51. The system of claim 26, wherein said microwell comprises a template switching oligonucleotide.

52. The system of claim 26, wherein said nucleic acid molecules comprising barcode sequences comprise a unique molecular identifier.

53. The system of claim 26, wherein said microwell comprises a polymerase.

54. The system of claim 26, wherein said microwell comprises a ligase.

55. The system of claim 26, wherein said bead comprises a plurality of nucleic acid molecules comprising a common barcode sequence.

56. The system of claim 55, further comprising a sequencing module configured to generate sequencing reads corresponding to said reporter barcode sequence and said common barcode sequence.

57. The system of claim 56, further comprising a computing module comprising a processor, a user interface, and an electronic display, wherein said computing module is configured to analyze said sequencing reads and display an analysis of nucleic acid sequencing data on said electronic display.

* * * * *

UNITED STATES PATENT AND TRADEMARK OFFICE
CERTIFICATE OF CORRECTION

PATENT NO. : 10,450,607 B2
APPLICATION NO. : 16/294769
DATED : October 22, 2019
INVENTOR(S) : Benjamin Hindson et al.

Page 1 of 1

It is certified that error appears in the above-identified patent and that said Letters Patent is hereby corrected as shown below:

In the Claims

At Column 51, Line 12, Claim 10, please change "microwell" to -- microwells --

At Column 51, Line 14, Claim 11, please change "microwell" to -- microwells --

At Column 51, Line 16, Claim 12, please change "microwell" to -- microwells --

At Column 51, Line 43, Claim 19, please change "The system of claim 17, wherein said reporter molecule" to -- The system of claim 17, wherein said oligonucleotide reporter molecule --

Signed and Sealed this
Third Day of March, 2020

Andrei Iancu
*Director of the United States Patent and Trademark Office*